US010465214B2

(12) United States Patent
Anderson et al.

(10) Patent No.: US 10,465,214 B2
(45) Date of Patent: Nov. 5, 2019

(54) PRODUCING RESINS FROM ORGANIC WASTE PRODUCTS

(71) Applicant: Full Cycle Bioplastics LLC, Richmond, CA (US)

(72) Inventors: Jeff H. Anderson, Albany, CA (US); Dane H. Anderson, Albany, CA (US)

(73) Assignee: Full Cycle Bioplastics LLC, Richmond, CA (US)

( * ) Notice: Subject to any disclaimer, the term of this patent is extended or adjusted under 35 U.S.C. 154(b) by 0 days.

(21) Appl. No.: 14/947,873

(22) Filed: Nov. 20, 2015

(65) Prior Publication Data

US 2016/0145659 A1  May 26, 2016

Related U.S. Application Data

(60) Provisional application No. 62/082,526, filed on Nov. 20, 2014, provisional application No. 62/082,527, filed on Nov. 20, 2014, provisional application No. 62/082,528, filed on Nov. 20, 2014.

(51) Int. Cl.
| | | |
|---|---|---|
| *C12P 7/64* | (2006.01) | |
| *C08G 63/06* | (2006.01) | |
| *C08G 63/89* | (2006.01) | |
| *C12M 1/00* | (2006.01) | |
| *C12M 1/34* | (2006.01) | |
| *C12Q 3/00* | (2006.01) | |
| *C12P 7/62* | (2006.01) | |
| *B01D 61/02* | (2006.01) | |
| *B01D 61/12* | (2006.01) | |

(52) U.S. Cl.
CPC .......... *C12P 7/6436* (2013.01); *B01D 61/025* (2013.01); *B01D 61/027* (2013.01); *B01D 61/12* (2013.01); *C08G 63/06* (2013.01); *C08G 63/89* (2013.01); *C12M 23/58* (2013.01); *C12M 29/04* (2013.01); *C12M 41/32* (2013.01); *C12P 7/625* (2013.01); *C12Q 3/00* (2013.01); *B01D 2311/2607* (2013.01); *B01D 2313/34* (2013.01)

(58) Field of Classification Search
CPC ...... C12P 7/6436; C12P 7/625; B01D 61/025; B01D 61/027; B01D 61/12; B01D 2311/2607; B01D 2313/34; C08G 63/06; C08G 63/89; C12M 23/58; C12M 29/04; C12M 41/32; C12Q 3/00
USPC ....................................................... 435/41
See application file for complete search history.

(56) References Cited

U.S. PATENT DOCUMENTS

| | | | |
|---|---|---|---|
| 5,811,272 A | 9/1998 | Snell et al. | |
| 6,630,067 B2 | 10/2003 | Shieh et al. | |
| 6,770,464 B2 | 8/2004 | Steinbuechel et al. | |
| 6,987,011 B1 | 1/2006 | Reid et al. | |
| 6,991,931 B2 | 1/2006 | Dragotta et al. | |
| 7,098,292 B2 | 8/2006 | Zhao et al. | |
| 7,141,400 B2 | 11/2006 | Yu | |
| 7,378,266 B2 | 5/2008 | Narasimhan et al. | |
| 7,854,841 B2 | 12/2010 | Oh | |
| 7,887,893 B2 | 2/2011 | Billington et al. | |
| 8,030,021 B2 | 10/2011 | Griddle et al. | |
| 8,187,462 B2 | 5/2012 | Bengtsson et al. | |
| 2003/0004299 A1 | 1/2003 | Srienc et al. | |
| 2006/0014921 A1 | 1/2006 | Mihara et al. | |
| 2009/0042266 A1* | 2/2009 | Vehmaanpera ........... C12P 7/10 435/165 |
| 2009/0233338 A1 | 9/2009 | Jacobs | |
| 2011/0159556 A1 | 6/2011 | Pieja et al. | |
| 2011/0160427 A1 | 6/2011 | Hassan et al. | |
| 2012/0077254 A1 | 3/2012 | Morse et al. | |

FOREIGN PATENT DOCUMENTS

| | | |
|---|---|---|
| CA | 2487116 C | 2/2012 |
| CN | 101058799 A | 10/2007 |
| CN | 101323864 A | 12/2008 |
| CN | 101555314 A | 10/2009 |
| CN | 101993896 A | 3/2011 |
| CN | 102505025 A | 6/2012 |
| CN | 103332829 A | 10/2013 |
| EP | 1400569 B1 | 4/2006 |

(Continued)

OTHER PUBLICATIONS

Huang et al., Polyanaline Membranes for Pervaporation of Carboxylic Acids and Water, Macromolecules, 31 (1998) pp. 5456-5464.*

(Continued)

*Primary Examiner* — Jennifer M. H. Tichy
(74) *Attorney, Agent, or Firm* — Fish & Richardson P.C.

(57) ABSTRACT

Producing a resin from an organic waste product includes assessing a weight percent of a first volatile fatty acid and a weight percent of a second volatile fatty acid in a liquid mixture having volatile fatty acids from the organic waste product. The weight percent of the volatile fatty acids is based on the total weight of the carboxylic acids in the liquid mixture, the total weight of volatile fatty acids in the liquid mixture, or the total weight of lactic acid and volatile fatty acids in the mixture. A ratio of the weight percent of the first volatile fatty acid to the weight percent of the second volatile fatty acid in the liquid mixture is adjusted to yield a modified liquid mixture. The modified liquid is combined with polyhydroxyalkanoate-producing bacteria to yield a polyhydroxyalkanoate copolymer; and the polyhydroxyalkanoate copolymer is extracted from the polyhydroxyalkanoate-producing bacteria.

22 Claims, 14 Drawing Sheets

(56) References Cited

FOREIGN PATENT DOCUMENTS

| | | |
|---|---|---|
| EP | 1118629 B1 | 4/2007 |
| EP | 1113033 B1 | 11/2008 |
| EP | 2202316 B1 | 9/2013 |
| JP | 10191992 A | 7/1998 |
| JP | 2000189183 A | 7/2000 |
| WO | WO2002013877 A8 | 11/2003 |
| WO | WO2005092948 A3 | 1/2007 |
| WO | WO2009038530 A1 | 3/2009 |
| WO | WO2009045719 A3 | 6/2009 |
| WO | WO2011002270 A1 | 1/2011 |
| WO | WO2011031566 A1 | 3/2011 |
| WO | WO2011070544 A | 6/2011 |
| WO | WO2011073744 A1 | 6/2011 |
| WO | WO2011106848 A1 | 9/2011 |
| WO | WO2011108916 A3 | 11/2011 |
| WO | WO2012166822 A3 | 3/2014 |

OTHER PUBLICATIONS

Hashizume et al., Constituents of Cane Molasses, Agr. Biol. Chem., vol. 30, No. 4 (1966) pp. 319-329.*

Dictionary.com, "Liquefy," Accessed Dec. 6, 2018, Online at: www.dictionary.com/ browse/liquefy.*

Erik R. Coats et al., "Toward Polyhydroxyalkanoate Production Concurrent with Municipal Wastewater Treatment in a Sequencing Batch Reactor System," Journal of Environmental Engineering, vol. 137, Issue 7, Jan. 2011, pp. 46-54.

Lara L. Madison et al., "Metabolic Engineering of Poly(3-Hydroxyalkanoates): From DNA to Plastic," Microbiology and Molecular Biology Reviews, vol. 63, No. 1, Mar. 1999, pp. 21-53.

Warangkana Punrattanasin, "The Utilization of Activated Sludge Polyhydroxyalkanoates for the Production of Biodegradable Plastics," Dissertation submitted to the Faculty of the Virginia Polytechnic Institute and State University in partial fulfillment of the requirements for the degree of Doctor of Philosophy in Environmental Science and Engineering, Apr. 13, 2001, 131 pages.

Authorized Anita Rothenbucher, International Search Report and Written Opinion for International Application No. PCT/US2015/061991, dated Feb. 25, 2016, 14 pages.

Bengtsson S et al: "Production of polyhydroxyalkanoates from fermented sugar cane molasses by a mixed culture enriched in glycogen accumulating organisms", Journal of Biotechnology, vol. 145, No. 3, Feb. 1, 2010 (Feb. 1, 2010), pp. 253-263.

Albuquerque et al: "Strategies for the development of a side stream process for polyhydroxyalkanoate (PHA) production from sugar cane molasses", Journal of Biotechnology, vol. 130, No. 4, Jul. 10, 2007 (Jul. 10, 2007), pp. 411-421.

* cited by examiner

PRODUCING RESINS FROM ORGANIC WASTE PRODUCTS

CROSS-REFERENCE TO RELATED APPLICATIONS

This application claims the benefit of U.S. Provisional Patent Application No. 62/082,526, filed Nov. 20, 2014, titled "Process for Resin Production from Waste Products," U.S. Provisional Patent Application No. 62/082,527, filed Nov. 20, 2014, titled "Multiple Electron Salt for Roadway Applications," and U.S. Provisional Patent Application No. 62/082,528, filed Nov. 20, 2014, titled "Method and Apparatus for Electromagnetic Separation," all of which are incorporated herein by reference in their entireties.

TECHNICAL FIELD

The present disclosure generally relates to a process for the production of bioplastic resins, and more specifically to the production of plastic resins from organic waste products.

BACKGROUND

Plastic resins are used for many products, as plastic is moldable and can be tailored to have specific tensile and shear strengths, and other materials properties that can be changed based on the material composition, for various applications. As used herein, "resin" generally refers to a polymer or copolymer. Plastics are often produced from petroleum or other oil-based materials. However, such plastic products, such as water bottles and other packaging items, are often not biodegradable, and as such are not as reusable or effectively recyclable in terms of cost. Although petroleum-based plastics are recyclable, the cost to recycle these products is high. Further, petroleum-based plastics are increasingly ending up in landfills, oceans, and other places where ecological damage is becoming an increasing concern.

Because of the increased costs of petroleum products, and the ecological effects of non-biodegradable plastics, there have been recent attempts at manufacturing biodegradable plastics, which are often referred to as "bioplastics." Many of these attempts have been accompanied with high cost, low recycling yield, and other barriers to entry for a bioplastic facility. As such, the ability of bioplastics to compete with petroleum-based plastics has not yet been fully achieved.

Of particular interest are plastic resins known as polyhydroxyalkanoate (PHA) resins. PHAs combine sufficient biodegradability characteristics with desirable material properties, which allow the use of PHAs in a larger number of applications over other biodegradable plastic materials. However, one of the barriers to market entry for PHAs has been the cost of production being tied to the cost of sugar, which is used as a raw material for producing PHAs. Because the cost of the raw material used to produce PHA is subject to many market forces, biodegradable PHAs are often sold at a premium price versus petroleum-based plastics having comparable material properties. This price differential has discouraged markets from employing PHAs on a large scale.

SUMMARY

In some aspects, the present disclosure relates to the production of bioplastic resins, and more specifically for the production of polyhydroxyalkanoate copolymers from organic waste products.

In a first general aspect, producing copolymer resins includes analyzing an input material, processing the input material based at least in part on the analysis of the input material, analyzing the processed input material, separating the processed input material based at least in part on the analysis of the processed input material, analyzing the separated processed input material, and polymerizing the processed input material based at least in part on the analysis of the separated processed input material.

In a second general aspect, producing a bioplastic resin or polyhydroxyalkanoate copolymer from an organic waste product includes assessing a wt % of a first volatile fatty acid and a wt % of a second volatile fatty acid in a liquid mixture including volatile fatty acids from the organic waste product based on the total weight of the carboxylic acids in the liquid mixture, the total weight of volatile fatty acids in the liquid mixture, or the total weight of lactic acid and volatile fatty acids in the mixture. The ratio of the wt % of the first volatile fatty acid to the wt % of the second volatile fatty acid in the liquid mixture is adjusted to yield a modified liquid mixture. The modified liquid mixture is combined with polyhydroxyalkanoate-producing bacteria to yield a polyhydroxyalkanoate copolymer; and the polyhydroxyalkanoate copolymer is extracted from the polyhydroxyalkanoate-producing bacteria.

Implementations of the second general aspect may include one or more of the following features.

In some implementations, producing a bioplastic resin or polyhydroxyalkanoate copolymer from an organic waste product may include combining acidogenic bacteria with a feedstock including the organic waste product to yield the liquid mixture including the volatile fatty acids. In some cases, bioplastic resin or polyhydroxyalkanoate copolymer from an organic waste product includes liquefying the organic waste product to yield the feedstock.

In some implementations, adjusting the relative concentration of the first volatile fatty acid and the second volatile fatty acid includes combining an additional quantity of the first volatile fatty acid, an additional quantity of the second volatile fatty acid, or both to the liquid mixture. In certain implementations, adjusting the relative concentration of the first volatile fatty acid and the second volatile fatty acid includes removing a quantity of the first volatile fatty acid, a quantity of the second volatile fatty acid, or both from the liquid mixture. In one example in which the second volatile fatty acid is physically larger than the first volatile fatty acid in at least one dimension, implementations may include directing the fluid mixture through a first conduit towards a first filter with a maximum pore size that is selected to allow at least the first volatile fatty acid and the second volatile fatty acid to pass therethrough while preventing compounds larger than the first volatile fatty acid and the second volatile fatty acid from passing through the first filter, directing the first filtrate passing through the first filter towards a second filter with pores large enough to allow the first volatile fatty acid to pass therethrough and small enough to inhibit the second volatile fatty acid from passing through the second filter, and removing a liquid containing the second volatile fatty acid from a conduit between the first filter and the second filter. In some cases, an electromagnetic field is induced in the first conduit adjacent the second filter, the electromagnetic field having a strength and polarity selected to inhibit the second volatile fatty acid from passing through the second filter.

In some implementations, the modified liquid mixture includes at least two of acetic acid, propionic acid, lactic acid, butyric acid, iso-butyric acid, valeric acid, iso-valeric acid, and hexanoic acid. In a first example, the modified liquid mixture includes at least 30 wt % acetic acid, 0 wt % to 70 wt % propionic acid, 0 wt % to 30 wt % lactic acid, and 0 wt % to 50 wt % butyric acid, 0 wt % to 30 wt % iso-butyric acid, 0 wt % to 50 wt % valeric acid, 0 wt % to 30 wt % iso-valeric acid, and 0 wt % to 50 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture. In a second example, the modified liquid mixture includes at least 60 wt % acetic acid, 0 wt % to 40 wt % propionic acid, 0 wt % to 10 wt % lactic acid, 0 wt % to 40 wt % butyric acid, 0 wt % to 40 wt % iso-butyric acid, 0 wt % to 40 wt % valeric acid, 0 wt % to 40 wt % iso-valeric acid, and 0 wt % to 40 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture. In a third example, the modified liquid mixture includes at least 80 wt % acetic acid, 0 wt % to 20 wt % propionic acid, 0 wt % to 5 wt % lactic acid, 0 wt % to 20 wt % butyric acid, 0 wt % to 20 wt % iso-butyric acid, 0 wt % to 20 wt % valeric acid, 0 wt % to 20 wt % iso-valeric acid, and 0 wt % to 20 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture. In a fourth example, the modified liquid mixture includes 60 wt % to 80 wt % acetic acid, 10 wt % to 20 wt % propionic acid, 0 wt % to 10 wt % lactic acid, 5 wt % to 20 wt % butyric acid, 0 wt % to 7 wt % iso-butyric acid, 0 wt % to 10 wt % valeric acid, 0 wt % to 7 wt % iso-valeric acid, and 0 wt % to 10 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture. In a fifth example, the modified liquid mixture includes 75 wt % to 80 wt % acetic acid, 20 wt % to 25 wt % propionic acid, 0 wt % to 1 wt % lactic acid, 0 wt % to 5 wt % butyric acid, 0 wt % to 1 wt % iso-butyric acid, 0 wt % to 5 wt % valeric acid, 0 wt % to 5 wt % iso-valeric acid, and 0 wt % to 1 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture. In a sixth example, the modified liquid mixture includes 80 wt % to 100 wt %, 60 wt % to 80 wt %, 40 wt % to 60 wt %, 20 wt % to 40 wt %, or 0 wt % to 20 wt % of acetic acid and propionic acid based on the total weight of carboxylic acids in the modified liquid mixture, the total weight of volatile fatty acids in the modified liquid mixture, or the total weight of lactic acid and volatile fatty acids in the modified liquid mixture. In some cases, the modified liquid mixture has a ratio of wt % of acetic acid to wt % of propionic acid in a range of 0.4 to 13. In certain cases, the modified liquid mixture has a ratio of wt % of acetic acid to wt % of propionic acid of 3/7, 29/16, 9/5, 3/2, 39/11, 22/3, or 93/7.

In some implementations, the polyhydroxyalkanoate copolymer comprises polyhydroxybutyrate and polyhydroxyvalerate. In certain implementations, the polyhydroxyalkanoate copolymer includes lactic acid residues. In one example, the polyhydroxyalkanoate copolymer includes 50 wt % to 90 wt % (dry matter) of polyhydroxybutyrate, up to 1 wt % lactic acid residues, and the balance polyhydroxyvalerate.

In some implementations, wherein adjusting the ratio of the wt % of the first volatile fatty acid to the wt % of the second volatile fatty acid in the liquid mixture to yield a modified liquid mixture occurs automatically. In certain implementations, adjusting a ratio of the wt % of the first volatile fatty acid to the wt % of the second volatile fatty acid includes fermenting the liquid mixture in the polishing tank at a pH in a range of 4 to 6 to yield the modified liquid mixture.

In a third general aspect, a system for producing a polyhydroxyalkanoate copolymer from an organic waste product includes a first tank containing a liquid mixture, the liquid mixture including volatile fatty acids from an organic waste product; an analyzer fluidically coupled to the first tank and configured to detect the presence of a first volatile fatty acid and a second volatile fatty acid in the liquid mixture; a controller configured to adjust an input of organic compounds to the first tank to adjust a ratio of a wt % of the first volatile fatty acid to a wt % of the second volatile fatty acid in the liquid mixture, thereby yielding a modified liquid mixture; a second tank fluidically coupled to the first tank and comprising PHA-producing bacteria, wherein the second tank is configured to receive the modified liquid mixture from the first tank; and a third tank fluidically coupled to the second tank and configured to receive the PHA-producing bacteria from the second tank.

Implementations of the third general aspect may include one or more of the following features.

In some cases, the system includes a digester configured to provide the liquid mixture to the first tank. In certain cases, the system includes an apparatus configured to separate one or more volatile fatty acids from the liquid mixture. In one example, the apparatus configured to separate one or more volatile fatty acids includes a filter apparatus configured to separate the one or more volatile fatty acids from the liquid mixture. The filter apparatus may include a conduit, a membrane filter adjacent to the conduit, and a field inducing device configured to apply an electromagnetic field to a region of the conduit adjacent to the membrane filter.

In some implementations, the analyzer includes a spectrophotometer configured to detect the presence of a volatile fatty acid in the first tank. The spectrophotometer may include a sample chamber, a light source arranged to direct light through the sample chamber, a light detector arranged to receive light transmitted through the sample chamber by the light source, and a field inducing device configured to induce a field within the sample chamber between the light source and the light detector.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

The features, nature, and advantages of the present disclosure will become more apparent from the detailed description set forth below when taken in conjunction with the drawings in which like reference characters identify correspondingly throughout.

DETAILED DESCRIPTION

Figure 1A:
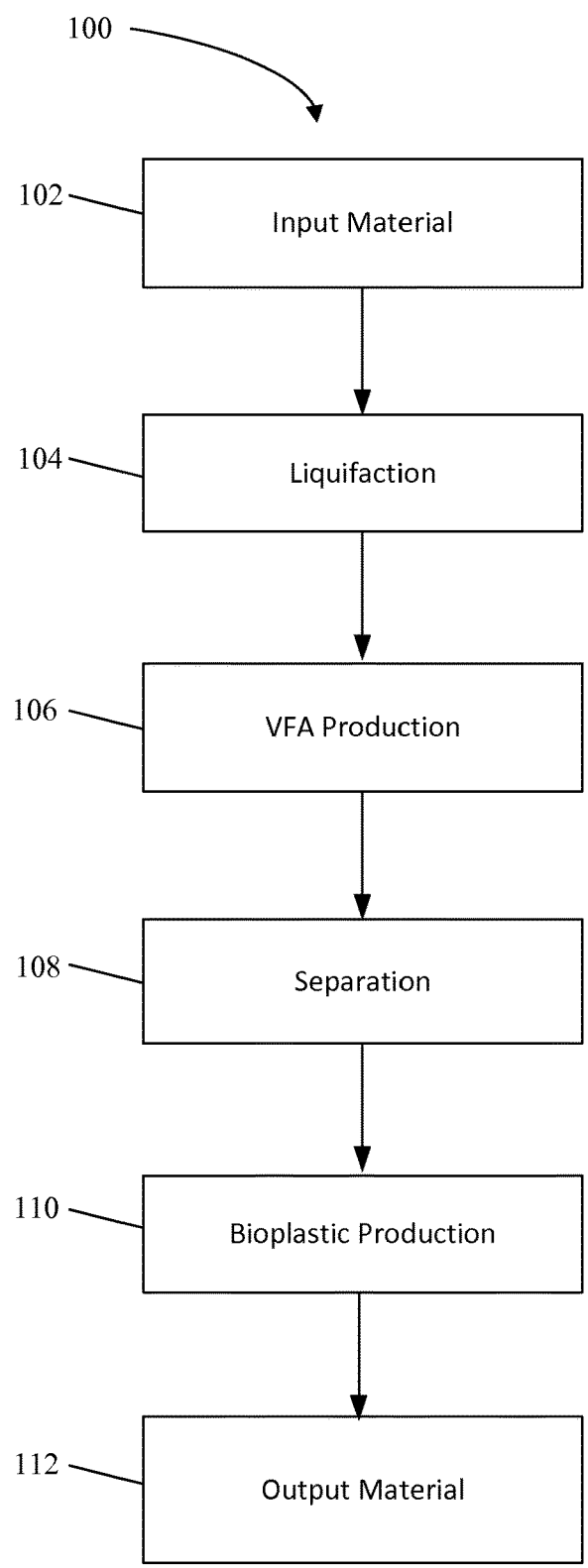
FIG. 1A is a process flow diagram illustrating an embodiment process for producing bioplastics.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent, however, to those skilled in the art that these concepts may be practiced without these specific details. In some instances, well-known structures and components are shown in block diagram form in order to avoid obscuring such concepts. As described herein, the use of the term "and/or" is intended to represent an "inclusive OR", and the use of the term "or" is intended to represent an "exclusive OR".

"Bioplastics" (or "biobased plastics") generally refers to plastics that are derived from renewable sources, plastics that are biodegradable, or both. These renewable sources may include algae, vegetable fats and oils, cornstarch, agricultural waste, and food waste. Bioplastics can be derived from organic waste products. As used herein, "organic waste products" generally includes agricultural and food processing waste, municipal waste from dedicated organic streams, organics separated from mixed fluid streams (e.g., trash sluice), organic liquid leachate extracted from composting processes, forestry or other cellulose or paper feedstocks, algae, or other biomass processing by-products such as glycerol. In general, bioplastics may be manufactured from starches, cellulose, biopolymers, and a variety of other materials. Some, but not all, bioplastics are designed to biodegrade.

The term "polyhydroxyalkanoate" (PHA) refers to a family of linear polyesters produced by the bacterial fermentation of sugars, lipids, or volatile fatty acids. PHA is a bioplastic that is biodegradable and may be derived from renewable sources, such as agricultural and food processing waste, municipal waste from dedicated organic streams, organics separated from mixed fluid streams (e.g., trash sluice), forestry or other cellulose or paper feedstocks, algae, or other biomass processing by-products such as glycerol. PHAs are produced by PHA-producing bacteria to store carbon and energy. The polyester may be extracted and purified from the PHA-producing bacteria by various processing steps.

PHA materials may comprise any of more than 150 different monomers, and may exhibit a wide range of material properties. For example, PHA can be more ductile and less elastic than other plastics, and it is also biodegradable.

PHA copolymers produced as described herein may include hydroxybutyrate (HB) and hydroxyvalerate (HV) monomer residues, as well as other monomer residues. PHA copolymers described herein may be random copolymers, block copolymers, or a combination thereof. Examples include random and block copolymers with various ratios of HB to HV monomer residues. As used herein, a ratio of monomer residues is referred to interchangeably as a ratio of the associated homopolymer (e.g., a ratio of HB to HV monomer residues in a random or block PHA copolymer may also be referred to as a ratio of polyhydroxybutyrate (PHB) to polyhydroxyvalerate (PHV) in the PHA copolymer, and vice versa).

The various devices, systems, methods, and processes described herein may be used to produce PHA resins and other products from a wide range of input materials, including food waste, garden waste, and other compostable organic materials, among others. In some embodiments, processes and systems for producing PHAs may be controlled to produce output materials with specifically targeted compositions or properties. The present disclosure describes examples of various devices, systems, methods, and processes that allow for such controlled outputs in various ways.

For example, some embodiments describe devices, systems, and methods for producing PHA resins using various feed-forward steps in which desirable compounds are identified and separated from other materials and then conveyed to downstream processes.

Some embodiments may advantageously benefit from digester configurations allowing for desirable materials to be detected and extracted while bulk materials continue to be processed. Examples of such digester configurations are described herein with reference to FIG. 15A and FIG. 15B.

Some embodiments may advantageously benefit from improved material separation and filtration systems and methods. Examples of various separation and filtration systems and methods are described herein with reference to FIG. 8 through FIG. 13. The separation and filtration systems and methods described herein may be used to improve control of processes for producing PHA as well as many other processes.

Some embodiments may advantageously benefit from innovative material analysis systems and methods for evaluating various intermediate materials during a process for producing PHA or other end products. Some specific examples of various material analysis systems and methods are described herein with reference to FIG. 16A-FIG. 16D.

The present disclosure also provides examples of some of the various end products that may be produced using the various devices, systems, methods, and processes described herein. Such end products may include PHAs with specific PHB to PHV ratios, PHAs containing other compounds, and other bioplastics. End products may also include salts of calcium, magnesium, potassium, or other metals. End products may also include component products such as selected volatile fatty acids, essential oils, or other products derivable from the starting materials used.

Bioplastic Production

Producing PHAs or other bioplastics from organic waste products may generally include one or more processes for chemically breaking solid organic waste materials into short-chain fatty acids (otherwise referred to as volatile fatty acids or VFAs), and one or more processes to convert the short-chain fatty acids into PHAs or other bioplastic components.

As used herein, the terms "short-chain fatty acid," "volatile fatty acid," and the abbreviation "VFA" may refer to any fatty acid with an aliphatic tail of one, two, three, four, or five carbon atoms. "Fatty acids" are carboxylic acids with long aliphatic tails (or "chains"), and may be either saturated or unsaturated. "Carboxylic acids" are organic compounds containing a carboxyl group (C(O)OH). Examples of short-chain fatty acids (or VFAs) include formic acid (C1), acetic acid (C2), propionic acid (C3), butyric acid (C4), isobutyric acid (C4), valeric acid (C5), and isovaleric acid (C5).

"Medium-chain fatty acids" may include fatty acids with 6 to 12 carbon atoms, and may include hexanoic acid (also known as caproic acid, having 6 carbon atoms), enanthic acid (7 carbon atoms), caprylic (also known as octanoic acid, having 8 carbon atoms), pelargonic acid (9 carbon atoms), capric acid (10 carbon atoms), and undecylenic acid (11 carbon atoms). "Long-chain fatty acids" are fatty acids with aliphatic tails of 13 to 21 carbons, and "very long chain fatty acids" are fatty acids with aliphatic tails longer than 22 carbons.

FIG. 1A illustrates an example process for producing bioplastics from organic waste products of varying or unknown composition. Process 100 may begin with an input material 102 which may be subjected to a liquefaction process 104. Liquefied material may then be fermented or otherwise processed in a volatile fatty acid (VFA) production process 106, and the fermented input material may then be placed in a solid-to-liquid and/or liquid-to-liquid material separation process 108. The material separation process 108 may include physical or chemical separations of materials or compounds. At least some of the separated material may then be subjected to a bioplastic production process 110. The bioplastic production process 110 may produce an output material 112 directly or an output material 112 may be produced after additional processing.

As used herein, the terms "fluid," "liquid," "fluid mixture," and "liquid mixture" generally refer to substances that may include suspended solids in addition to true liquid state substances. As will be clear from the present disclosure, substances involved in the described processes may undergo various degrees of filtration, and may therefore contain any amounts of large or small solids flowing along with liquid materials. As such, substances or materials referred to as liquids or fluids may include substances that may not necessarily be entirely in a liquid state-of-matter, even after filtration or other separation processes.

In some embodiments, the separation process 108 may be a distillation process, a filtration process, a centrifugation process, a press process, or any other chemical or mechanical separation process. The separation process 108, when a distillation process, may be applied to a specific input material, e.g., citrus culls, to capture essential oils from the input material 102. Other separation processes 108 may be employed in accordance with different aspects of the present disclosure.

For many bioplastics, process 100 may begin with an input material 102 of a singular material such as sugar (e.g., sucrose), canola oil, or other homogenous input material. The input material 102 may be referred to as a "biomass" or a "feedstock" where large quantities of sugar or other carbohydrates are present. As described previously, the cost of sugar, in the quantities employed for process 100, may make the process 100 prohibitively expensive when compared to other input materials. The present disclosure, in an aspect, may employ a wide range of other input materials 102 that may contain short-chain, soluble carbohydrates, such as lactose, maltose, fructose, or other $C_6H_{12}O_6$ derivatives, rather than high-cost input material. The input material 102 encompassed by the present disclosure may include organic waste products, such as food waste, agricultural waste, or other products, such as forestry waste, glycerol, vinegar, or other materials, that may be in solid, liquid, or a mixture of solid and liquid forms. In some cases, the various example bioplastic production processes described herein may be used with input materials of unknown, non-homogenous, or variable compositions.

Depending on the type of the input material 102 that is used in process 100, the input material may be liquefied and/or otherwise processed to facilitate further processing of the input material in later stages of the process 100. For example, if the input material 102 is in solid or semi-solid form, the liquefaction process 104 may convert solid or semi-solid input material 102 into a form that will be more efficiently fermented in the VFA production process 106. If the input material 102 is not of a homogeneous nature, the liquefaction process 104 may also homogenize the input material 102, such that the VFA production process has a uniform effect on the input material 102. In some embodiments, solid input materials may simply be shredded or ground into smaller pieces to allow for mechanical movement of the material through a digester or other process equipment.

The liquefaction process 104 may begin conversion of the input material into short-chain soluble carbohydrates (sugars). This may be done through enzyme and/or bacterial digestion in any suitable digester, such as a batch digester, a series of sequence batch digesters, a plug flow digester, a continuous digester, or any combination of these or other digester types. Further, the liquefaction process 104 may include steps and/or components to aid in the filtration of contaminants and separation of liquids from solids that may occur later in the process 100.

In an aspect of the present disclosure, the input material 102 may also be mixed with additional material to aid in the liquefaction process 104, VFA production process 106, or in other steps or processes used in the overall process 100. As such, in the liquefaction process 104, other materials, such as nutrient enrichments or other additional materials, may be added to the input material or intermediate materials to make the remainder of the process 100 more efficient for the input material 102 being used. Various additives, nutrient enrichment materials, or other inputs may be made to the input material 102, based on the desired output material 112, the chemical composition of the input material 102, the VFA production process 106, the separation process 108, and/or the bioplastic production process 110, or other factors.

The VFA production process 106 may be configured to convert sugars present in the liquefied input material 102 into acids, including VFAs. In various embodiments, the VFA production process 106 may be done by bacterial fermentation, acid phase anaerobic digestion, hydrolysis, or various combinations of these and/or other processes. Certain bacteria, which may be called hydrolytic bacteria may generally be those that perform liquefaction. Acidogenic bacteria may generally be those that form VFAs, and acetogenic bacteria may generally be those that produce acetic acid. These and/or other bacteria may be combined with the liquefied, optionally nutrient added, input material 102 in the VFA production process 106. As the bacteria and sugar-laden input material combine, they may produce carboxylic acids including VFAs. For example, the bacteria may produce acids such as lactic acid, acetic acid, propionic acid, butyric acid, isobutyric acid, valeric acid, isovaleric acid, caproic acid, and other carboxylic acids, other VFAs, or other volatile acids depending on the bacteria added in the VFA production process.

In some cases, desired acidogenic bacteria may include wild-type bacteria, which are naturally occurring and/or not genetically modified bacteria. In some embodiments, desired acidogenic bacteria may include obligate anaerobes of one or more of the following genera: *pseudomonas, bacillus, clostridium, micrococcus*, and *flavobacterium*. Such wild-type acidogenic bacteria may be used to anaerobically digest the material in any of the digester. The use of wild-type bacteria provides the ability to use non-sterilized conditions for the process 200, as well as a cost-effective approach to the use of digesters. Many input materials 102 may also be more efficiently digested using wild-type bacteria than with genetically-modified bacteria.

Desired wild-type acidogenic bacteria, which may be used in some embodiments of the VFA production process 106, may be obtained from any available source and then cultured and encouraged by providing conditions that support the desired bacteria and suppress the activity of undesired bacteria. In some embodiments, desired VFA producing bacteria may generally be mesophilic, preferring moderate temperatures and conditions. For example, desired bacteria may be encouraged by controlling various environmental conditions such as pH, aerobic anaerobic cycling, carbon to nitrogen ratio, feast-famine conditions, cycle timing, flow rates, hydraulic residence time vs. solids residence time, etc. In some embodiments, controlling environmental conditions for encouraging desired VFA-producing bacteria may include maintaining a pH of between about 4 and about 6.5. For example, in various embodiments, the materials processed during the VFA production process may be maintained at a pH of about 4, 4.5, 5, 5.5, 6, or 6.5.

In some embodiments, the VFA production process 106 may include aerobic and/or anaerobic digestion. Anaerobic digestion is a biological process (or a collection of processes) in which microorganisms break down organic material in the absence of oxygen. Aerobic digestion is a biological process (or a collection of processes) in which microorganisms break down organic materials in the presence of oxygen. Certain bacterial processes may thrive or die depending on the quantity of oxygen present. Thus, in some embodiments, the composition of intermediate or output materials may be optimized by controlling the relative amount of aerobic and anaerobic digestion. In some embodiments, aerobic digestion may be substantially or entirely omitted from the VFA production process 106. In various embodiments, the VFA production process 106 may include only anaerobic digestion, only anaerobic digestion and fermentation, or only fermentation.

The anaerobic digestion process, when used as part of the VFA production process 106, may include bacterial hydrolysis of the input material 102. Insoluble organic polymers, such as carbohydrates, that may be present in the input material 102 may be broken down into soluble by-products, such as sugars, that are then available for other bacteria to consume. These other bacteria, sometimes called "acidogenic" bacteria, may then convert the sugars into organic acids and/or volatile acids. These organic and/or volatile acids may then be converted into VFAs such as acetic acid or other carboxylic acids such as lactic acid, as well as other by-products such as ammonia, hydrogen, and carbon dioxide. If desired, methanogenic archaea may then be allowed to convert these gases and acids into methane.

In embodiments in which a VFA production process 106 includes an aerobic digestion process, bacteria and/or other microorganisms may use oxygen from the surrounding environment. Aerobic digestion may mainly produce carbon dioxide and water from input material 102 that is rich in carbon and oxygen. If the input material 102 contains nitrogen, phosphorus, and sulfur, then the aerobic digestion may also produce nitrates, phosphates and/or sulfates.

By controlling the environment, temperature, types of bacteria used, the amount of anaerobic and aerobic digestion, and the amount of bacterial fermentation that is done in the VFA production process 106, the present disclosure may accept a large range of input material 102 and still produce an output material 112 with desired properties in a cost-effective and efficient manner. Such parameters may be controlled by controlling environmental parameters during digestion and fermentation processes, such as temperature, pH, dissolved oxygen concentrations, rates or degrees of mixing (e.g., by agitation, stirring, or otherwise), ammonia: nitrogen ratios, organic acid concentrations, or others.

In the separation process 108, the gaseous products of VFA production process 106 may be removed, and the acid products of VFA production process 106 may be separated. As these acid products are separated, each acid product may be refined, purified, or distilled to obtain one or more acids of desired composition. The present disclosure encompasses at least one, and perhaps several, output slurries or gas flows from the separation process 108, which may be recombined or may be processed separately depending on the composition of a desired output material 112.

In the separation process 108, the various products of the VFA production process 106, e.g., solids, liquids, and gases may be separated from each other. Each of the products, which may be acid products, compost, methane, or other solid, liquid, and/or gaseous products, may then be forwarded to other parts of the process 100 as needed.

Some of the separated materials may then be placed in a bioplastic production process 110. The bioplastic production process 110 may be configured to create polymer chains from the one or more separated products, and may further refine the separated products into various output materials 112 and/or by-products.

The above description with respect to FIG. 1A is an overview of a bioplastic formation process 100. Many variations are possible within this general framework of the process 100. In aspects of the present disclosure, reference is made to the process 100, and which potential portion of the process 100 such variations may occur in. However, the present disclosure is not limited to such portions as discussed herein.

PHA Production

In an aspect of the present disclosure, a desired output material 112 may include a material with a high concentration, which may be a 50% to 90% concentration by dry cell weight of PHA. Although PHA may be produced from particular input materials 102, the present disclosure discusses various systems and processes to produce output materials 112 having a high concentration of PHA from an input material 102 comprising organic waste products. In some cases, a desired output material 112 may include water obtained by separating certain desired output materials 112 from input materials 102 and intermediate materials. Depending on the particular organic waste products used as input material 102, variations on the process 100 may be used to produce output materials 112 having PHA with a desired composition.

For example, and not by way of limitation, a particular input material 102 may be mixed with additional nutrients or other additives to provide the process 100 with a feedstock that can produce the desired output material 112, in this instance, PHA. Further, depending on the type (e.g., aerobic vs. anaerobic, the type of bacteria present, etc.) and/or time spent in the VFA production process 106, separation process 108, and bioplastic production process 110, the amount of nutrients may be increased or decreased. Systems and processes provided in the present disclosure may manage the entire process 100, including the input material 102, to produce desired output materials 112 more efficiently for a given input material 102.

In an aspect of the present disclosure, output materials 112 may include PHA, PHA in combination with cell mass, PHA in combination with cell mass and water, or other materials. Further, output materials 112 may include a material that may be further processed to extract PHA and/or other by-products, either within process 100 or in a separate process.

In one embodiment, the input material 102 may be organic waste products such as agricultural and food waste, and the VFA production process 106 may be primarily an acid-phase anaerobic digestion, which generates VFAs. Further, the acid-phase anaerobic digestion of agricultural and food waste may produce lactic acid, which may also be polymerized into the output material 112 including PHA. If desired, the lactic acid may be separated from the VFAs in the separation process 108. Alternatively, lactic acid may be retained in a mixture with the VFAs, and the lactic acid may be incorporated into the PHA copolymer. The bioplastic production process 110 may then be used to produce a PHA copolymer from lactate monomers, and/or hydroxybutyrate and hydroxyvalerate monomers, as well as other monomers, from the VFAs.

Some of the difficulties in related processes when used to produce PHA are that the process may be designed for a single, homogeneous input material, e.g. sucrose. Related processes typically do not contemplate using various or non-homogeneous input materials to produce a consistent PHA resin due to the difficulties in controlling such a process.

The process 200, in an aspect of the present disclosure, may produce different output materials 112. In some embodiments, output materials 112 produced by a process 200 may include a PHA biopolymer made up of various component copolymers. For example, the output material 112 may comprise a biopolymer containing dry weight quantities of polyhydroxybutyrate (PHB), polyhydroxyvalerate (PHV), and other monomers or materials in desired ratios. Bioplastics made from pure PHB tend to be more stiff and brittle while bioplastics made from pure PHV tend to be more elastic. Therefore, depending on the physical characteristics desired of the final product (e.g., the relative stiffness or elasticity of the material), a desired output material 112 may have particular target quantities of PHB, PHV, and other components. Table 1 provides several examples of PHA monomer compositions by dry weight in various embodiments. The examples of Table 1 are not intended to be exhaustive or limiting to the scope of the present disclosure. Composition quantities listed as "<1%" are intended to include compositions with a measurable quantity of the listed component less than 1%, but greater than zero.

TABLE 1

PHA Dry Weight Monomer Compositions

| % Hydroxy-butyrate | % Hydroxy-valerate | % Lactic acid |
|---|---|---|
| 93% | 6% | 1% |
| 90% | 10% | <1% |
| 78% | 22% | <1% |
| 86% | 13% | 1% |
| 50% | 25% | 25% |
| 50% | 10% | 40% |

In some embodiments, the ratio of PHB to PHV in an output material 112 produced by the process 200 may be related to the ratio of specific VFAs directed to the bioplastic production process 110. For example, when fed pure 100% acetic acid, PHA-producing bacteria in the bioplastic production process 110 may tend to produce nearly 100% PHB. Increasing the quantity of propionic acid and/or other higher-chain VFAs (i.e., VFAs with more carbon atoms than acetic acid, which has two) in addition to acetic acid may tend to produce increasing quantities of PHV in addition to PHB. The presence of other acids in various concentrations may also affect the composition of the bioplastic materials produced.

Therefore in some embodiments, the PHB/PHV ratio of an output material 112 may be controlled by maintaining target concentration ratios of different acids in intermediate materials delivered to the bioplastic production process 110. Further, by separating or not separating some of the acids, such as lactic acid, from the intermediate materials delivered to the bioplastic production process 110, the production of polylactic acid (PLA) can be inhibited or enhanced in the output material 112.

Table 2 provides several example ranges of concentrations of various feedstock acids (expressed as mass percents, otherwise referred to herein as "weight percent" or "wt %") that may be used in various embodiments of process 200. Each column of Table 2 may represent a separate set of target concentration ratio ranges for a feedstock liquid mixture to be delivered to PHA-producing bacteria in order to produce a particular desired output bioplastic product. Each feedstock acid mixture may contain quantities of a plurality of VFAs, and some mixtures may contain quantities of lactic acid. As described herein, wt % of feedstock acids is based on the total weight of carboxylic acids, the total weight of VFAs and lactic acid, or the total weight of VFAs in the feedstock. In one example, when the carboxylic acids in the feedstock consist essentially of VFAs and lactic acid, the wt % of feedstock acids may be based on the total weight of VFAs and lactic acid. In another example, when the carboxylic acids in the feedstock consist essentially of VFAs, the wt % of feedstock acids may be based on the total weight of VFAs. The examples of Table 2 are not intended to be exhaustive or limiting to the scope of the present disclosure.

TABLE 2

Example Feedstock Acid Concentrations (wt %)

| | Mix 1 | Mix 2 | Mix 3 | Mix 4 | Mix 5 |
|---|---|---|---|---|---|
| Acetic Acid | 30%-100% | 80%-100% | 60%-100% | 60%-80% | 75%-80% |
| Propionic Acid | 0%-70% | 0%-20% | 0%-40% | 10%-20% | 20%-25% |
| Lactic cid | 0%-30% | 0%-5% | 0%-10% | 0%-10% | 0%-1% |
| Butyric Acid | 0%-50% | 0%-20% | 0%-40% | 5%-20% | 0%-5% |
| Iso-Butyric Acid | 0-30% | 0%-20% | 0%-40% | 0%-7% | 0%-1% |
| Valeric Acid | 0%-50% | 0%-20% | 0%-40% | 0%-10% | 0%-5% |
| Iso-Valeric Acid | 0%-30% | 0%-20% | 0%-40% | 0%-7% | 0%-5% |
| Hexanoic Acid | 0%-50% | 0%-20% | 0%-40% | 0%-10% | 0%-1% |

Table 3 provides several examples of feedstock acid concentrations (expressed as mass percents, otherwise referred to herein as "weight percent" or "wt %") that may be used in various embodiments of process 200. Each row of Table 3 may represent a separate set of target concentration ratios for a feedstock liquid mixture to be delivered to PHA-producing bacteria in order to produce a particular desired output bioplastic product. The examples of Table 3 are not intended to be exhaustive or limiting to the scope of the present disclosure.

TABLE 3

Example Feedstock Acid Concentrations (wt %)

| Acetic Acid | Propionic Acid | Lactic Acid | Isobutyric Acid | Butyric Acid | Isovaleric Acid | Valeric Acid | Hexanoic Acid |
|---|---|---|---|---|---|---|---|
| 45% | 25% | 1% | 3% | 8% | 1% | 8% | 9% |
| 58% | 32% | 1% | 9% | 0% | 0% | 0% | 0% |
| 78% | 22% | 0% | 0% | 0% | 0% | 0% | 0% |
| 88% | 12% | 0% | 0% | 0% | 0% | 0% | 0% |
| 93% | 7% | 0% | 0% | 0% | 0% | 0% | 0% |

In various embodiments, intermediate materials delivered to a bioplastic production process 110 may have a target concentration of acetic acid of between about 40% and about 99%, between about 40% and about 50%, between about 45% and about 50%, between about 50% and about 55%, between about 55% and about 60%, between about 60% and about 65%, between about 65% and about 70%, between about 70% and about 75%, between about 75% and about 80%, between about 80% and about 85%, between about 85% and about 90%, or between about 90% and about 95%, all of which are expressed as wt %. In any of these embodiments, the balance of the intermediate material delivered to the bioplastic production process 110 may be entirely or substantially made up of propionic acid with up to about 1% lactic acid.

In some embodiments, a target ratio of feedstock acids may be defined simply as a minimum weight percent of acetic acid, the balance of the feedstock acids comprising other VFAs and/or lactic acid. In some embodiments, the minimum weight percent of acetic acid may be 30% to 40%, 40% to 50%, 50% to 60%, 60% to 70%, 70% to 80%, 80% to 90%, or 90% to 100%, the balance of the feedstock acids being substantially made up of VFAs with more than two carbons and/or lactic acid.

In some embodiments, target feedstock mixture concentration ratios may be defined in terms of a sum of a weight percent of acetic acid and a weight percent of propionic acid (or another higher-chain VFA). In some embodiments, a feedstock liquid mixture may have a weight percent concentration of acetic acid+propionic acid of at least 20%, at least 30%, at least 40%, at least 50%, at least 60%, at least 70%, at least 80%, or at least 90%, the balance of the feedstock acids being substantially made up of higher-chain VFAs and/or lactic acid. In some embodiments, a feedstock liquid mixture may have a weight percent concentration of acetic acid+propionic acid of up to 20%, 20% to 40%, 40% to 60%, 60% to 80%, or 80% to 100%, the balance of the feedstock acids (if any) being substantially made up of higher-chain VFAs and/or lactic acid.

In some embodiments, target feedstock mixture concentration ratios may be defined in terms of a ratio of acetic acid to propionic acid, regardless of the quantities of other acids or materials in the feedstock. In some embodiments, a feedstock liquid mixture may have a ratio of wt % of acetic acid to wt % of propionic acid of between about 0.4 and about 13 or more. In some particular embodiments, a feedstock liquid mixture may have a ratio of wt % of acetic acid to wt % of propionic acid of about 3/7, about 29/16, about 9/5, about 3/2, about 39/11, about 22/3, or about 93/7.

In some embodiments, a feedstock liquid may be diluted with water or another solvent to obtain a desired concentration of total VFAs per unit volume of feedstock liquid. For example, if a feedstock liquid contains substantially more VFA mass per unit volume than a desired concentration, a dilution solvent may be added to the feedstock liquid until a desired volumetric concentration is reached. For example, in some embodiments, a feedstock liquid to be delivered to a bioplastic production process may be prepared with a target concentration of total VFAs of between about 10 g/L and about 30 g/L, or between about 15 g/L and about 25 g/L.

Process Variability Based on Input Material

Figure 1B:
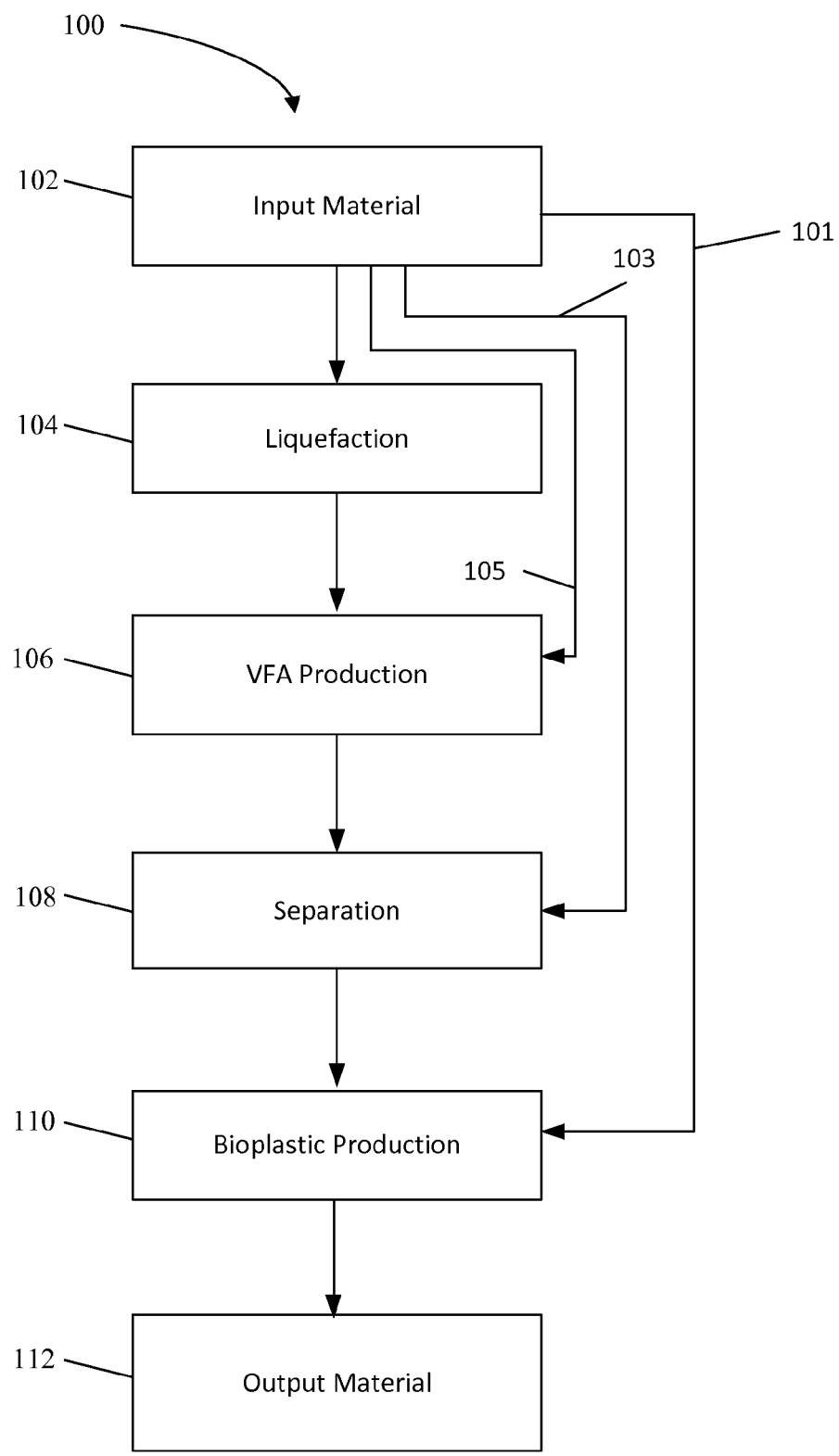
FIG. 1B is a process flow diagram illustrating an embodiment process for producing bioplastics.

FIG. 1B illustrates several variations of the process flow shown in FIG. 1A. In addition to moving materials directly from one step to the next as shown in FIG. 1A, the variations of FIG. 1B provide the ability to advance materials produced in one process directly to a later process while bypassing one or more intermediate processes. Some examples of such variations are described below with reference to FIG. 1B.

Path 101 provides the ability for some or all of an input material 102 to flow directly to the bioplastic production process 110, bypassing the intermediate steps of liquefaction, fermentation, and separation. In such a process flow, some or all of the input material 102 is able to be directly polymerized. Some examples of input materials 102 that may utilize path 101 within process 100 are a pure VFA stream, a methanol stream, or a sugar stream that can be directed toward the bioplastic production process 110 rather than going through the remainder of the processes in the process 100.

Similarly, some input materials 102 may be suitable to bypass the liquefaction process 104 and the VFA production process 106 and be directed toward the separation process 108 via path 103. For example, and not by way of limitation, a mixed liquid stream may only need to be separated (e.g., by separating existing liquids from existing solids) rather than running the input material 102 through unnecessary portions of the process 100. For example, an input material 102 comprising vinegar and oil is already liquefied, and already contains the desired materials, so liquefaction and fermentation may not be used when processing such input materials which would be directed to path 103.

Path 105 may also be used for input materials 102 that can bypass the liquefaction process 104 and may be directed to the VFA production process 106. For example, and not by way of limitation, some input materials 102 may already be soluble, but fermentation may be used to derive the desired output material(s) 112. Such an example may be an input material 102 comprising a solids-free stream of long-chain fatty acids from biodiesel by-products. The long-chain fatty acids may then be processed in the VFA production process 106 to form short-chain fatty acids which may then continue through the rest of the process 100. Another example of an input material 102 that may utilize path 105 is a mixed VFA stream from a compost leachate.

In some embodiments, the input material 102 may substantially comprise a liquid obtained from a composting process. Such a liquid may be referred to as a compost leachate, and may generally contain substantial quantities of long-chain fatty acids in aqueous solution. Such an input material may be sent directly to the VFA production process 106 via path 105. The VFA production process may be configured to convert the long-chain fatty acids into shorter-chain VFAs in desired ratios.

Process Analysis and Feedback Control

Figure 2:
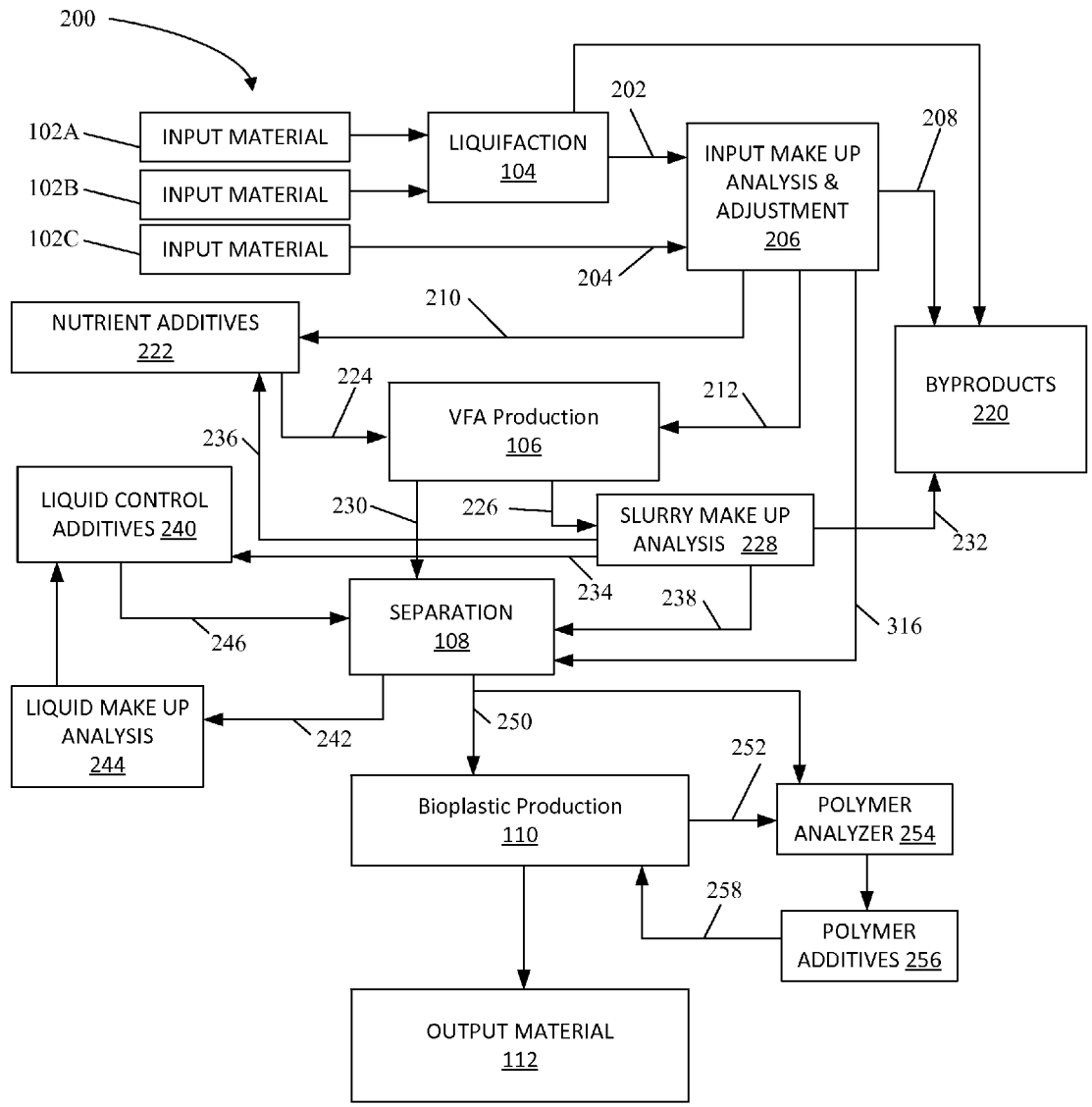
FIG. 2 is a process flow diagram illustrating an embodiment process for producing bioplastics.

FIG. 2 illustrates a detailed example process flow in an aspect of the present disclosure. In some embodiments, the composition or make-up of each intermediate product flowing from one sub-process to another may be monitored, modified, and adjusted. This monitoring and adjustment allows the process 200 to be improved or tailored to a particular input material 102 for production of a desired output product. For example, one or more of the liquefaction process 104, VFA production process 106, separation process 108, and bioplastic production process 110 can be altered, or additional materials can be added to the overall process 200, to produce an output material 112 with a desired composition and/or an output material 112 having specific desired qualities or characteristics.

The process 200 of FIG. 2 contains several sub-processes and modules which are further described elsewhere in the present disclosure. The process 200 may begin by directing one, to three, or more input materials (e.g., 102A, 102B, 102C) into a device for performing a liquefaction process 104 or directly to an input make-up analysis and adjustment module 206 for performing analysis and/or adjustment of the composition or make-up of the input materials 112A, 112B, 112C.

As used herein the term "make-up" may refer to any qualitative or quantitative description of one or more input materials, intermediate products, output products or any other material to be manipulated or produced during processing in any of the systems or methods herein. For example, make-up may include a material's chemical composition, a ratio of solids to liquids, pH, temperature, viscosity, a presence or concentration of one or more desired or undesired components, ratios describing relative concentrations of one or more components, etc.

The make-up of input materials may be evaluated and/or adjusted by the input make-up analysis and adjustment module 206. Depending on the results of the analysis, some or all of the input materials may be diverted to other modules for processing and/or to be mixed with other materials for improved processing. For example, if the input make-up module 206 determines that the input material should be supplemented with additives, some or all of the input material may be directed via path 210 from the input make-up module 206 to a nutrient additive module 222. If the input make-up module 206 determines that the input material is ready for the VFA production process 106, then some or all of the input material may be directed, as VFA production input materials 212 to a VFA production process module configured to perform a VFA production process 106 which may include fermentation, acid phase digestion, and/or other VFA production process.

In various embodiments, the input make-up module 206 may comprise a combination of conduits, valves, electromechanical actuators, electronic controllers, processors, data storage devices, and analytical devices (e.g., microscopes, cameras, spectrophotometers, pH testers, electrochemical test equipment, etc.) or other devices and/or software configured to characterize a make-up of sampled materials.

The nutrient additive module 222 may comprise any suitable structural components capable of performing the role of delivering measured quantities of one or more additives to the input material or to intermediate materials. For example, the nutrient additive module 222 may comprise a controller that includes a processor and digital storage device containing instructions to perform various processes or tasks. The nutrient additive module 222 may also comprise one or more dosing pumps, conduits, pipes, hoses, valves, electromechanical actuators, configured to transport one or more additives from an additive reservoir (e.g., a tank, container, bottle, etc.) to process equipment containing an input material or intermediate material to be modified by the additive.

Dosing pumps in any of the various embodiments herein may generally include any type of pump, conveyor, or other device capable of delivering precise controlled quantities of a liquid, solid/liquid fluid mixture, powder, or solid material from a reservoir to a desired location. For example, dosing pumps (also referred to as metering pumps) may include peristaltic pumps, diaphragm pumps, piston pumps, gear pumps, syringe pumps, or others.

In various embodiments, nutrient additive reservoirs within the nutrient additive module 222 may include nutrients and other substances that may be delivered to components performing the VFA production process 106 so as to modify or adjust the process in a desired manner. Nutrient additives may include supplemental nutrients such as nitrogen source materials (e.g., ammonia or other nitrogen-rich substances), liquids containing bacteria cultures, dilution liquids (e.g., water), liquids containing a known concentration of a single VFA or of multiple VFAs or other carboxylic acids (e.g., acetic acid, propionic acid, lactic acid, etc.), phosphorus, potassium sources, pH adjustment liquids (e.g. acids or bases of known pH and concentration).

If the input make-up analysis and adjustment module 206 determines that some of the input material has an appropriate make-up, that portion of the input material may be directed to a module for performing separation 108 via path 316 and/or directly to a bioplastic production process step 110 bypassing the separation step 108.

Materials exiting the fermentation/digestion process 106 may be directed to various downstream points depending on the nature of the material and other factors. For example, liquid/solid slurry expected to be rich in VFAs produced during fermentation and/or digestion (generally referred to herein as the "digestate") may be directed via path 226 to a slurry make-up analysis module 228.

In various embodiments, the slurry make-up analysis module 228 may comprise a combination of conduits, valves, electromechanical actuators, electronic controllers, processors, data storage devices, and analytical devices (e.g., microscopes, cameras, spectrophotometers, pH testers, electrochemical test equipment, etc.) or other devices and/or software configured to characterize a make-up of sampled materials.

The slurry make-up analysis module 228 may analyze the make-up of the digestate to determine what next steps to take. The slurry make-up analysis module 228 may also include solid/liquid separation components and/or filtration components configured to separate some materials from others. Thus, in some cases, the slurry analysis module 228 may separate the digestate into separate materials, some of which may be directed to a liquid control additives module 240. Some material may also be directed from the slurry make-up analysis module 228 to a repository for by-products 230.

The slurry make-up analysis module 228 may also identify (and optionally separate) some materials having a make-up suitable for production of a biopolymer. Such materials may be directed to a separation step 108 or directly to a bioplastic production process step 110. In some embodiments, the slurry make-up analysis module may be configured to identify and isolate liquids rich in specific VFAs.

In some cases, some material exiting the separation step 108 may be analyzed by a liquid make-up analysis module 244 which may instruct a liquid control additives module 240 to mix the material with liquid additives.

In various embodiments, the liquid make-up analysis module 244 may comprise a combination of conduits, valves, electromechanical actuators, electronic controllers, processors, data storage devices, and analytical devices (e.g., microscopes, cameras, spectrophotometers, pH testers, electrochemical test equipment, etc.) or other devices and/or software configured to characterize a make-up of sampled materials.

The liquid control additives module 240 may comprise any suitable structural components capable of performing the role of delivering measured quantities of one or more additives to the input material or to intermediate materials. For example, the liquid control additives module 240 may comprise a controller that may contain a processor and digital storage device containing instructions to perform various processes or tasks. The liquid control additives module 240 may also comprise one or more dosing pumps, conduits, pipes, hoses, valves, electromechanical actuators, configured to transport one or more additives from an additive reservoir (e.g., a tank, container, bottle, etc.) to process equipment containing a input material or intermediate material to be modified by the additive.

Dosing pumps in any of the various embodiment herein may generally include any type of pump, conveyor, or other device capable of delivering precise controlled quantities of a liquid, solid/liquid fluid mixture, powder, or solid material from a reservoir to a desired location. For example, dosing pumps (also referred to as metering pumps) may include peristaltic pumps, diaphragm pumps, piston pumps, gear pumps, syringe pumps, or others.

In various embodiments, liquid control additive reservoirs within the liquid control additives module 240 may include various substances that may be delivered to components performing a separation process 108 or to intermediate materials 250 to be delivered to the bioplastic production process 110 so as to modify or adjust the process in a desired manner. Liquid control additives may include supplemental nutrients such as nitrogen source materials (e.g., ammonia or other nitrogen-rich substances), liquids containing bacteria cultures, dilution liquids (e.g., water), liquids containing a known concentration of a single VFA or of multiple VFAs or other carboxylic acids (e.g., acetic acid, propionic acid, lactic acid, etc.), phosphorus, potassium sources, pH adjustment liquids (e.g. acids or bases of known pH and concentration).

Materials processed in the bioplastic production process 110 may be evaluated by a polymer analyzer 254 which may evaluate a make-up of polymerized or partially polymerized materials to determine whether additional polymerization or other bioplastic production processing, polymer additives or other processing may be needed to obtain a desired output material 112.

As used herein, the term "analyzer" may include any combination of devices configured to assess a make-up, composition, or concentration of a liquid, solid, or liquid/solid mixture material. In various embodiments, analyzers described herein, including the polymer analyzer 254, may comprise any combination of conduits, valves, electromechanical actuators, electronic controllers, processors, data storage devices, and analytical devices (e.g., microscopes, cameras, spectrophotometers, gas chromatographs, liquid chromatographs, pH testers, electrochemical test equipment, etc.) or other devices and/or software configured to characterize a make-up of sampled materials. In some embodiments, analyzers may assess a concentration of one or more material constituents, and may convert between various measures of such a concentration. For example, an analyzer may assess a molar concentration of one or more constituents (such as specific VFAs or all VFAs in the sample), and may convert the assessed molar concentration values to weight percent values. Similarly, analyzers may convert between mole concentrations, weight percents, molar concentrations, molality, parts per million, or any other measure of a quantity of a material constituent within a sample of a material. Various examples of make-up modules described herein may be or may contain one or more analyzers.

The polymer additives module 256 may comprise any suitable structural components capable of performing the role of delivering measured quantities of one or more additives to the input material or to intermediate materials. For example, the polymer additives module 256 may comprise a controller that may contain a processor and digital storage device containing instructions to perform various processes or tasks. The polymer additives module 256 may also comprise one or more dosing pumps, conduits, pipes, hoses, valves, electromechanical actuators, configured to transport one or more additives from an additive reservoir (e.g., a tank, container, bottle, etc.) to process equipment containing an input material or intermediate material to be modified by the additive.

Dosing pumps in any of the various embodiments herein may generally include any type of pump, conveyor, or other device capable of delivering precise controlled quantities of a liquid, solid/liquid fluid mixture, powder, or solid material from a reservoir to a desired location. For example, dosing pumps (also referred to as metering pumps) may include peristaltic pumps, diaphragm pumps, piston pumps, gear pumps, syringe pumps, or others.

In various embodiments, polymer additive reservoirs within the polymer additives module 256 may include various substances that may be delivered to components performing a bioplastic production process 110 so as to modify or adjust the process in a desired manner. Polymer additives may include supplemental nutrients such as nitrogen source materials (e.g., ammonia or other nitrogen-rich substances), liquids containing bacteria cultures, dilution liquids (e.g., water), liquids containing a known concentration of a single VFA or of multiple VFAs or other carboxylic acids (e.g., acetic acid, propionic acid, lactic acid, etc.), phosphorus, potassium sources, pH adjustment liquids (e.g. acids or bases of known pH and concentration), specific PHA copolymers (e.g., PHB or PHV), specific VFAs, other polymers or copolymers, etc.

If the polymer analyzer determines that polymer additives are needed to obtain a desired output material, a polymer additive module 256 may deliver additives to a chamber in which the bioplastic production process 106 is being performed. The additives delivered by the polymer additive module 256 may be selected based on the results of the analysis performed by the polymer analyzer 254. For example, if the polymer analyzer 254 determines that the fluid mixture in the bioplastic production process container has a composition or ratio of specified VFAs outside of a target range, then the polymer analyzer 254 may direct the polymer additives module 256 to add a quantity of a concentrated VFA liquid to increase the quantity of one or more VFAs until a ratio of VFAs is within a target range.

Once a desired output material 112 is produced, the material may be directed from the bioplastic production process 110 to a repository for the output material 112.

In some cases, all or portions of process 200 may be used to separate polar organic acids from solid materials, water or other liquids, or from other organic acids in solution. Further, the acids and/or other liquids may also be separated from solids, various organic and inorganic compounds, other polar organic acids, salts, and other constituents. Such separations may take place during the liquefaction process 104, the VFA production process 106, or the separation process 108, depending on the input material 102 and various factors employed during process 200.

As used herein, the terms "polar organic acid," "polar organic molecule," and "polar organic compound" may refer to organic chemical compounds with an electric dipole or multipole moment. Similarly, the terms "polar molecule," and "polar compound" may refer to chemical compounds (both organic and inorganic) with an electric dipole or multipole moment.

In some cases, a consistent desired output material may be obtained by controlling each of the sub-processes 104-110 in the process 200 for each individual input material 102, as well as each "batch" of the input material 102 that is placed into the process 200. Further, as different input materials 102 and different desired output materials 112 are entered into or extracted from the process 200, the process controls and monitoring allow for a wider range of materials to be used in, and produced by, the process 200. Further, a single line of equipment may be used to perform process 200 and still accept various input materials 102 and produce various output materials 112.

As shown in FIG. 2, different types of input materials 102, shown as input materials 102A, 102B, 102C, may be used as feedstocks for the process 200. Further, depending on the desired process 200, one or more of the input materials 102A, 102B, and/or 102C may be pre-processed prior to the process 200, and more than one of the input materials 102A, 102B, and/or 102C may be used in any combination as inputs to the process 200. The present disclosure is not limited to three input materials 102A, 102B, and 102C; any number of input materials may be used without departing from the scope of the present disclosure.

Depending on the composition of the input material, the process flow may use the liquefaction process 104 to provide a uniform material 202. Otherwise, the input material 102A, 102B, and/or 102C may flow directly as material 204 to a make-up module 206. Liquefaction process 104 may use a mechanical homogenization process, a macerator, or other mechanical, electrical, or biological device or process to provide desired characteristics within the input material 102A-102C. Further, the liquefaction process 104 may be used to provide a more uniform feedstock to the VFA production process 106.

Figure 3:
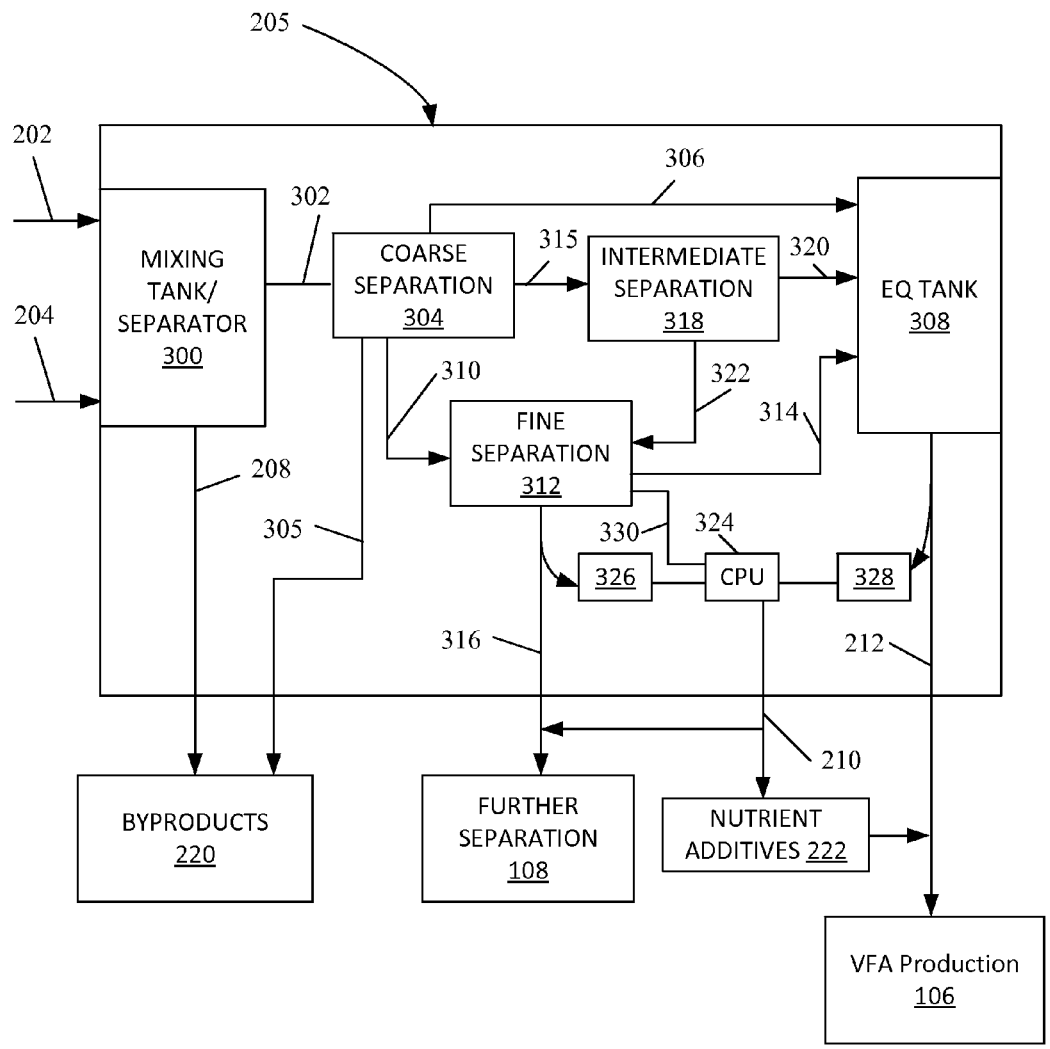
FIG. 3 is a schematic block diagram illustrating an example of a make-up module for analyzing materials in a bioplastic production process.

An example of a make-up analysis and adjustment module 205 (otherwise referred to as a "make-up module") in accordance with an aspect of the present disclosure is shown in more detail in FIG. 3. Any of the various analyzers and make-up modules shown and described herein may include some or all of the features of the make-up module 205 illustrated in FIG. 3. For example, any or all of the input make-up analysis and adjustment module 206, the slurry make-up analysis module 228, the liquid make-up analysis module 244, the polymer analyzer 254, or others may include some or all of the features of the make-up module 205 of FIG. 3.

As shown in FIG. 3, the various materials 202 and/or 204 (or others) directed into the make-up module 205 may be initially placed in a mixing tank 300. The mixing tank 300 may homogenize the materials 202 and/or 204 if needed into a single mixed material 302, such as by agitation with an agitator, stirrer, or other mixing mechanisms. Further, the mixing tank 300 may separate out a flow 208 containing inert materials, such as metals, plastics, and other materials that may not be converted into the output material 112 when subjected to the process 200. The flow 208 may be sent from the make-up module 205 to a by-products container 220 for further separation and/or disposal. In some embodiments, the make-up module 205 may comprise material sampling and analysis components such as a processor 324 and one or more samplers 326, 328.

In some aspects, the make-up module 205 may include a processor 324, which may be coupled to sampler 326 and/or sampler 328. The samplers 326 and 328 may comprise material sampling conduits and one or more composition analysis devices. The sampling conduits may be configured to deliver a sample of material to a composition analysis device. Depending on the location of the make-up module 205 within the system, the make-up module 205 may be configured to draw samples of intermediate materials for analysis and/or adjustment. For example, make-up modules 205 may be configured to draw samples of fine separation outputs 316, VFA production input materials 212, liquified material 202, VFA production outputs 230 or 226, separation outputs 242 or 250, bioplastic production outputs 252 or others. The sampler composition analysis devices may comprise one or more microscopes, cameras, spectrophotometers, pH testers, electrochemical test equipment, or other devices and/or software configured to characterize a make-up of the sampled materials.

For example, in some embodiments the samplers 326, 328 (e.g., via one or more composition analysis devices) may be configured to compare a sample of an intermediate material (e.g., liquefied material 202, VFA production outputs 230 or 226, separation outputs 250, polymer stream outputs 252 or others) to a known sample of material or to data obtained by analyzing a known sample of material. Through visual, chemical, or structural comparison of the output 250 and/or the polymer stream 252, the polymer make-up module may alter the bioplastic production process 110, or other portions of the process 200, to more closely match the output 250 and/or the polymer stream 252 to a desired material. This comparison may be done in real-time to control the process 200 during operations.

Sampler 326 may be configured to monitor the liquid 316 and to sample the liquid 316, to determine if the liquid 316 is ready for a subsequent process. Further, the sampler 326, which may provide information to the processor 324, may aid in controlling the sub-processes within the process 200, such as by changing parameters of one or more sub-processes. For example, and not by way of limitation, the sampler 326 may determine that the liquid 316 has a concentration of one or more VFAs below a desired threshold. The processor 324 may then vary the time, heat, pressure, and other factors used in the separation process 108 to produce a desired output from the separation process 108 containing a desired concentration of one or more VFAs.

In some embodiments, the make-up module 205 may comprise substantially only the material sampling and analysis components such as one or more processors 324, data storage devices, and one or more samplers 326, 328 which may include material analysis devices.

The make-up module 206, either alone or in combination with other apparatuses, devices, or flow through the process 200, may act as a nutrient or material make-up management system for the process 200. Depending on the homogeneity of the input material 102, the amount of VFAs or other materials present in the input material or any of the by-products or subsequent flows through the process 200, or other factors, the make-up module 206 may add nutrients to the input material 102 or alter the flow of the input material 102 through the process 200.

In various embodiments, control signals produced by the make-up module 206 to other systems executing the process 200 may allow for the use of different input materials 102 in the process 200, and may allow for different output materials 112 to be made using the same devices or system embodying the process 200. By measuring different characteristics of the input material 102 and intermediate materials and the processing of the input material at various stages of the process 200, and controlling the time, temperature, and other factors that are used during the process 200, the make-up module 206, either alone or in combination with other apparatuses or devices, may increase the efficiency and/or increase the diversity of input materials 102/output materials 112 that the process 200 may produce.

The make-up module 206, although described herein with respect to the VFA production process 106, may also provide inputs to intermediate materials just prior to the bioplastic production process 110 or at other stages of the process 200 as described in various examples herein.

From the mixing tank 300, mixed material 302 may be placed into a coarse separation device 304 configured to separate the mixed material 302 by density, weight, size, or other properties or characteristics. The first separation device 304 may comprise a centrifugal separator (e.g., a centrifuge, a cyclonic separator, etc.), a filter, a belt filter, a press or other coarse separation device.

There may be some output materials 305 from the coarse separation device 304 that may contain little or no value to the primary production process. Such output materials 305 may include juices produced during citrus rot processing, as phenols in walnut hull processing, heavy concentrations of lead or other materials, or other materials not desirable in the VFA production process 106. Such undesired output materials 305 may be removed from the process 200 at this point by directing them to the by-products container 220.

Other output materials 306 from the coarse separation 304 may be directed to an equalization tank 308, as the output materials 306 may approximate or already be a desired output material of the make-up module 206. Some output materials 310, such as a peel and pulp fraction, may still be liquids mixed with some denser or larger solid or more viscous fluid material, and may be passed through a second separation step 312 to separate the liquid from the denser or larger material such that the denser or larger materials form an output 314 that can also be sent to the equalization tank 308. The equalization tank 308, as well as the rest of the make-up module 206, may be environmentally controlled in temperature, pressure, solids content, humidity, or other factors, to increase the ability of the process 200 to produce the lipids, sugars, and other organic materials that will be used to produce desired output products from mixed material 302 that will be forwarded to the digester and/or forwarded to other portions of process 200.

Some liquid material 316 from the fine separation step 312 may also be a desired output of the make-up module 206. The material that forms the output 316 may be sent to a further separation process 108. The fine separation step 312 may comprise a centrifugal separator, a filter, a press or other fine separation devices.

Still other material 315 from the coarse separation step 304 may need to be further processed in an intermediate separation step 318 to remove additional solids 320 that can be further processed in the equalization ("EQ") tank 308. After the intermediate separation process 318, the liquid output 322 material may also be further processed in the fine separation step 312. The intermediate separation step 318 may comprise a centrifugal separator, a filter, a particle filter, membrane filter, electromagnetic filter, a belt filter, a press or other coarse separation devices.

The fine separation 312 may allow the process 200, and the make-up module 206, to accept multiple and varied feedstocks (materials 202 and 204) into the process 200. By controlling the size of particles that are separated by the fine separation 312, contaminants to the process 200 may be strained out, and various different liquids may be separated, that contain different by-products that may be usable within the process 200. Further, the by-products can be directed to different places within the process 200, or may be transferred to different machines and/or different processes, because of the variability allowed through the fine separation 312.

For example, and not by way of limitation, the fine separation 312 may be used to filter different sizes of acids, some of which have longer chains, for use in different products. Some short-chain fatty acids may be used in one process to make an output material such as PHA. Other acids, having longer chains, may be separated using the fine separation 312 for use in biodiesel and other biofuel production. Further, the fine separation 312 may be electrically and/or mechanically changed within the process 200 to perform both of these separations, as well as additional separations, as desired. In one example, fine separation 312 may include a centrifugal separator, a filter, a particle filter, a membrane filter, an electromagnetic filter, a belt filter, a press or other fine separation devices.

The equalization tank 308 may also be used to provide a proper balance of solids to liquids to the VFA production process 106. For example, depending on the input material 102 and VFA production process 106, a desired target percentage of solids may produce a desired output material 112 more efficiently than other percentages of solids when placed in the VFA production process 106. The desired target percentage of solids may be between about 2% and about 65%, between about 4% and about 45%, between about 2% and about 10%, between about 10% and about 20%, between about 30% and about 40%, between about 40% and about 50%, or between about 50% and about 65%, all of which are expressed as wt %.

Figure 4:
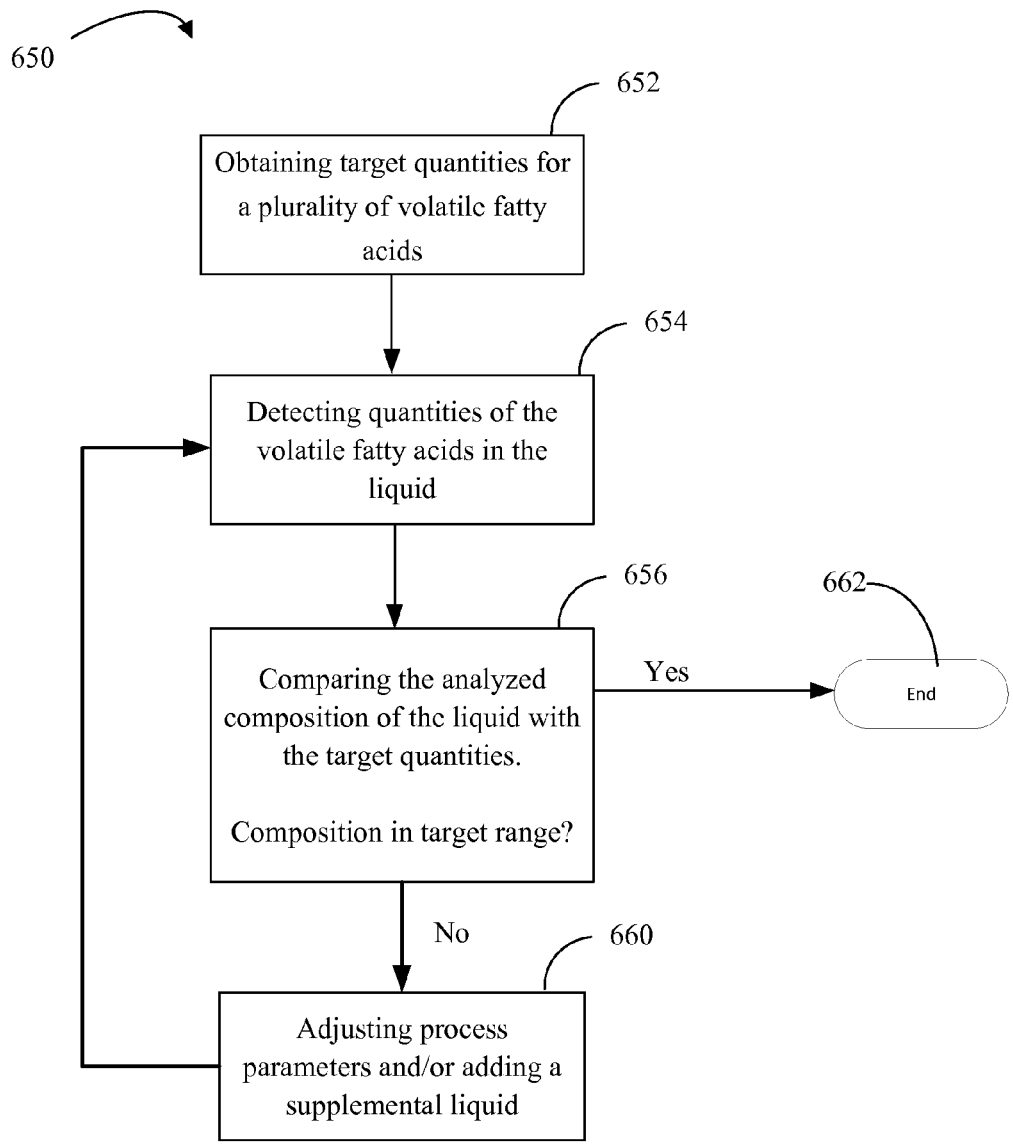
FIG. 4 is a schematic process flow diagram illustrating a process for obtaining a VFA solution containing target quantities of specified VFAs.

FIG. 4 illustrates an example process 650 for obtaining a desired intermediate product composition to be delivered to a bioplastic production process 110. The process 650 may be executed by the processor 324 or by another processor with access to a data storage device. The desired intermediate product may be a liquid containing VFAs in desired quantities. In 652 of the illustrated process 650, the processor may obtain target quantities for a plurality of VFAs. In various embodiments, the target quantities may be in relative or absolute concentration terms.

The actual (absolute or relative) quantities of each of the specified VFAs may be detected by a make-up analyzer at 654, and the detected quantities may be compared with the target quantities at 656. If all of the compositions are not within a desired range of the target quantities, the process may proceed to 660 and may adjust one or more process parameters and/or operate an electromechanical device to add a supplemental liquid to the measured liquid (which in some embodiments may contain a highly concentrated VFA). The detecting (654), comparing (656), and adjusting 660 processes may be repeated as many times as needed until the compositions are within a desired range of the targets, at which point the process may end at 662.

Further, the processor 324 may accept data or input information from the sampler 328, which may monitor the characteristics of the materials in the equalization tank 308. In a similar fashion, the processor 324 may alter the parameters of the VFA production process 106 based on the analysis provided by the sampler 328. The processor 324 may also receive input signals from other parts of the process 200, such as analysis of the VFA production process 106 output, separation process 108, etc., and provide output signals 210 to other parts of the process 200, such as signals to add materials to the process 200 from a nutrient additive bank 222, increase or decrease fermentation time, etc., to make the process 200 more efficient for the flows of materials 202 and 204.

The processor 324 may also send signals 330 to control the filter 312, or to control other portions of the make-up module 206, within the scope of the present disclosure. The nutrient additive bank 222 may include acetic acid, propionic acid, isobutyric acid, butyric acid, isovaleric acid, valeric acid, lactic acid, ammonia, phosphorus, various types of bacteria, etc., which may be added to materials at various points in the process 200 as desired.

As shown in FIG. 3, the make-up module 206 may be configured to separate the flows of input materials 202 and/or 204 into various components. From the mixing tank 300, by-products and/or inert materials may be separated from the overall feedstock. The coarse separation 304, intermediate separation 318, and fine separation 312 steps may remove solids from liquids in the feedstock. Liquids may be passed to the separation process 108 and/or to the VFA production process 106, and solids may be sent to the equalization tank 308. Nutrients may be added to the equalization tank 308 to begin the breakdown of the solid materials if desired. Nutrients or other additives may also be added to liquids prior to the VFA production process 106. Further, the samplers 326 and/or 328 may be used to sample the liquids and solids, to evaluate the materials being passed to subsequent portions of the process 200. Additives, such as nitrogen, phosphorus, potassium, or other micronutrients may be added to the liquid 316 flow, or the VFA production input material flow 212, to increase the efficiency of the overall process 200 and/or to produce a desired output material 112.

Returning to FIG. 2, flow 208 may be passed to the by-products container 220 from the make-up module 206. As discussed above, the by-products container 220 may receive other plastics, metals, or other products that may deleteriously affect the process 200. Output signals 210 based on the make-up module 206 may be sent to the nutrient additive bank 222, such that selected nutrients and amounts may be added to the VFA production process 106. The VFA production input material 212 flowing from the equalization tank 308 may be added to the VFA production process 106.

Fermentation/Digestion Process

Figure 5:
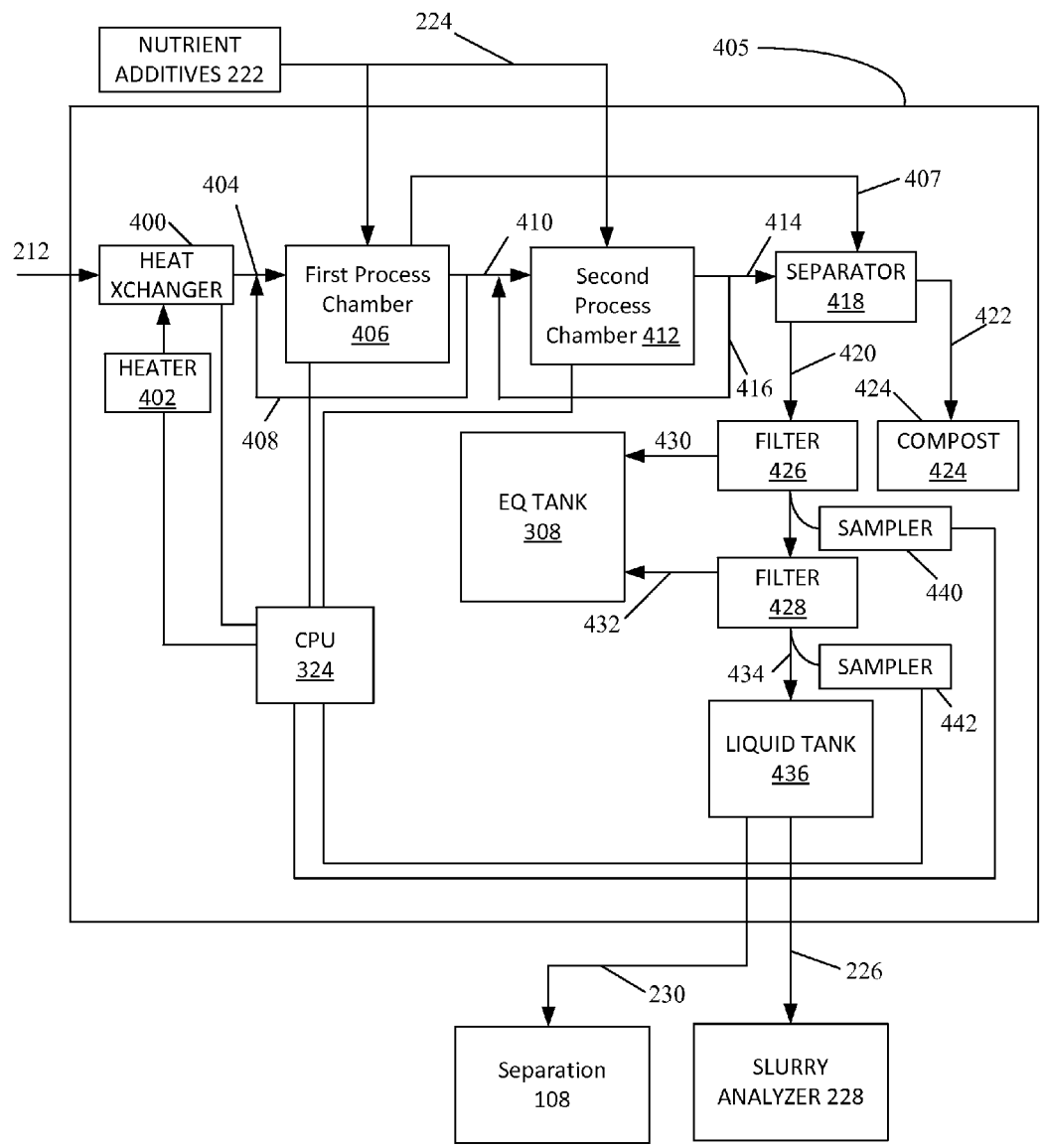
FIG. 5 is a schematic process flow diagram illustrating an example VFA production process.

In an aspect of the present disclosure, the VFA production process 106 may be performed by a WA production subsystem 405 such as that illustrated in the block diagram of FIG. 5. Although a VFA production process 106 may include biological processes, such as yeast acting upon sugars to produce alcohol, in some aspects acid-phase anaerobic digestion of sugars present in the feedstock may be performed.

The VFA production input material 212 flowing into the VFA production subsystem 405 may initially be placed in a heat exchanger 400, which may receive heat from an electric, gas, waste heat, or other type of heater 402. In various embodiments, the heat exchanger 400 may be joined to a heat sink such as ambient air, ambient water, a refrigeration system or other low-temperature source that may be used to remove heat from the VFA production input material 212 in addition to or in place of the heater 402.

Once the material has reached a desired temperature range, the material 404 exiting the heat exchanger 400 may be placed in a first processing chamber 406, which may be an acid-phase digester, hydrolysis tank, fermenter, polishing tank, or other container. The first processing chamber 406 may have a recirculating output 408 that may be fed to the input of the first processing chamber 406. In some embodiments, some or all materials exiting the first processing chamber may be recirculated into the first processing chamber input based on an indication that material exiting first processing chamber may be efficiently fermented further. Such an indication may be obtained based on a measurement of a quantity of nitrogen, phosphorus or solids remaining in the digested materials, or other measurements.

The first processing chamber 406 may anaerobically digest the material 410 into soluble carboxylic acids, including VFAs. Because the material 404 may not have included a desired chemical composition, the processor 324 may also send signals to the nutrient additive bank 222, or to an operator, with instructions to add specific amounts 224 (FIG. 2) of certain nutrients, certain types of bacteria, or other additives from the nutrient additive bank 222 to the processing chamber 406.

If desired, the material 410 from the processing chamber 406 may be placed into a second processing chamber 412 or additional processing chambers. Having multiple processing chambers (e.g., acid-phase digesters or others) may allow the process 200 to employ different types of bacteria during the VFA production process 106. Multiple processing chambers may also allow the VFA production process 106 to produce different types of VFAs, or to obtain additional material 414 to be used in the output material 112 production.

The processing chamber 412 may also have a recirculating output 416 that is fed to the input of the processing chamber 412. As with the processing chamber 406, because the material 410 may not have included a desired chemical composition, the processor 324 may also send signals to the nutrient additive bank 222, or to an operator, with instructions to add specific amounts 224 (FIG. 2) of certain nutrients, different types of bacteria, etc., from the nutrient additive bank 222 to the processing chamber 412. If the processing chamber 406 is able to complete the processing of the material 404, the processing chamber 406 may send the digested material to the separator 418 directly as shown in path 407, thereby bypassing second processing chamber 412 (if present).

Each of the processing chambers 406 and 412 may use different types of processing to digest the materials into soluble acids. Each of the processing chambers may use batch flow processing, sequential batch processing, continuous processing, or plug flow processing.

Further, each of the processing chambers 406 and 412 may use different types of bacteria, or may use different types of bacteria within one of the processing chambers. For example, desired acidogenic bacteria may include obligate anaerobes of one or more of the following genera: *pseudomonas, bacillus, clostridium, micrococcus,* or *flavobacterium*. In some embodiments, desired acetogenic bacteria may include *clostridium aceticum*.

The material 414 that is output from the processing chamber 412 may be sent to a separator 418, where liquids 420 and solids 422 are separated. The separator 418 may comprise any suitable combination of solid/liquid separation devices such as a press, one or more filters, a centrifuge, or others. The solids 422 may be used as compost 424, or may be used elsewhere in the process 200, depending on the solids 422 produced at this point of the process 200.

The liquids 420 may then be filtered through one or more filters such as 426 and/or filter 428. The filters 426 and 428 may provide different levels of filtration for the liquids 420. For example, and not by way of limitation, the filter 426 may be an ultrafiltration system, while the filter 428 may be a nanofiltration system. Either or both of filters 426 and 428 may be any other filter such as the example filtration systems described elsewhere herein. Solids 430 and 432 filtered out of the liquids 420 may be sent to the equalization tank 308 or to the compost 424, as desired.

The liquids 434, after filtering, may be sent to a tank 436 for holding the liquids 434, or may be sent to slurry make-up module 228, or may be sent directly to separation process 108.

The liquids 434, as well as the liquid 420 and any other filtered liquid in the VFA production process 106, may contain VFAs. The filters 426 and 428, as well as the press 418, provide various opportunities to separate the solids in material 414 from the liquids 420 and 434 within the VFA production process 106. Each of these liquids 420 and 434 (and any other liquid containing VFAs) may be separated, either with filters (such as 426 and/or 428 or others), or other separation techniques, to isolate each of the VFAs as desired.

In some embodiments, a desired liquid stream that includes several VFAs in various desired concentrations or ratios may be created. Such a desired liquid stream may be beneficial in creating an output material 112 made up of specific polymers created from the various VFAs in such concentrations. By changing the acids present during the process 200, the output material 112 may be created having desired characteristics or different characteristics based on the presence, absence, concentration, or other characteristics of one or more specific acids.

To control the presence, absence, concentration, or other characteristics of one or more liquids containing one or more specific acids, the nutrient additive bank 222 may be employed to provide the processing chamber 406 and/or 412, or any intermediate liquid stream with ingredients that adjust the VFA concentrations. The samplers 440 and 442, which may be coupled to the processor 324 or another processor within the VFA production process 106, may assist in controlling the VFA concentrations in the liquids 434 and 420, and thus controlling the acid concentrations in the outputs 226 and 230 from the VFA production process 106.

The solids separated from the processing chamber 406 and/or 412 may still contain useable material that can be used to produce methane or other useful products. Such solids may be processed either within the process 200, or in another process, such as in a methane phase digester to produce a methane-rich biogas.

The output of the bioplastic production process 110 may include the desired output material 112. The output material 112 may also be analyzed (e.g., using any suitable analyzer, including those described herein) to determine if other characteristics of the process 200 may be changed to increase the efficiency of producing the desired output material 112. Further, information obtained from the analysis of the input material 102, about the automated and/or manual changes made to the process 200, and about the chemical and structural properties of the output material 112, may all be stored and/or recorded such that future processes 200 may be tailored using the changes made to the process 200 for a particular batch of input material 102.

Process Example

An example of a process for producing a desired PHA bioplastic from a compost leachate input material will now be described with reference to FIG. 5. Compost leachate is a VFA-rich liquid that drains off of compost piles in industrial composting. This liquid may contain a wide range of VFAs and other carbon sources (i.e., carbon-containing compounds that may be consumed by PHA-producing bacteria). The compost leachate material may be collected and placed into a settling tank to remove particulate matter, which may then be placed back in a composter to further break down. Similar VFA-rich liquids may be obtained using a digester such as those described in this disclosure, or other digesters. An example of a mixture of VFAs in a leachate obtained from a compost row is provided in Table 4 below.

TABLE 4

Example Composition of Compost Leachate

| VFA | Quantity (g/L) | Quantity (mass %) |
|---|---|---|
| Acetic | 7.2 | 48.0 |
| Propionic | 2.5 | 16.0 |
| Isobutyric | 0.3 | 2.0 |
| Butyric | 2.8 | 19.0 |
| Isovaleric | 0.3 | 2.0 |
| Valeric | 1.8 | 12.0 |

The following example is described with reference to several "tanks" in which various processes may be performed. The term "tank" is used broadly to refer to any suitable vessel in which a described process may be performed. The various "tanks" described herein may also include additional processing equipment such as pumps, valves, electromechanical actuators, control systems, conduits, pipes, agitators, or any other device suitable for performing one or more of the process steps described. Therefore, to the extent that the following example refers to the tanks performing various functions, the functions may be performed manually (e.g., by manually operated controls) or automatically (e.g., by electromechanical control driven by an electronic controller) by control systems and devices coupled to the tanks and associated processing equipment.

Figure 6:
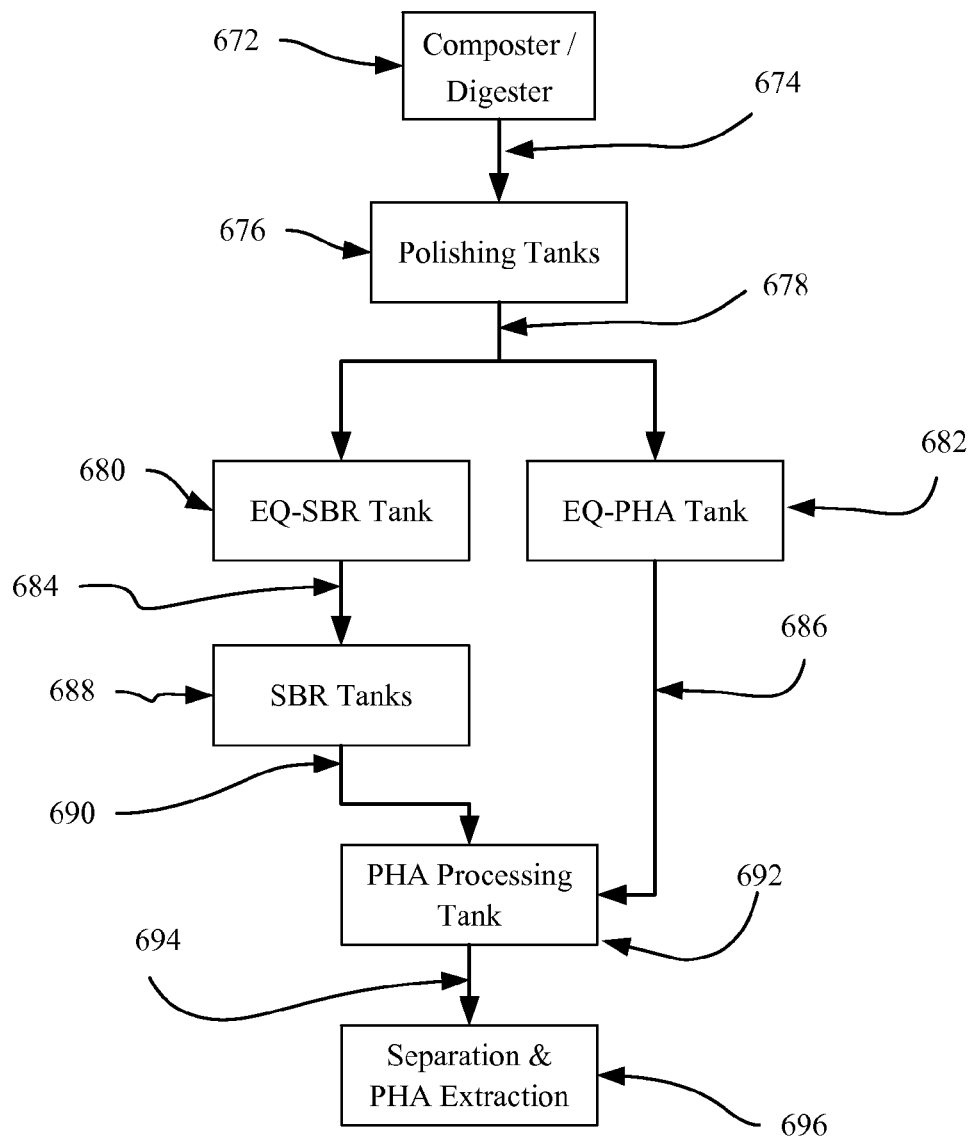
FIG. 6 is a block diagram illustrating components and liquid flows in an example PHA production process utilizing polishing tanks to obtain an approximate desired VFA feedstock liquid composition.

The example will now be described with reference to the components of the system block diagram of FIG. 6, compost leachate liquid 674 from a composter 672 may be placed into one or more anaerobic fermentation tanks 676, which may be referred to herein as a polishing tanks 676. The polishing tanks 676 may be configured to receive a solution of mixed soluble acids, and using anaerobic bacteria convert the solution to the lowest chain fatty acids, including acetic acid and propionic acid, while inhibiting methanogenesis. The starting leachate solution placed in the polishing tanks 676 may contain a range of soluble short-chain fatty acids and soluble long-chain fatty acids, as well as soluble carbohydrates and other soluble carbon sources.

In various embodiments, a plurality of polishing tanks may be configured for parallel or series processing of feedstock liquids. In some embodiments, a single polishing tank may be used. In some embodiments, some polishing tanks may be controlled so as to produce VFA feedstock liquid mixtures with higher concentrations of acetic acid as a percent of total VFAs, while other polishing tanks may be controlled so as to produce VFA feedstock liquid mixtures with lower concentrations of acetic acid as a percent of total VFAs (i.e., feedstock liquid mixtures with higher relative concentrations of propionic acid and/or other longer-chain VFAs).

The polishing tanks 676 may be seeded with acid-phase anaerobic digester bacteria. A polishing tank 676 may be configured to control the pH of the anaerobic fermentation to target a specific mix of VFA concentrations. For example, a pair of dosing pumps, one for acid and one for base may be used to selectively add acid or base to the polishing tank in order to maintain the pH of the liquid within a desired range of a target pH.

The pH set point for the polishing tanks 676 may be selected to drive fermentation towards shorter-chain VFAs or to allow longer chain VFAs to remain. In some embodiments, the polishing tank 676 may use a relatively low pH set point of between about 4 and 5 to inhibit VFA-producing bacteria in order to produce a VFA feedstock with a larger proportion of longer-chain VFAs. In sufficient time (and at higher pH set points), the bacteria in the polishing tanks 676 will tend to break down substantially all of the acids into acetic acid. The bacteria may be encouraged to break down substantially all of the acids into acetic acid at a faster rate by maintaining a higher pH set point of about 5 to about 6. Therefore, progress of fermentation in the polishing tanks 676 may be monitored and fermentation may be stopped when a desired target mixture of VFA concentrations (or ratios) is approximately reached. In various embodiments, fermentation progress may be monitored by monitoring a quantity of carbon or nitrogen in the tank, or by evaluating the liquid with a make-up analyzing device such as a spectrophotometer or other composition analysis device.

When the fermentation in the polishing tanks 676 is complete (e.g., when the approximate desired VFA feedstock composition is reached), the contents of the polishing tanks 676 may be allowed to settle to save the solids to seed a subsequent batch to be processed in the polishing tanks 676.

Table 5 illustrates an example of VFA compositions (in weight percent of total VFAs) of a leachate liquid entering a polishing tank, and compositions (in weight percent of total VFAs) of a VFA feedstock liquid exiting the polishing tank 676 after fermentation.

TABLE 5

Example Polishing Tank VFA Mixture Change

| | Entering PT | Exiting PT |
|---|---|---|
| Acetic Acid (wt %) | 48% | 58% |
| Propionic Acid (wt %) | 19% | 33% |
| Lactic Acid (wt %) | 0% | 0% |
| Isobutyric Acid (wt %) | 3% | 9% |
| Butyric Acid (wt %) | 10% | 0% |
| Isovaleric Acid (wt %) | 4% | 0% |
| Valeric Acid (wt %) | 9% | 0% |
| Caproic (wt %) | 7% | 0% |

In one example, if the VFA feedstock exiting the polishing tank with a composition as shown in Table 5 is directed to a PHA-processing tank 692 (with or without passing through an equalization tank 682 as described below), a PHA resin with PHB/PHV ratio of approximately 67% PHB/33% PHV may be produced. If a resin of higher PHB/PHV ratio is desired, the material exiting the polishing tank may be supplemented with either concentrated acetic acid, or material from a polishing tank that had been allowed to further break down (i.e., having a higher relative concentration of acetic acid). Similarly, if a resin of lower PHB/PHV ratio is desired, the material exiting the polishing tank 676 may be supplemented with either concentrated propionic acid, or material from a polishing tank in which the longer chain acids had not been allowed to break down, thereby leaving a higher relative concentration of fatty acids with chains longer than acetic acid (e.g., acids with 3 carbons or more).

From the polishing tanks 676, the VFA feedstock liquids 678 may be pumped into one of a plurality of equalization tanks 680, 682 where nutrients, such as VFA addition, nitrogen (ammonia), phosphorus (phosphate), and pH may be adjusted to meet a desired VFA feedstock composition. Specific weight ratios of carbon to nitrogen (C:N) may be targeted in each equalization tank.

A first equalization tank, referred to herein as "EQ-SBR" 680 may be configured to prepare a VFA feedstock 684 for one or more sequencing batch reactors (SBRs) 688 configured to produce a bacteria culture liquid 690 rich in PHA-producing bacteria from the prepared VFA feedstock 684. A second of the equalization tanks, referred to herein as "EQ-PHA" 682 may be configured to prepare the VFA feedstock 686 for the PHA production tanks 692 which may be configured to perform a bioplastic production process. The EQ-SBR tanks 680 may have a first target C:N weight ratio of about 6 to about 10, and the EQ-PHA tank 682 may have a second, different target C:N weight ratio of about 10 to about 20.

The sequencing batch reactor tanks 688 may be configured to grow and condition a mixed consortia of non-genetically-modified, wild-type bacteria using environmental conditioning. The environmental conditioning may involve aerobic and anaerobic periods. Air may be sparged into an SBR tank 688 during aerobic periods, and the SBR tank 688 may be sealed off from air being sparged into the tank during anaerobic periods (e.g., by operation of a valve or pump).

A feast-famine process may also be employed in the SBR tanks 688. The feast-famine process may comprise periodically feeding and starving bacteria so as to trigger the bacteria to produce PHA as an energy storage molecule. The SBR tank 688 may be cycled between feast and famine based on a pre-determined cycle time, and/or based on a measured variable such as pH. For example, a feast cycle (during which nutrients may be continuously or periodically delivered to the solution) and/or a famine cycle (during which no nutrients may be added) may proceed for a cycle time of about 6 hours, about 12 hours, about 18 hours, about 24 hours, about 30 hours, about 36 hours, etc.

During each feast cycle or each famine cycle, pH of the solution in the SBR tank 688 may be monitored and maintained (e.g., by delivering a quantity of an acid or a base with a dosing pump) within a suitable range of a pH set point. Suitable pH set points may be between about 7.0 and about 9.0, and may include set points of about 7.2, about 7.4, about 7.6, about 7.8, about 8.0, about 8.2, about 8.4, about 8.6, about 8.8, or about 9.0.

The SBR tanks 688 may also run a maintained baseline feeding strategy, where a low level of feed may be added (e.g., through use of a dosing pump from a feedstock reservoir) in response to a measured concentration of a critical nutrient. When the measured nutrient concentration falls below a threshold level, a small quantity of the nutrient may be added so as to maintain the nutrient concentration within a desired band surrounding a set-point. For example, the nutrient concentration may be maintained within 1%, 5%, 10%, 20% or more above and/or below a set-point. Example set points for the target nutrient concentration may be 1 ppm, 10 ppm, 50 ppm, 100 ppm, 1000 ppm. Nitrogen in the form of ammonia may also be added reactively (i.e., in order to maintain the nitrogen concentration within a desired range of a set point) during the feast periods.

The SBR tank 688 may be configured to decant a portion of the working volume of the SBR tank 688 at the end of the famine period. For example, the decanted portion that becomes the bacteria culture liquid 690 may be about 10% to about 50% or more of the volume of the SBR tank 688. The decanted bacteria culture liquid 690 may then be pumped to a PHA production tank 692. The SBR tank 688 may then be fed again from a new batch of material 684 from the EQ-SBR tank 680.

A bioplastic production process may then be performed in the PHA production tank 692. The PHA production tank 692 may receive bacteria along with the decanted bacteria culture liquid 690 from the SBR tank 688, and may also receive feedstock 686 from the EQ-PHA tank 682. In one example embodiment, the PHA production tank 692 may run for approximately 4 hours. A first portion of this time may be focused on growing as many PHA-rich cells as possible. During this growth phase the tank may be aerated, the pH may be maintained, and the nitrogen levels may be maintained via ammonia addition.

The growth phase in the bioplastic production process may end when the nitrogen has been completely consumed by the bacteria, but VFAs may remain in solution. Air flow into the PHA production tank 692 may be cut off at the same time the nitrogen is eliminated, thereby causing a trigger for PHA accumulation in the bacteria. The bacteria may rapidly produce PHA and consume the remaining VFAs in solution. The entire contents of the PHA production tank 692 may then be pumped to separation and extraction equipment. For example, separation equipment may include a centrifuge or other separation device where the PHA-rich cells may be separated from the remaining liquid and captured.

Once the PHA-rich cells are separated from the liquid, the remaining liquid may be reused as dilution water in an earlier stage of the process. Once separated from the liquid, the PHA-rich cells may be dried (e.g., by heating), thus killing them and stabilizing the PHA. The dried PHA cells may be transported to a processing facility where they can undergo varying levels of extraction and purification processes tailored to different end-uses.

Figure 7:
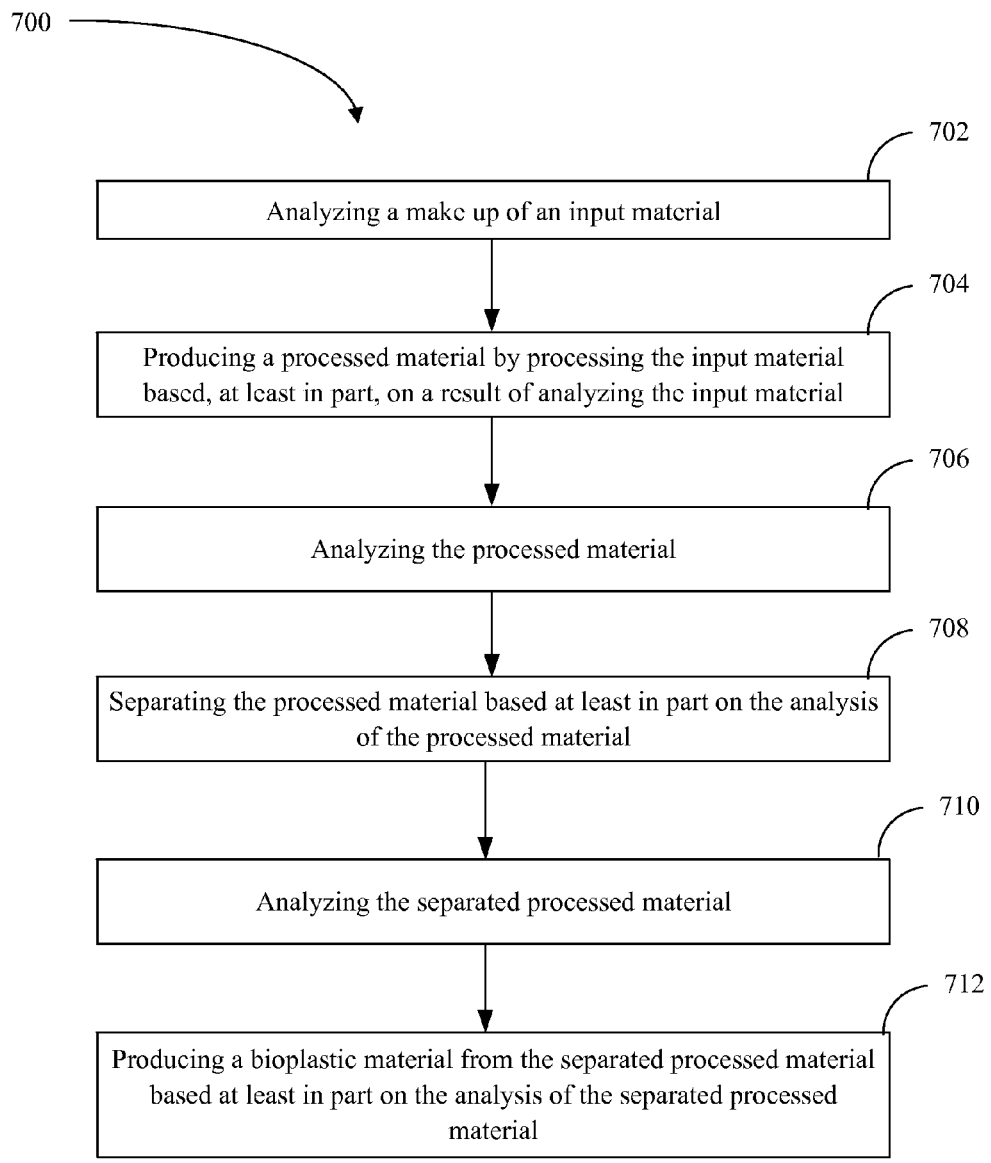
FIG. 7 is a process flow diagram illustrating a process for producing copolymer resins.

FIG. 7 illustrates a process flow diagram illustrating a method 700 for producing copolymer resins in accordance with an aspect of the present disclosure. In 702, an input material is analyzed as shown in FIG. 2 and FIG. 3. In 704, the input material is processed based at least in part on the analysis of the input material, as shown in FIG. 2, FIG. 3, and FIG. 5. In 706, the processed input material is analyzed as shown in FIG. 2 and FIG. 5. In 708, the processed input material is separated based at least in part on the analysis of the processed input material as shown in FIG. 2. In 710, the separated processed input material is analyzed as shown in FIG. 2. In 712, the separated processed input material is polymerized based at least in part on the analysis of the separated processed input material as shown in FIG. 2.

Liquid-Liquid and Solid-Liquid Separation

Some organic acids, which may be VFAs, may be produced during the anaerobic biological breakdown of carbonaceous organic waste in the VFA production process 106 described as part of the present disclosure. Other acids, solids, gases, or other liquids, may also be produced in the VFA production process 106 and/or other portions of the process 200, and may be produced as output materials 112 at any portion of the process 200.

For example, and not by way of limitation, gaseous methane may be produced during the VFA production process 106, and removed from the process 200 after the VFA production process 106 as an output material 112. Further, organic acids may be solubilized in water and distilled or otherwise separated from water during separation process 108. In some cases, both water and concentrated acids may be output materials 112.

Because VFAs range drastically in molecular size and weight from 2 carbon to 36 carbon molecules, different filters 312, 426, and/or 428 (or others) may be employed in the process 200 for membrane filtration of intermediary products of the process 200. By properly selecting the filters 312, 426, and 428, the VFAs may be separated by size.

In some cases, a specific component of a liquid may be isolated by the use of two or more filters. For example, a single VFA to be isolated (referred to herein as a "target VFA") may be isolated from a bulk flowing liquid by using a first filter to remove molecules larger than the target VFA, allowing an intermediate liquid including the target VFA and molecules smaller than the target VFA to pass through the first filter. A second filter may then be used to "trap" the target VFA, by allowing molecules smaller than the target VFA to pass through the second filter, allowing the target VFA to be withdrawn as the un-filtered fluid exiting the second filter. Such an isolation process may be performed using any suitable filters as described in various examples herein.

Figure 8:
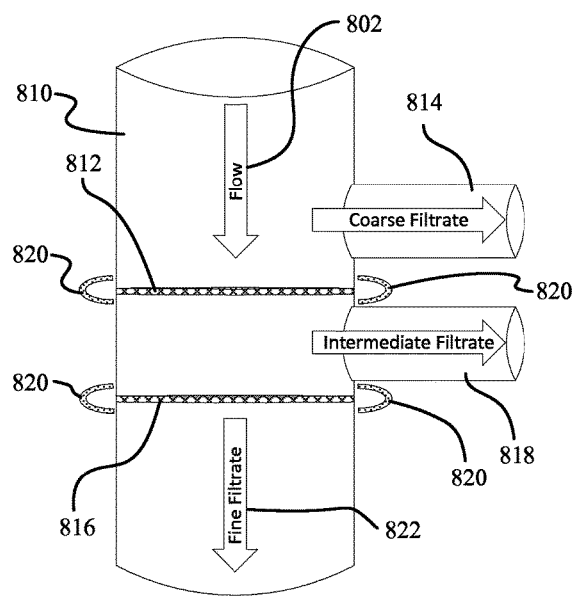
FIG. 8 is a schematic diagram illustrating a filtrate isolation arrangement for removing selected components from a liquid mixture by filtration, including optional electromagnetic field inducing devices.

Such isolation of one or more target molecules may be understood with reference to FIG. 8, which shows a bulk fluid 802 flowing in a segment of a fluid conduit 810, a first (or "coarse") filter 812, a coarse filtrate removal conduit 814, a second (or "fine") filter 816, and an intermediate filtrate removal conduit 818. In this example, the bulk fluid 802 may comprise an aqueous mixture of organic compounds, including various fatty acids. The system of FIG. 8 may also include field inducing elements 820 configured to induce electric and/or magnetic fields for various purposes as described below. As shown in Table 6, many fatty acid molecules have size dimensions different from one another.

TABLE 6

Properties of Selected Fatty Acids

| Name | Formula | # of C's | Max Mol. Size (nm) | Min Mol. Size (nm) | Molecular Wt. (g/mole) | Refractive Index |
| --- | --- | --- | --- | --- | --- | --- |
| Acetic Acid | $C_2H_4O_2$ | 2 | 0.28 | 0.28 | 60.052 | 1.371 |
| Propionic Acid | $C_3H_6O_2$ | 3 | 0.42 | 0.28 | 74.0785 | 1.386 |
| Butyric Acid | $C_4H_8O_2$ | 4 | 0.56 | 0.35 | 88.1051 | 1.3991 |
| Valeric Acid | $C_5H_{10}O_2$ | 5 | 0.7 | 0.28 | 102.132 | 1.408 |
| Hexanoic Acid | $C_6H_{12}O_2$ | 6 | 0.84 | 0.42 | 116.158 | 1.417 |
| Heptanoic Acid | $C_7H_{14}O_2$ | 7 | 0.98 | 0.42 | 130.185 | 1.422 |
| Octanoic Acid | $C_8H_{16}O_2$ | 8 | 1.12 | 0.28 | 144.211 | 1.4285 |
| Lactic Acid | $C_3H_6O_3$ | 3 | 0.42 | 0.42 | 90.08 | 1.439 |

Based on known or measurable differences in molecule size, a filter size may be selected to allow one or more identified molecule types to pass through while preventing one or more other molecule types from passing through the filter.

In the example of FIG. 8, the first filter 812 may have a maximum pore size that is selected to allow at least a first (smaller) organic compound and a second (larger) organic compound to pass through the first filter 812. Any organic or inorganic compounds larger than the first organic compound and the second organic compound will not pass through the first filter 812, and may be removed from the main flow conduit 810 via the coarse filtrate removal conduit 814.

The second filter 816 may have a maximum pore size that is large enough to allow the first (smaller) organic compound to pass through the second filter 816, but small enough to prevent the second (larger) compound from passing through the second filter 816. The first organic compound may then continue to flow through the main conduit 810 along with any other smaller materials in the fine filtrate 822. The second organic compound may be removed from the main conduit 810 via the intermediate filtrate conduit 818.

In various embodiments, any number of filters and intermediate removal conduits may be used. For example, third, fourth, or more filters and filtrate removal conduits may be provided downstream of the second filter 816. In some embodiments, multiple compound isolation configurations such as that shown in FIG. 8 may be arranged in a cascade configuration. For example, the coarse filtrate removed via the coarse filtrate removal conduit 814 may be directed to a second compound isolation conduit with filters sized to isolate one or more compounds from the coarse filtrate fluid.

The materials and properties of the first filter 812 and the second filter 816 may be selected based on the properties of the molecules to be separated and the liquids in which they are dissolved or dispersed. For example, Table 7 below lists various membrane filter types and the smallest particle size that each will prevent from passing through the filter. Depending on the molecules to be separated and/or isolated, any of the filter types listed in Table 7 may be used.

TABLE 7

Membrane Filter Particle Sizes

| Filtration Method | Removal of particles greater than |
| --- | --- |
| Wet Sieve | 10000 nm |
| Particle filter | 1000 nm |
| Microfiltration | 100 nm |
| Ultrafiltration | 10 nm |
| Nanofiltration | 1 nm |
| Reverse Osmosis | 0.1 nm |

Therefore, in some embodiments, membrane filtration using one or more of the membrane filters listed in Table 7 (or any other membrane filter) may be used to separate VFAs or other carboxylic acids by size. In other embodiments, other types of filtration may be used alone or in combination with one or more membrane filters to selectively remove one or more VFAs or other organic compounds from a solution or dispersion. All such combinations of filtration components are within the scope of the present disclosure. For example, and not by way of limitation, magnetic, electromagnetic, and/or electrical filtration may be used to filter desired VFAs from intermediate products within the process 200.

In some embodiments, short-chain fatty acids (1 to 5 carbons) may be separated from aqueous acid phase anaerobic digestion effluent. Short-chain fatty acids may include formic acid (C1), acetic acid (C2), propionic acid (C3), butyric acid (C4), isobutyric acid (C4), valeric acid (C5), isovaleric acid (C5).

As an example, and not by way of limitation, the present disclosure allows for the separation of medium-chain fatty acids (e.g., an acid with 6 to 12 carbon atoms) from an aqueous acid phase anaerobic digestion effluent. Such medium-chain fatty acids may include, but are not limited to, caprionic/hexanoic Acid (6 carbon atoms), enanthic acid (7 carbon atoms), caprylic/octanoic acid (8 carbon atoms), pelargonic acid (9 carbon atoms), capric acid (10 carbon atoms), and undecylic acid (11 carbon atoms). Other organic acids may also be separated from an aqueous acid phase anaerobic digestion effluent.

The addition of inorganic acids or bases to change the pH of the aqueous solution may also cause a specific organic acid to form more or less salt, which allows for that specific organic acid to be more easily separated from the other organic acids. For example, and not by way of limitation, calcium, magnesium, or other materials may be added to the solution to form salts which may create larger molecules with a different polar axis. These larger molecules can be filtered from the solution and processed separately without disrupting the process 200 flow.

By selecting an appropriate pore size for a filter 312, 426, and/or 428, an individual fatty acid may be separated from all of the other fatty acids in solution. For example, and not by way of limitation, one organic acid may be separated from all other short-chain and medium-chain fatty acids (and any other components) in solution by having a first membrane filter of appropriate pore size which allows the desired acid to pass through the membrane with the aqueous filtrate. A second filter membrane with a different pore size may then be placed downstream in the process 200 that does not allow the desired acid to pass through. The second filter would then retain the desired acid in the retentate, while the solution passing through the second membrane (the filtrate) would still contain the other organic acids. Examples of acids that may be retained and/or concentrated in this way may include acetic acid, lactic acid, propionic acid, isobutyric acid, butyric acid, isovaleric acid, valeric acid, etc.

Dynamic Filtration

In some embodiments, filtration of some organic molecules including VFAs may depend on the orientation of the molecules as they approach and pass through a filter. Specific VFAs and other polar organic molecules may have consistently specific ranges of length to width ratios in addition to having consistently specific ranges of absolute size. Therefore, by orienting polar organic molecules along a particular axis prior to directing the molecules through a filter, specific molecules may be allowed to pass through or prevented from passing through filter pores of a known size. For example, as illustrated in Table 8 below, some organic compounds have substantially different minimum and maximum dimensions.

TABLE 8

Minimum and Maximum Dimensions of Example Compounds

| Organic Acid | Max Molecular Diameter (nm) | Min Molecular Diameter (nm) | Reject Filter |
|---|---|---|---|
| Acetic acid | 0.28 | 0.28 | RO |
| Propionic acid | 0.42 | 0.28 | RO |
| Butyric Acid | 0.56 | 0.35 | RO |
| Valeric Acid | 0.7 | 0.28 | RO |
| Hexanoic Acid | 0.84 | 0.42 | RO |

TABLE 8-continued

Minimum and Maximum Dimensions of Example Compounds

| Organic Acid | Max Molecular Diameter (nm) | Min Molecular Diameter (nm) | Reject Filter |
|---|---|---|---|
| Heptanoic Acid | 0.98 | 0.42 | Nano |
| Octanoic Acid | 1.12 | 0.28 | Nano |
| Lactic Acid | 0.42 | 0.42 | RO |

In some embodiments, polar molecules may be placed in a desired orientation by the presence of a magnetic and/or electric field. For example, polar molecules with positive and negative poles may generally be oriented so as to align with an electric and/or magnetic field based on the principles of electromagnetic attraction. If such alignment is performed prior to or while directing the fluid to a filter, the polar molecules may fit through a smaller nominal pore size in a membrane filter in one orientation, even if they might not fit through the filter in another orientation.

For example, a filter may be selected to have pore sizes in between the minimum diameter and the maximum diameter for a particular molecule or compound. If the particular polar molecule is oriented such that its smallest dimension is parallel to the pores of the filter, then the molecule may pass through the filter, whereas the same molecule may be prevented from passing through the filter when the molecule is oriented with its largest dimension parallel to the filter pores.

In some embodiments, a magnetic field may be oriented such that one or more polar molecules are aligned to be strained from a liquid flow by orienting the molecules such that the molecule's larger dimension does not fit through the filter pores, and thus does not pass through the membrane filter (e.g., filters 812, 816, 312, 426, and/or 428).

Depending on various characteristics of a polar organic molecule (such as physical size, polar charges, molecular weight, etc.), some polar organic molecules may be oriented with a weaker electric or magnetic field as compared to other polar organic molecules. Therefore, in some embodiments, specific polar organic molecules may be targeted for alignment by varying the strength of an electric or magnetic field applied to the fluid conduit adjacent to one or more filters.

By controlling the orientation and strength of an electric or magnetic field, various VFAs may be removed from anywhere in the process 200, and may be specifically removed via filtration portions of the process 200 at filters 812, 816, 312, 426, and/or 428.

Electric or magnetic fields configured for affecting the orientation of organic compounds in a fluid flowing within a conduit may be created or controlled by a variety of field inducing devices 820, which may include permanent magnets, electromagnets, various wire configurations, or other devices. For example, permanent magnets useful as field inducing devices may include any magnet that may retain desired magnetic properties in the absence of an inducing field or current. Permanent magnets may be made of any suitable material and in any shape desirable for use as a field inducing device 820. For example, permanent magnets may be bar-shaped, ring-shaped, plate-shaped, disc-shaped, arc-shaped, crescent-shaped, cylindrical, segmented, or otherwise shaped or configured.

When used as field inducing devices 820, electromagnets may include structures comprising one or more coils of electrically conductive wire surrounding a magnetizable core. In some cases, a magnetizable core may be omitted, and a configuration of electrically conductive wires may be configured to directly interact with fluids in a conduit.

Figure 9:
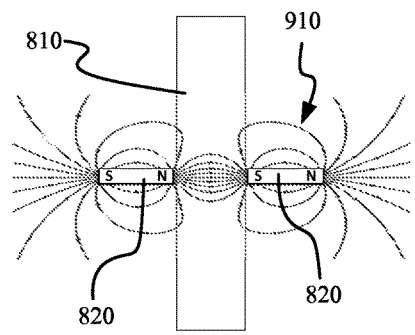
FIG. 9 is a schematic diagram illustrating an example of electromagnetic fields induced in a liquid conduit.
Figure 10:
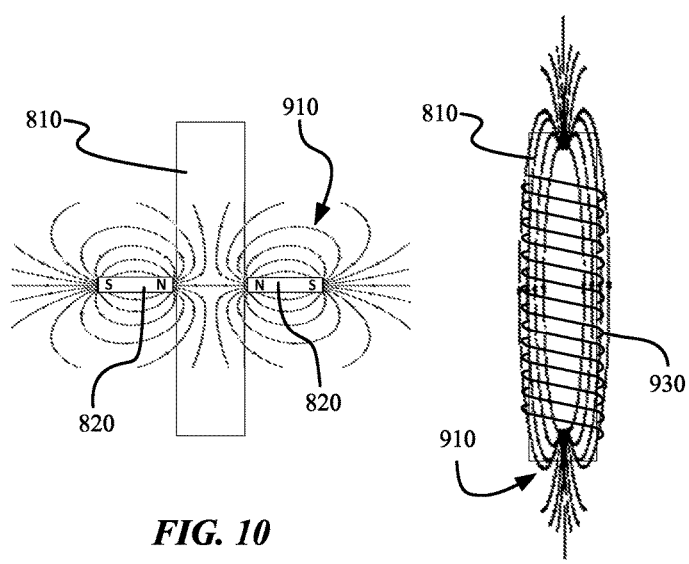
FIG. 10 is a schematic diagram illustrating an example of electromagnetic fields induced in a liquid conduit.
Figure 11:
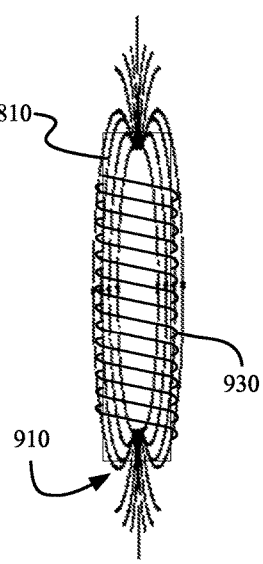
FIG. 11 is a schematic diagram illustrating an example of electromagnetic fields induced in a liquid conduit.

FIG. 9, FIG. 10, and FIG. 11 schematically illustrate examples of magnetic and/or electric fields (shown by field lines 910) that may be produced by one or more field inducing devices 820 in various orientations relative to the conduit 810 through which a fluid may flow. Any of the field orientations of FIG. 9, FIG. 10, or FIG. 11 or other field orientations may be desirable either to cause the oriented molecules to be prevented from passing through a filter or allowed to pass through a filter, depending on relative sizes of the molecules and the filter pores as well as whether the polar axis is aligned with a larger dimension or a smaller dimension of a targeted organic compound.

In general, a positive pole (or positive poles) of a polar molecule will tend to be attracted by the negative poles of an induced field and repelled by the positive pole of the induced field. Similarly, the negative pole (or negative poles) of a polar molecule will tend to be repelled by the negative poles of an induced field and attracted by the positive pole of the induced field. Therefore, polar molecules within a conduit may be oriented by orienting positive and negative poles of one or more induced fields in a desired region of a conduit.

FIG. 9 illustrates the interaction of two fields 910 oriented with opposite poles of first and second field inducing devices 820 on opposite sides of a conduit 810. The field within the conduit 810 resulting from field inducing devices oriented as shown in FIG. 9 has a predominant polar axis that is perpendicular (or "normal" or "transverse") to the longitudinal axis of the conduit 810. Such an arrangement of induced fields may be desirable in order to orient polar axes of polar organic molecules in the transverse orientation.

FIG. 10 illustrates the interaction of two fields 910 oriented with same poles of first and second field inducing devices 820 on opposite sides of a conduit 810. The field within the conduit 810 resulting from field inducing devices oriented as shown in FIG. 10 has a predominant polar axis that is parallel to the longitudinal axis of the conduit 810. Such an arrangement of induced fields may be desirable in order to orient polar axes of polar organic molecules in the longitudinal orientation.

FIG. 11 illustrates a field 910 induced in a section of a conduit 810 by a coil of electrically conductive wire 930 surrounding the section of the conduit 810. The field 910 within the conduit 810 resulting from field inducing devices oriented as shown in FIG. 11 has a predominant polar axis that is parallel to the longitudinal axis of the conduit 810. Such an arrangement of induced fields may be desirable in order to orient polar axes of polar organic molecules in the longitudinal orientation.

In various embodiments, any two or more field inducing mechanisms or orientations of field inducing devices may be employed in concert to achieve one or more desired orientations of one or more polar organic compounds in a fluid flowing within a conduit. Field inducing devices 820 may be oriented in any desired positions relative to one another and to the conduit 810, depending on the desired effect. For example, two, three or more field inducing devices 820 may be positioned adjacent to a section of conduit 810 to produce a desired field interaction pattern.

For example, the field orientations of either FIG. 9 or FIG. 10 may be produced with a single pair of electromagnets as field inducing devices positioned on opposite sides of a conduit 810. The system may be switched between the field orientations of FIG. 9 and FIG. 10 by reversing the direction of electric current in one of the field inducing electromagnets. The strength of one or more fields induced by an electromagnet may be increased or decreased by increasing or decreasing electric current or voltage delivered to a field inducing device. Such a system may be combined with a field inducing device such as that illustrated in FIG. 11 to allow further variations in induced field orientation and strength.

In some embodiments, various fields may be induced so as to selectively orient polar molecules in a transverse plane in the conduit or in any other plane intersecting the conduit. For example, a first pair of field inducing devices may be used to orient polar molecules in a north-south orientation within a transverse plane. The first pair of field inducing devices may be switched off (e.g., by removing power to electromagnets or by physically removing permanent magnets) and a second pair of field inducing devices may be activated to induce one or more fields orienting polar molecules in an east-west orientation within the transverse plane. Such an arrangement may be desired in order to orient polar molecules relative to shaped pores in a filter so as to selectively allow or prevent passage of an oriented organic compound through the filter.

In some embodiments, a process for selecting a targeted compound may include establishing a first electric and/or magnetic field within a first section of conduit and directing a fluid containing the targeted compound through the first section conduit to a first filter. In some cases, the process may also include directing the fluid through a second section of conduit toward a second filter, establishing a second field in the second section of conduit adjacent to the second filter, and removing a portion of the fluid including the targeted compound from an intermediate fluid conduit between the first filter and the second filter. In some cases, the process may also include changing a strength or an orientation of the first field or the second field.

In some embodiments, field inducing devices may include one or more patterns of conductive wires embedded in or adjacent to a filter (such as any of filters 812, 816, 312, 426, and/or 428). For example, a filter may comprise a laminated structure with one or more layers of a porous membrane with pores of a desired size and one or more layers containing electrically conductive wires supported adjacent to, in contact with, or integrally formed with the filter membrane.

Figure 12:
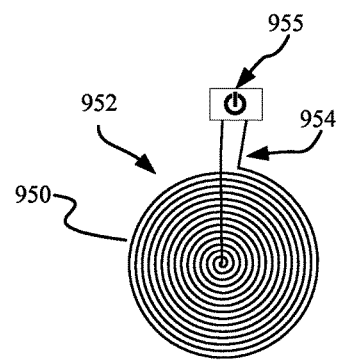
FIG. 12 is a schematic diagram illustrating a spiral pattern of electrically conductive wires that may be positioned in or adjacent to a membrane filter for inducing electromagnetic fields in a region adjacent to the filter.
Figure 13:
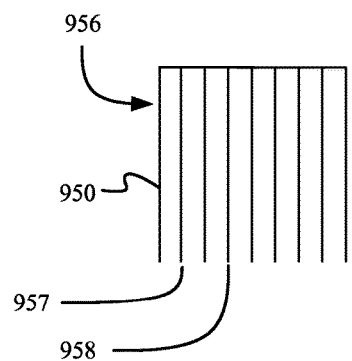
FIG. 13 is a schematic diagram illustrating a grid pattern of electrically conductive wires that may be positioned in or adjacent to a membrane filter for inducing electromagnetic fields in a region adjacent to the filter.

FIG. 12 and FIG. 13 illustrate examples of electrically conductive wire patterns that may be provided in or adjacent to a filter membrane. The pattern of FIG. 12 includes a single conductive wire 950 in a spiral configuration 952, with lead wires 954 that may be electrically connected to an electronic controller and/or a power supply 955. If the spiral wire 952 is oriented in a transverse plane in a longitudinal conduit, then directing an electric current through the spiral wire 952 may induce a field with a polar axis parallel to the longitudinal axis of the conduit. Changing the direction of the applied current may change the direction of the induced field. In some embodiments, multiple layers of spiral wires may be combined to further alter the shape and/or strength of an induced field.

A power supply (e.g., 955 in FIG. 12) configured for delivering electric current to a pattern of wires may comprise any suitable power supply, such as a direct current power supply with constant current, variable current, constant voltage, or variable voltage capabilities. Alternatively, the power supply may be an alternating current power supply configured to deliver a constant AC signal, a variable signal, or a variety of AC signals.

FIG. 13 illustrates a plurality of wires 950 oriented in a grid pattern 956. When a pair of wires, such as wires 957, 958, is connected to a power supply and an electric current is directed through the wires, the current will follow a partial loop in the plane of the wires, thereby inducing a magnetic field with a polar axis perpendicular to the plane of the wires. In various embodiments, various pairs of wires may be simultaneously or sequentially connected to a power supply in order to direct electric current through a variety of loops in the plane of the wires. For example, the power supply may be switchably joined to each of the individual wires, and a controller may be configured to switch the power supply to deliver current to selected pairs of wires at different times or simultaneously.

In some embodiments, two or more parallel layers of wires may be provided to further configure the induced field as desired. In some embodiments, the grid of wires of a second layer may be rotated about the longitudinal conduit axis relative to a first layer, such as by 90°, 45° or by any other angle. In some cases, the grid of wires may include curved segments rather than straight segments as illustrated in FIG. 13.

In some embodiments, the wires shown in FIG. 12 or FIG. 13 may comprise small coils of wires (e.g., similar in shape to coiled piano wires) with longitudinal axes oriented in the illustrated patterns. Small coiled wires or straight wires may also be arranged in any other pattern for use as described herein.

In various embodiments, filters with layers of patterned wires may be used for other purposes in addition to or instead of inducing fields within the conduit. For example, applying an electric current to the wires and reversing polarity of the applied electric current multiple times per second (e.g., at 50 Hz, 60 Hz or any other suitable frequency) may cause polar molecules within the fluid to rapidly change orientation, thereby causing heating due to friction between adjacent molecules. Such localized heating of the fluid and/or the filter membrane may be useful for causing temperature-linked changes to properties of the liquid. For example, density and viscosity tend to be temperature-dependent, so localized heating may be used to a decrease viscosity of a fluid passing through a filter. Any of the filters used in the various systems and methods herein (e.g., any of filters 812, 816, 312, 426, and/or 428) may be configured to heat a fluid, a filter membrane, or other objects by induction. In some embodiments, the wires may be made of an electrically conductive material with a sufficiently high electrical resistance that the wires may be used to heat the filter membrane and/or the fluid by resistive heating when a sufficient electric current is passed through the wires.

In some embodiments, filters with layers of patterned wires may be used for performing flow measurements of fluid flow rate and/or chemical composition of the fluids passing through the filter (which may include any of filters 812, 816, 312, 426, and/or 428). For example, a fluid containing a quantity of polar molecules flowing through a plane of wires (whether adjacent to a filter or not) may induce one or more electric currents in the wires (depending on the pattern of wires as described above). A particular wire configuration may be calibrated with fluids of known compositions in order to obtain induced electric current signals corresponding to the particular compositions. Using such calibration values, induced currents may be evaluated to estimate the composition of fluids flowing past the wires. In some embodiments, flow rates may be similarly detected based on calibration values obtained by flowing fluids at known flow rates and detecting induced electric currents.

In some embodiments, by measuring the flow through one or more of the filters 312, 426, and/or 428, the wires may be controlled to increase the flow, decrease the flow, or open, close, or otherwise modify the flow through filters 312, 426, and/or 428 such that desired particulates, acids, or other portions of the flow may be removed or passed through the filters 312, 426, and/or 428. For example, orienting molecules so as to prevent them from passing through a filter may cause some pores to be blocked to the passage of smaller molecules. Once enough pores become blocked, the bulk flow rate of both solutes and solvent (e.g., water) through the filter may decrease or stop.

In some embodiments, wires in or adjacent to a filter (e.g., filters 812, 816, 312, 426, and/or 428) may also assist in assessing membrane viability, rupture, or clogging of the filters 312, 426, and/or 428, and may also be used to remedy clogging of the membrane. For example, membrane viability, rupture or clogging may be deduced based on measured flow rates as described above. In some embodiments, clogging may be remedied by differently orienting polar compounds so that all compounds may pass through a filter. In other cases, if a filter has become blocked due to an accumulation of trapped molecules, changing an induced field so as to cause molecules to rotate to different positions may allow for some of the trapped molecules to pass through the filter, thereby clearing or reducing the blockage.

By enabling a variable electromagnetic field in the filters 312, 426, and/or 428, the present disclosure also allows for alteration of the flow through the filters 312, 426, and/or 428. For example, a strong enough electromagnetic field may close the pores of the filters 312, 426, and/or 428 altogether, or create a variable pore size for one or more of the filters 312, 426, and/or 428.

Figure 14:
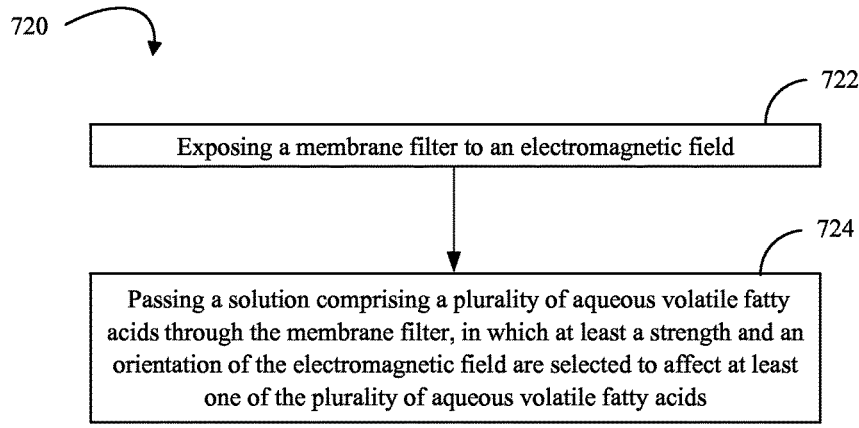
FIG. 14 is a process flow diagram illustrating a process for filtering targeted polar organic molecules.

FIG. 14 illustrates a process flow diagram illustrating a method 720 for electromagnetic separation in accordance with an aspect of the present disclosure. In 722, a membrane filter is exposed to an electromagnetic field. In 724, the aqueous carboxylic acid is dissolved with a solvent in the solution. The solution comprises a plurality of aqueous carboxylic acids and is passed through the membrane filter. A strength and an orientation of the electromagnetic field are selected to affect at least one of the plurality of aqueous carboxylic acids in the solution.

In some embodiments, the systems and methods described with reference to FIG. 8-FIG. 13 may be used to isolate or remove one or more inorganic polar compounds from a liquid by selectively orienting the one or more inorganic polar compound in a desired orientation relative to a filter.

Plug Flow Digester

Figure 15A:
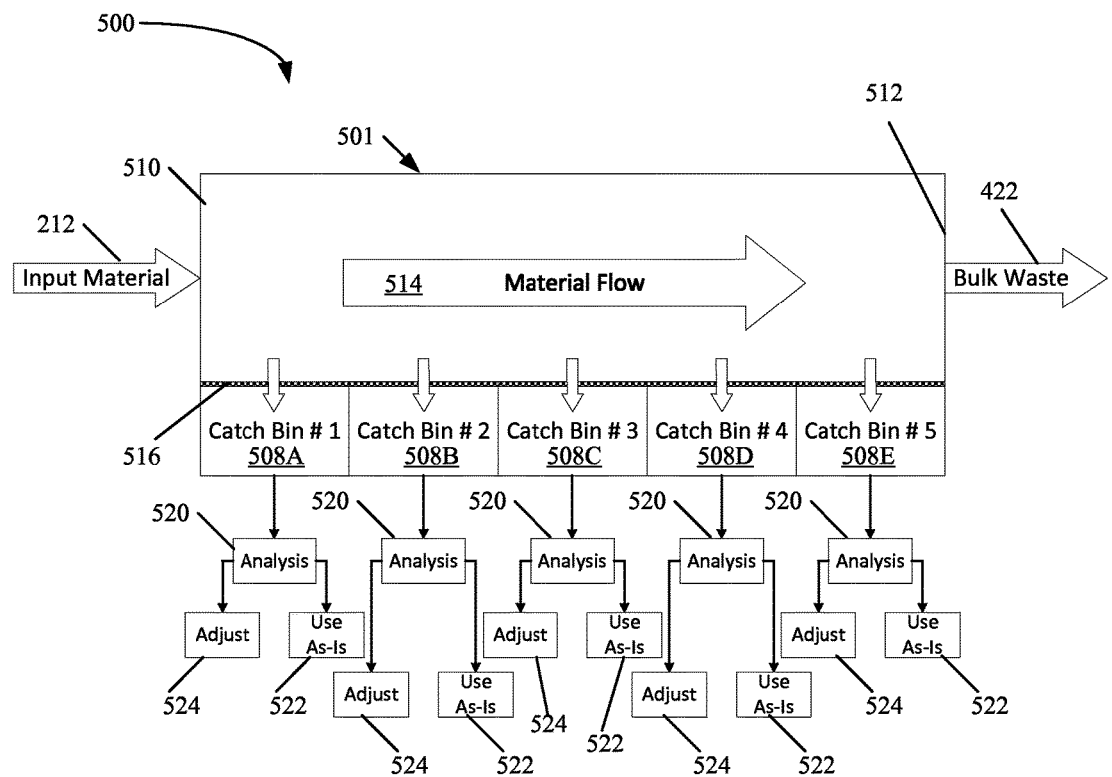
FIG. 15A is a schematic block diagram illustrating an embodiment digester that may be used in various process embodiments.
Figure 15B:
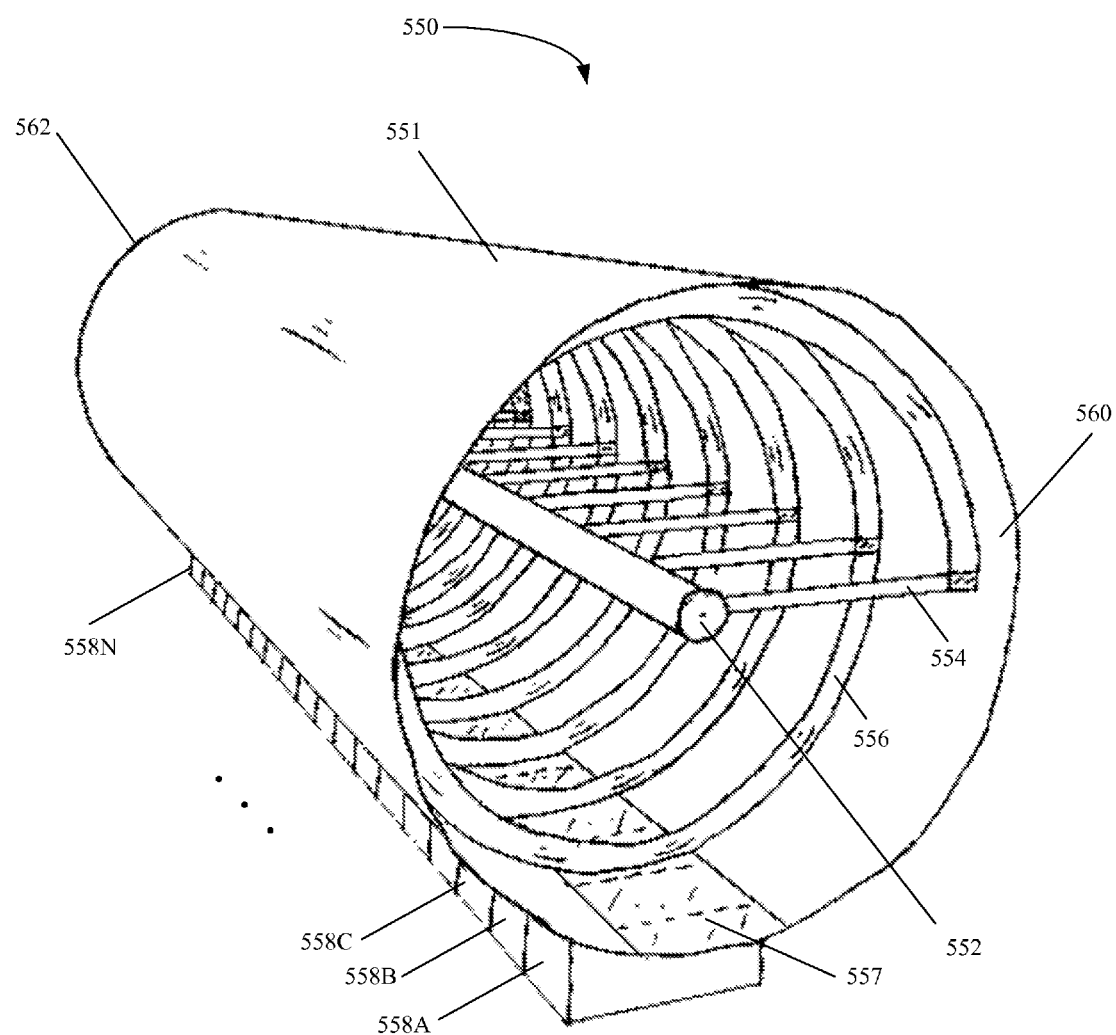
FIG. 15B is a diagram illustrating a perspective view of a digester that may be used in various process embodiments.

FIG. 15A and FIG. 15B illustrate digesters 500 and 550 with advantageous features and configurations. The digesters 500 and 550, which may be used alone or in combination with other digesters as described with respect to FIG. 5, may be configured to allow for "plug flow" processing of the material 404. The digesters 500 and 550 may be used as any of the digesters (e.g., process chambers 406, 412) in the systems and processes described herein.

The digesters 500 and 550 may also allow for separation of different acids and other liquids from the digestion process at different times and points during digestion. Removing liquids from different stages of digestion may advantageously allow for liquids with different concentrations of digestion products to be separately obtained, evaluated, and used in various parts of the overall process 200.

As shown in FIG. 15A, the digester 500 may generally include a bulk material chamber 501 through which bulk material 514 flows horizontally from an input end 510 to an output end 512. The chamber 501 may be separated from a plurality of catch bins 508A-508E by a plurality of filter screens 516. Each catch bin 508 may be fluidically coupled to a make-up analysis module 520, which may evaluate the make-up of liquids in the corresponding catch bin 508. Depending on the detected make-up of the liquids, the liquids may be directed for use by a down-stream process 522, or may be adjusted 524 (e.g., by separation, additives, etc.) before being directed to a down-stream process for use. In some embodiments, a downstream process for using materials from the catch bins 508 may include a polymerization process or other bioplastic production process (e.g., 110 in FIG. 2).

In some embodiments, the material 514 may be moved through the chamber 501 in a plug flow with minimal mixing. Some mechanisms for advancing flow through the chamber 501 are described below. Moving material 514 through the chamber 501 with minimal mixing may be advantageous due to the time-dependent nature of anaerobic digestion. However, in other embodiments, a greater degree of material mixing may be acceptable.

As material 514 moves through the chamber 501, organic materials may be digested by bacteria present in material mixture. Liquids produced by the digestion as well as any liquids already present in the material may be drawn by gravity until they pass through the filter screens and into the catch bins 508. Although FIG. 15A illustrates only five catch bins 508, the digester 500 may include as many or as few catch bins as desired.

The digester 500 allows for the capture of liquids at different stages of the anaerobic bacterial digestion process. In some embodiments, the rate of material flow through the chamber 501 may be configured such that hydrolysis, acidogenesis, and acetogenesis occur within the chamber, but before the digestion process proceeds to methanogenesis. In other embodiments, methanogenesis may be allowed to occur within the chamber 501.

In some embodiments, material 514 may be continuously moved through the chamber 501 in a plug-flow or mixing fashion. In other embodiments, the material 514 may be occasionally moved through the chamber, such as by advancing material 514 by a distance and then stopping the movement for a period of time before again advancing the material 514 towards the output end 512.

For the purposes of description, the digestion process using the digester 500 will now be described with reference to a single "plug" of material moving from the input end 510 of the chamber to the output end 512. In general, if the material 514 introduced at the input end 510 of the chamber 501 contains substantially undigested biomass, the bacteria in the digester 500 will begin to break down the material 514 in the plug through hydrolysis. Liquids produced by hydrolysis may drip into the first catch bin 508A and/or the second catch bin 508B.

As the plug material moves through the chamber 501, the material may be further broken down by acidogenic processes. Acids produced by acidogenic bacteria may drip into the second catch bin 508B, the third catch bin 508C, and/or the fourth catch bin 508D. As the plug material continues to move through the chamber 501, the material may be further broken down by acetogenic processes. Liquids containing acetate, including acetic acid produced by acetogenic bacteria (such as *clostridium aceticum* in one embodiment) may drip into the fourth catch bin 508D and/or the fifth catch bin 508E.

In some embodiments, one or more catch bins 508 may be closed so as to prevent liquids or materials from falling into the bin. Closing one or more bins may allow digestion to proceed for a longer time (and therefore a longer distance through the chamber, assuming continuous movement) before removing liquids from the chamber 501.

FIG. 15B illustrates a digester 550 in accordance with an aspect of the present disclosure and may include any of the features and advantages described with respect to FIG. 15A. The digester 550 may include a cylindrical chamber 551, a shaft 552, and an auger 554. A helical drive ribbon 556 may be attached to the auger 554 so as to be rotatable by the shaft about the axis of the shaft. The shaft 552, auger 554, and ribbon 556 may rotate, either through motorized rotation or other mechanical/electrical forces, to move material through the digester 550.

The material may be fed into the digester 550 through the front 560, or may be fed through another opening in the outer wall of the cylinder 551. The digester 550, although shown as substantially level, may also be tilted to provide gravitational assistance to the material as the material passes through the digester 550. Further, the digester may be made in various sizes, e.g., ten feet long with a two foot diameter, twenty feet long with a four foot diameter, twenty feet long with a three foot diameter, etc., without departing from the scope of the present disclosure. In some embodiments, much larger sized digesters may also be used, such as 40 feet long with a 10 foot diameter, or more.

The rotational speed of the shaft 552 and the number of turns in the auger 554 and ribbon 556 may dictate how fast the material will be pushed through the digester 550. Because digester 550 may be an acid phase digester, there may be a certain minimum or maximum amount of time that material should be housed in the digester 550. For example, if material is left too long in the digester 550, e.g., longer than fifteen days, the material may begin to produce substantial quantities of methane gas inside of the digester 550, which may damage the digester 550 or prevent further generation of acids from that batch of material.

In another aspect of the present disclosure, the shaft 552 and the ribbon 556 may be optional parts of the digester 550. In such embodiments, the digester may be referred to as a "batch" digester, in which the material in the digester 550, rather than being moved along the axis of the digester 550, is digested as a single batch of material. The batch of material may be placed into the digester 550 through an opening in any portion of the cylinder 551 or other part of the digester 550. Further, there may be other types of digesters, such as a continuous flow digester, sequenced batch digesters, fed batch digesters or others that are considered within the scope of the present disclosure. In other embodiments, the ribbon 556 and shaft 552 may be replaced by other mechanical elements configured to move the bulk material through the digester chamber 551. For example, such elements may use peristaltic flow, gravity, centrifugal forces, pistons, air pressure, inflatable flexible bladders, or other forces or elements configured to move bulk material through the digester chamber 551.

Regardless of whether the digester 550 is a batch, continuous, plug-flow, or other type of digester, the digester 550 may also include one or more screens 557 along the bottom of the cylinder 551. The cylinder 556 of the digester 550 may be rotated such that the screen 557 is rotated to a position where the screen 557 may be "opened" such that material may be placed into the cylinder 551 through the opening in the screen 557. The screen 557 may then be closed and the cylinder 551 rotated such that the screen 557 is rotated to be proximate to the bins 558A-558N.

In various embodiments, any suitable mechanism may be used to prevent liquid or other material from flowing into one or more of the bins. Such mechanisms may include valves, sliding doors, one or more iris mechanisms, etc. In some embodiments, each bin may have an individually operably closing mechanism which may be operated to selectively close one or more bins to prevent fluids or other materials from flowing into the selected bin.

In some embodiments, bin closure mechanisms may be omitted entirely. In such embodiments, if liquid collected in one or more bins is determined (based on analysis by a make-up module or other analyzer) to require further processing, the liquid in that bin may be directed back into the digester or to another digester or processing system.

Regardless of whether the digester 550 is a batch, continuous, plug-flow, or other type of digester, the screen 557 may be of different sizes along the length of the chamber 551, to allow for different sized particles and/or liquids, or liquids only, to be drained from the cylinder 551 into the various catch bins. The liquids or other materials drained from the cylinder 551 may be captured in bins 558A-558N, attached along a length of the cylinder 551. Each bin 558A-558N may capture the drained materials at different points along the length of the cylinder 551, and thus each of the bins 558A-558N may catch liquid at different locations in the digestion process.

Although shown in cylindrical form, the digester 550 may be of other shapes or cross-sections without departing from the scope of the present disclosure. For example, and not by way of limitation, the digester 550 may be rectangular in shape and square or rectangular in cross-section. The digester 550 may also have the screens 557 at different locations, such as in a corner or off-centered, in any digester 550 configuration or shape.

An example of a digester having a different shape may be a cargo-container, where the screen 557 is placed in a wall, a floor or a ceiling, or off-centered in the cargo container. The cargo container may then be employed as a batch-processing digester 550. The digester 550 may also have different cross-sections along the length of the digester. For example, and not by way of limitation, one portion of the digester 550 may be a plug-flow digester having a cylindrical cross-section as shown in FIG. 15A. Another portion having a rectangular cross-section may be coupled to the cylindrical portion of the digester. The material flowing through the digester may be processed with a plug flow process in the cylindrical portion, and with a batch process in the rectangular portion. Various cross-sections, shapes, and sizes are envisioned within the scope of the present disclosure.

The digesters 500 and 550 may also include any number of pumps, valves, or other flow control elements configured to recirculate liquids from one or more bins 508A-508N or 558A-558N and return the liquid into the cylinder 501 or 551, or to direct liquids to other processing equipment. The recirculation may occur directly above the bin, or directly above one or more downstream bins to move the liquid along with the solids that are being pushed through. Each of the bins 508A-508N or 558A-558N may be sampled or analyzed to determine the physical and chemical make-up of the liquids at various points in the digestion process.

In some embodiments, the digesters 500 and 550 may be operated in a non-sterile environment. The material fed into the digesters 500 and 550 may be sterile or non-sterile, e.g., the material may be organic waste products such as fruit culls, agricultural waste, industrial waste, restaurant waste, etc., and as such, the digester may accept non-sterile materials and process these materials in less than sterile environments.

The digesters 500 and 550, in another aspect, may also allow for the use of different bacterial digestion agents along the length of the digester 500 or 550. As such, each of the bins 508A-508N or 558A-558N may collect liquid that contains different types of acids, or different concentrations of acids, along the length of the digester 500 or 550. Each of the collections in the bins 508A-508N or 558A-558N may also be directed to different processing steps within process 200, depending on the acids present, the concentrations, and other factors.

By monitoring the collected liquids in the bins 508A-508N or 558A-558N, as well as monitoring the samplers 326, 328, 440, 442, or other samplers within the process 200, concentration ratios of different VFAs, lactic acid, and other acids and compositions may be achieved. By having different concentration ratios, different output materials 112 having different material qualities and characteristics may be produced. For example, the polyhydroxybutyrate (PHB) to polyhydroxyvalerate (PHV) ratio of the output material changes the material properties. By changing the feedstock characteristics, through different concentration ratios of different acids, the PHB/PHV ratio can be controlled in the process 200. Further, by separating or not separating some of the acids, such as lactic acid, from the digester 500 or 550, the production of polylactic acid (PLA) can be inhibited or enhanced in the output material 112.

The process 200, at least through the samplers 326, 328, 440, and 442, may have automated (via the processor 324) or manual monitoring and adjustment of the process materials to ensure the consistent production of the output material 112 having the desired material properties. The process 200 samples materials throughout to measure concentrations of nutrients and then calculates the supplemental material to add to or dilute the process material in order to achieve a desired recipe for consistent material properties in the output material 112.

Some materials that are created, or are by-products of the process 200 may be inhibitory to the anaerobic digestion process of the process chambers 406 and/or 412. For example, and not by way of limitation, citrus culls and rots may represent a good feedstock for the production of PHA resins, but limonene, and other essential oils present in a citrus cull feedstock, may inhibit the anaerobic digestion process. The process 200 may recapture these essential oils as a by-product of the process 200, which also aids in the efficiency of the process 200 overall.

Slurry Analyzer

Figure 17:
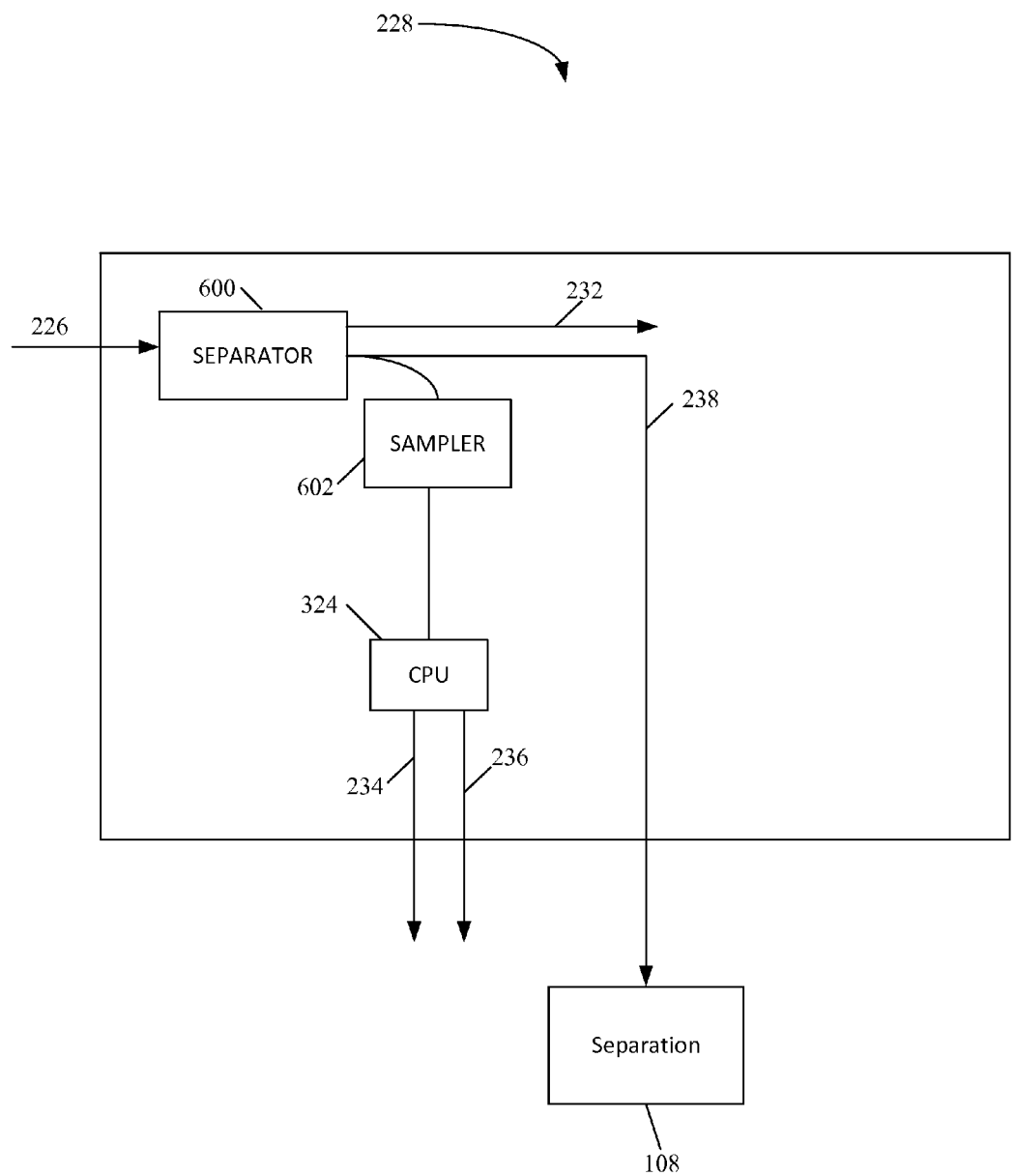
FIG. 17 is a schematic block diagram illustration of a slurry make-up module that may be used to analyze materials in various process embodiments.

FIG. 17 illustrates a slurry make-up module 228 in accordance with an aspect of the present disclosure. Slurry make-up module 228 accepts output 226 from the digester 500, and separates the incoming material in separator 600. Separator 600 may, for example, separate limonene from the acids and send the limonene as a by-products via 232. Other separations may be done by separator 600 to separate individual acids from the output 226.

To separate each acid, or one output of the slurry make-up module 228 from another, a sampler 602 samples the output stream 238. This may be analyzed electronically through the processor 324, or manually, as desired. The processor 324 may send signals 234 and/or 236 to control the nutrient additive bank 222, or the control additives 240, to control other parts of the process 200. These signals may be administered manually by an operator if desired.

Referring again to FIG. 2, the separation process 108 may also be analyzed, either electronically or manually, to determine the concentration of acids in the separated product 242. The liquid make-up analysis module 244 may be similar to the make-up module 206 and corresponding processes described with respect to, e.g., FIG. 3. The liquid make-up analysis 244 may also provide inputs to the control additives 240 to provide inputs 246 that may change the separation process 108.

The output stream 238 may also be sent to separation process 108, which may include output 250 as an output. The output 250 may be used during the bioplastic production process 110. The output 250 prior to bioplastic production, or a polymer stream (which may be referred to as a cell broth) 252 that may be analyzed during or after bioplastic production, may be sent to polymer make-up module 254. The polymer make-up module 254 may examine the polymer stream 252 and/or output 250, and determine, either chemically, visually, or through other analyses whether or not the bioplastic production process 110 is producing the desired output material 112. If not, the polymer make-up module 254 may, either independently, through the processor 324, or through other devices, control the polymer additive module 256 to add materials 258 to the bioplastic production process 110, in order to produce the desired output material 112.

The polymer make-up module 254 may use a microscope, camera, spectrophotometer, or other device, and software or other comparison tools, to compare a sample of the output 250 and/or the polymer stream 252 to a known sample of material or data obtained by analyzing a known sample of material. Through visual, chemical, or structural comparison of the output 250 and/or the polymer stream 252, the polymer make-up module may alter the bioplastic production process 110, or other portions of the process 200, to more closely match the output 250 and/or the polymer stream 252 to the known material. This comparison may be done in real-time to control the process 200 during operation.

For example, and not by way of limitation, PHA concentration may be measured by sampling the output 250 on a microscope slide. The slide may then be viewed in a microscope using phase contrast microscopy. The positioning of the slide may be controlled until recognition software or other recognition methods identify cells on the slide. The area of the cells can then be compared to the area of any intracellular granules (PHA) to approximate or identify a percentage of cells that contain the desired material, in this case, PHA.

Further, the polymer make-up module may also determine other characteristics of the output 250 and/or the polymer stream 252, such as the percentage of weight of the cells in the material, percentages of other cells in the material, etc. This information can then be stored for later analysis, or placed in records for each batch of materials being produced, or may be used as a trigger to stop the production process when a desired PHA concentration or other material properties are reached. The polymer make-up module 254 may also use different wavelengths or different sensors to determine the percentage of different monomers, such as PHV and PHB, to allow for additional analysis of the output 250 and/or the polymer stream 252.

Spectrophotometric Analysis and Analyzers

In some embodiments, a make-up module for analyzing the composition of a mixture at various points in a bioplastic production process may include a suitably configured spectrophotometric analyzer (also referred to as a spectrophotometer). In various embodiments, the polymer make-up module 254, or the make-up module 206 may be configured to perform spectrophotometric analysis of materials.

In some embodiments, a spectrophotometer may be configured, in conjunction with the processor 324 or a separate processor, to identify and quantify one or more polar organic molecules within an aqueous liquid using spectrophotometric techniques. In some embodiments, a spectrophotometric analyzer may also be configured to utilize one or more magnetic and/or electric fields to selectively orient polar organic molecules relative to a spectrophotometric light source and detector.

Spectrophotometry is generally defined as the quantitative measurement of the reflection or transmission properties of a material as a function of wavelength, and generally involves directing light of one or more specified wavelengths through a sample, receiving transmitted light at an opposite side of the sample, and evaluating the received light. The amount of light of specified wavelengths that is absorbed by the sample may be measured based on the difference between the known transmitted light and the light received by the detector. The amount of light of specific wavelengths absorbed by the sample may be correlated with the concentration of various chemical and/or biological constituents of the sample. In other words, the amount of light that passes through the sample may be indicative of the concentration of certain compounds that do not allow light to pass through.

As discussed herein, some VFAs and other polar organic compounds may have different minimum and maximum sizes which may be aligned with a polar axis. As a result, such polar organic molecules may be placed in a desired orientation by an electric and/or magnetic field. If a polar organic molecule with an elongated dimension is oriented such that the elongated dimension is parallel to a line between a light source and a light detector, the molecule may absorb less light and/or different wavelengths of light than when oriented with the elongated dimension perpendicular to the light source-detector line.

FIG. 16A to FIG. 16D illustrate an example embodiment of a spectrophotometer 1000 configured to evaluate polar organic molecules aligned in various orientations. In some embodiments, the spectrophotometer 1000 may comprise a sample cell 1010 with an in-flow conduit 1012 and an out-flow conduit 1014. In other embodiments, a single conduit may be used for both in-flow and out-flow of sample fluids. In the illustrated embodiment, the sample cell 1010 may have a substantially spherical shape. The sample cell 1010 may alternatively have any other shape, such as cylindrical, rectangular, etc.

In various embodiments, the sample cell 1010 may be made of any suitable material with optical properties suitable for spectrophotometry. Such materials may include various glass compositions, quartz, transparent polymers, or others.

In some embodiments, a light source 1020 and a light detector 1022 may be positioned on opposite sides of the sample cell 1010. The light source may comprise a single-wavelength light source, multiple single-wavelength light sources (of the same or different wavelengths), a variable wavelength light source, multiple variable wavelength light sources, one or more multiple wavelength light sources, or various combinations of single-wavelength, multiple wavelength, and variable wavelength light sources. The light source may operate in any suitable part of the electromagnetic spectrum and may also comprise any other accompanying electronics or other components such as apertures, monochromators, or other optical or optoelectronic devices. The light detector may comprise any suitable detection devices and accompanying electronics, such as photomultiplier tubes, photodiodes, charged couple devices, photodiode arrays or any other light sensor or detector.

In various embodiments, a plurality of field inducing devices 1026 may be positioned at various locations adjacent to the sample cell 1010. For example, a pair of field inducing devices 1026 may be positioned on opposite sides of the sample cell 1010 along a line perpendicular to a line between the light source 1020 and the light detector 1022. Alternatively or in addition, a pair of field inducing devices 1026 may be positioned on opposite sides of the sample cell 1010 along a line parallel or at any other angle to a line between the light source 1020 and the light detector 1022. The field inducing devices 1026 may include any of the field inducing devices 820 described above with reference to FIG. 8-FIG. 13.

Figure 16A:
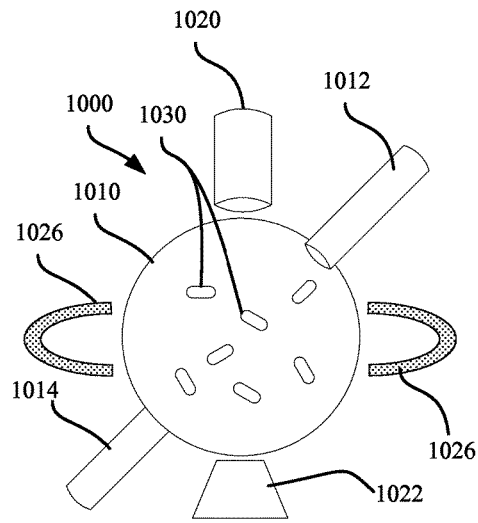
FIG. 16A-FIG. 16C are schematic diagrams illustrating a spectrophotometer comprising electromagnetic field inducing devices for orienting polar molecules in a sample cell, with polar molecules illustrated in various orientations.

FIG. 16A is an elevation-view illustration of a sample cell 1010 containing a plurality of elongated polar molecules 1030 (shown in exaggerated size for illustration) in arbitrary or random orientations, as they would tend to be in the absence of any aligning field. In this orientation, light from the light source 1020 will variously impinge on long sides, short sides or at various angles to each of the polar molecules 1030. If spectrophotometric measurements are taken with molecules in random orientations, the absorption spectrum based on light from the source 1020 received by the detector 1022 will tend to represent an average of the various orientations of the polar molecules.

Figure 16B:
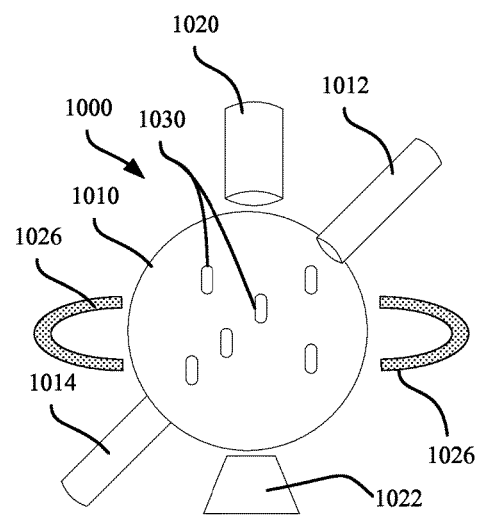

FIG. 16B illustrates the polar molecules 1030 oriented with their elongated axes parallel to the light source-detector axis. Spectrophotometric measurements taken with elongated polar molecules in this orientation may represent the absorption spectrum of only the small dimension of the aligned polar organic molecules.

Figure 16C:
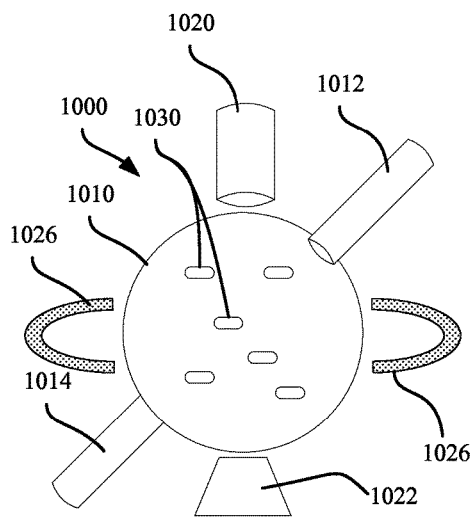

FIG. 16C illustrates the polar molecules 1030 oriented with their elongated axes perpendicular to the light source-detector axis. Spectrophotometric measurements taken with elongated polar molecules in this orientation may represent the absorption spectrum of only the large dimension of the aligned polar organic molecules.

In various embodiments, field inducing devices 1026 may be located in any desired positions relative to the light source-detector line so as to create fields to orient polar molecules in any desired orientation relative to the light source and detector. As described above one or more fields may interact with polar molecules in order to orient polar molecules in desired orientations at the intersection of the one or more fields and the polar molecules in the liquid.

Figure 16D:
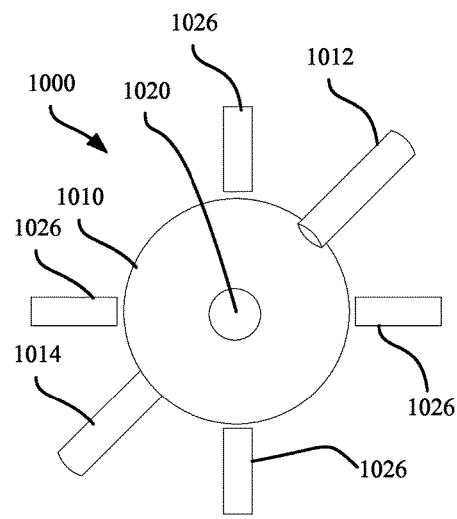
FIG. 16D is a schematic diagram illustrating a top-down view of the spectrophotometer of FIG. 16A showing optional additional field inducing devices.

For example, as shown in the plan view of FIG. 16D, four or more field inducing devices 1026 may be positioned adjacent the sample cell 1026.

The various absorption spectra of known solutions of polar organic molecules (elongated or non-elongated) aligned in various orientations may be evaluated to determine calibration data that may be used for characterizing unknown samples. In some embodiments, characterizing a single sample using a spectrophotometer such as those described with reference to FIG. 16A-FIG. 16D may comprise establishing a first field to position polar molecules in a first orientation and taking a first spectrophotometric measurement, then establishing a second field to position polar molecules in a second orientation and taking a second spectrophotometric measurement. In some embodiments, characterizing a sample may comprise comparing or combining the first and second photometric measurements.

In some embodiments, the strength of an induced field may be selected to orient a specific targeted polar organic molecule without affecting or minimally affecting other polar organic molecules.

These results of various measurements using a make-up module comprising a spectrophotometer can be characterized by the processor 324 (or another processor) to assess concentrations of different chemicals in the liquid samples, and may be used to assist in controlling the overall process 200 or specific aspects of the process 200.

In some embodiments, the spectrophotometer 1000 and sample cell 1010 may be configured for continuous in-line operation in which a sample fluid to be evaluated may be continuously flowed through the sample cell. The light source may be continuously or intermittently illuminated, and the field inducing device(s) may be configured to continuously or intermittently induce fields of desired orientations in the sample cell. The spectrophotometer controller may be configured to evaluate detected light signals based on a known field orientation and strength induced at a time at which light signals are detected.

In some embodiments, a spectrophotometer such as those described with reference to FIG. 16A-FIG. 16D may be used to identify, quantify, or characterize one or more inorganic polar compounds by orienting the one or more inorganic polar compounds in a desired orientation relative to the light source and the light detector.

Calcium Magnesium Acetate/Potassium Acetate Production

In some embodiments, the process 200 of FIG. 2 may be adapted to produce an output material 112 substantially comprising a solid acetate material that may be useful as a road salt or aggregate material. A specific example of an output material 112 in an aspect of the present disclosure may be calcium magnesium acetate (CMA).

CMA is a potential replacement material for sodium chloride in certain applications. Sodium chloride, also known as table salt, is used to reduce the freezing temperature of water on roadways to allow for safer driving conditions. Sand may also be used along with the sodium chloride to provide better traction in winter driving conditions. Although salt and sand mixtures are inexpensive to apply, these applications are harmful to the environment and they damage and corrode the vehicles that use these roadways. For example, the water runoff from salted roads adds both sodium and chlorine to local watersheds and water supplies, which must be removed during water treatment. Sodium and chlorine are both contaminants to local watersheds, and deter flora and fauna from growing and/or reproduction when present in higher concentrations.

A potential replacement for the salt/sand mixture is a different salt mixture containing a combination of calcium acetate and magnesium acetate. A possible mixture of calcium acetate and magnesium acetate is an approximate 50:50 mixture, but other percentages may be used without departing from the scope of the present disclosure. Both calcium acetate and magnesium acetate are environmentally friendly, biodegradable salts. CMA is currently used in areas having watersheds sensitive to high sodium and chlorine concentrations. Unlike sodium chloride that degrades into sodium and chlorine, CMA does not add any sodium or chlorine to these watersheds. CMA degrades into calcium and magnesium components, which act as micronutrients for plants and aquatic biology. The acetate may be naturally biologically consumed and converted to carbon dioxide and methane, which reduces ecological and watershed damage when compared to the effects of sodium and chlorine.

In an aspect of the present disclosure, CMA may be produced using the process 200 described herein. For example, VFA production process 106 of the process 200 using anaerobic degradation of organic wastes may be used to convert organic waste materials into substantial quantities of acetic acid. If allowed to proceed too far, the VFA production process 106 may result in the production of methane gas. Production of methane gas may be avoided or limited by performing anaerobic acid phase digestion of organic waste input materials until high concentrations of soluble acetic acid are produced in an aqueous effluent.

In some embodiments of a CMA production process, an anaerobic digester 406 and/or 412 may be used to produce a VFA rich stream which may contain acetic acid, other VFAs, and other carboxylic acids. The liquids produced by the digester may be filtered by one or more filters 426 and/or 428 (or otherwise separated as described herein) in order to obtain a concentrated acetic acid solution containing few if any other VFAs. For example, in some embodiments, the concentrated acetic acid solution may be an aqueous solution containing a mass percent acetic acid concentration of about 2% to about 12%, about 2% to about 4%, about 4% to about 8%, or about 8% to about 12%.

The concentrated aqueous acetic acid stream 434 may then be placed into an extraction column with a solvent which is immiscible or at least partially immiscible in water. In one embodiment, the added solvent is tri-octyl phosphoric oxide (TOPO) in kerosene. The solubility of the carboxylic acid in the solvent exceeds the solubility of the carboxylic acid in the aqueous mixture, such that a majority of the carboxylic acid is partitioned into the solvent.

The added solvent may be separated from the aqueous stream, and may be transferred to a second extractor and combined with alkali (e.g., potassium) or alkaline earth (e.g., calcium and/or magnesium) source materials that may be dissolved in a solvent. In one example, calcium and magnesium source materials include dolomitic lime which may contain equal parts calcium carbonate and magnesium carbonate and may be dissolved in a second solvent, which may include water or any other solvent suitable for dissolving calcium and/or magnesium source materials. Other calcium and/or magnesium source materials may include oyster shells, egg shells, or other suitable shells.

A mixture of calcium and magnesium source materials dissolved in the second solvent may be combined with the acetic acid solution dissolved in the added solvent in a second extractor. The mixture in the second extractor may form calcium acetate and magnesium acetate along with carbonate by-products dissolved and/or suspended in a solvent mixture. The carbonate by-products may be removed from the CMA-containing solvent mixture in a separation process (e.g., any of the separation processes described above, such as process 108). In some embodiments, the carbonates may be removed from the CMA-containing solvent mixture using a belt filter.

The CMA may be separated from the solvent containing the CMA using a spray dryer which may produce a powdered CMA salt as a final product. The solvents may then be recovered from the spray dryer, as well as any unreacted calcium and/or magnesium source materials (e.g., dolomitic lime).

If the output material 112 desired is potassium acetate, a similar process as described for CMA may be used. In such cases, a potassium source material such as potassium ash may be used in place of the calcium and/or magnesium source materials. The process may otherwise proceed substantially the same as described above.

In some embodiments, a calcium-magnesium salt or a potassium salt may be produced using other VFAs (VFAs) in place of or in addition to acetic acid. Such additional VFAs may include propionic acid, butyric acid, and valeric acid, which may be used to produce various combinations of acetic acid salts, propionic acid salts, butyric acid salts, and valeric acid salts. These salts can be formed using calcium, magnesium, or potassium.

Such salt mixtures may be less expensive to produce, and these salts are also all biodegradable. Further, since these salts also lower the freezing temperature of water, they would serve a similar purpose to CMA and/or sodium chloride, and still provide environmental benefits. These additional salts may be obtained by using use less filtration of the products of acid phase anaerobic digestion within the process 200 described herein. Further, manufacturing of such a salt mixture may allow for omission or modification of some of the steps of process 200 as described herein and still be within the scope of the present disclosure.

Figure 18:
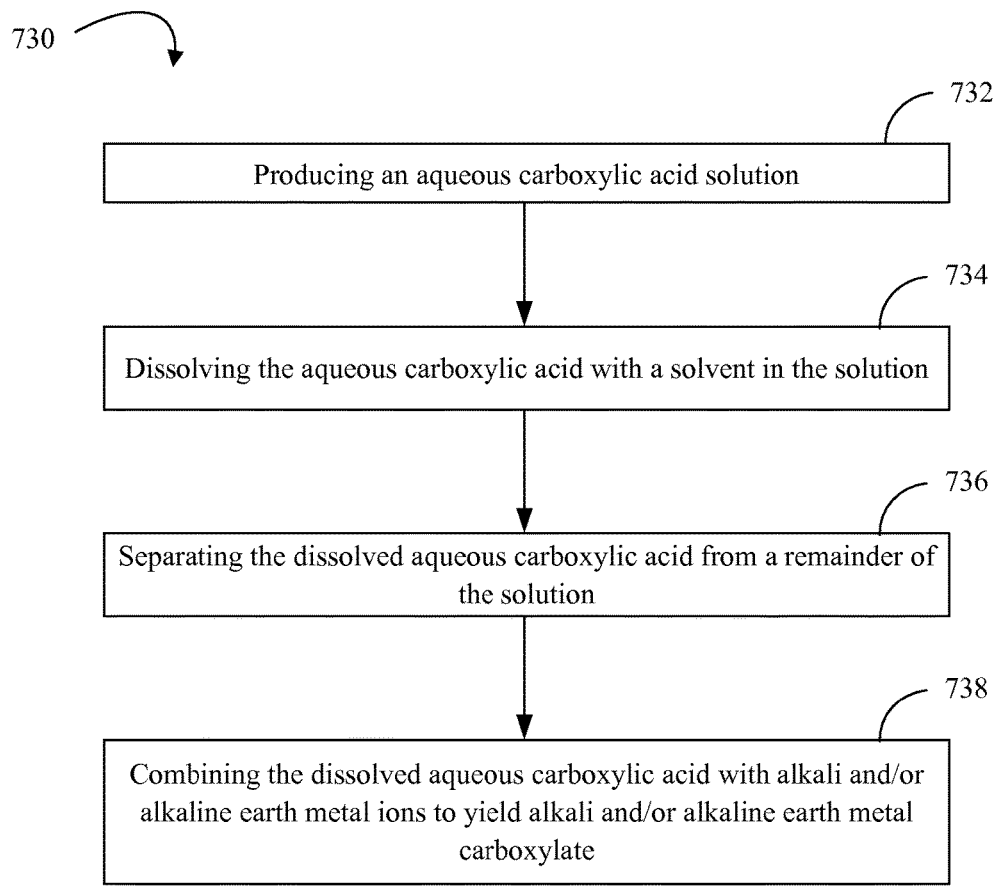
FIG. 18 is a process flow diagram illustrating a process for producing a chemical salt material.

FIG. 18 illustrates a process flow diagram illustrating a method 730 for producing alkali and/or alkaline earth metal carboxylates in accordance with an aspect of the present disclosure. In 732, an aqueous solution of carboxylic acids (or VFA(s)) is produced as shown in FIG. 2 and FIG. 3. In 734, the aqueous carboxylic acids (or VFA(s)) are combined with a solvent which is at least partially immiscible in water to yield a solution, as described with respect to FIG. 2, FIG. 3, and FIG. 5. In 736, the solvent with the dissolved carboxylic acids (or VFA(s)) is separated from the solution as described with respect to FIG. 2 and FIG. 5. In 738, the dissolved carboxylic acids (or VFA(s)) is combined with source of alkali and/or alkaline earth metal ions to yield alkali and/or alkaline earth metal carboxylates as described with respect to FIG. 2.

Electronic Controllers

As used herein, the term "controller," "electronic controller," "processor" and "computer" include one or more electronic controllers, processors, devices, modules, data stores, servers, networked computer, stand-alone computer, or other computing systems. In various embodiments, one or more controllers may be provided to automatically execute one or more of the processes, process steps, or actions described herein. For example, a controller may generally include any suitable computing hardware within which one or more sets or sequences of instructions may be executed to cause the system to perform any one or more of the processes or methods described herein. A controllers may be configured to operate one or more actuators such as electronic actuators, mechanical actuators or electromechanical actuators, which may include pumps, valves, servos, solenoids, hydraulic actuators, pneumatic actuators, thermal actuators, magnetic actuators, or others.

The controllers described herein, such as the processor 324, may be configured to implement one or more processes with modules (e.g., procedures, functions, subroutines, and so on) that perform the functions described herein. A machine-readable medium tangibly embodying instructions may be used in implementing the methodologies described herein. For example, software codes may be stored in a memory and executed by a processor unit. Memory may be implemented within the processor unit or external to the processor unit. As used herein, the term "memory" refers to types of long term, short term, volatile, nonvolatile, or other memory and is not to be limited to a particular type of memory or number of memories, or type of media upon which memory is stored.

If implemented in firmware and/or software, the functions may be stored as one or more instructions or code on a computer-readable medium. Examples include computer-readable media encoded with a data structure and computer-readable media encoded with a computer program. Computer-readable media includes physical computer storage media. A storage medium may be an available medium that can be accessed by a computer. By way of example, and not limitation, such computer-readable media can include RAM, ROM, EEPROM, CD-ROM or other optical disk storage, magnetic disk storage or other magnetic storage devices, or other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and its advantages have been described in detail, it should be understood that various changes, substitutions and alterations can be made herein without departing from the technology of the disclosure as defined by the appended claims. For example, relational terms, such as "above" and "below" are used with respect to a substrate or electronic device. Of course, if the substrate or electronic device is inverted, above becomes below, and vice versa. Additionally, if oriented sideways, above and below may refer to sides of a substrate or electronic device. Moreover, the scope of the present application is not intended to be limited to the particular configurations of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding configurations described herein may be utilized according to the present disclosure. Accordingly, the appended claims are intended to include within their scope such processes, machines, manufacture, compositions of matter, means, methods, or steps.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The steps of a method or algorithm described in connection with the disclosure may be embodied directly in hardware, in a software module executed by a processor, or in a combination of the two. A software module may reside in RAM, flash memory, ROM, EPROM, EEPROM, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can include RAM, ROM, EEPROM, CD-ROM or other optical disk storage, magnetic disk storage or other magnetic storage devices, or any other medium that can be used to carry or store specified program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

SPECIFIC EMBODIMENTS

In some aspects, the present disclosure relates to the production of bioplastic materials from organic waste products. Some embodiments of such systems and methods are recited below.

PHA Embodiment 1

A method for producing a PHA copolymer, the method comprising: separating a fluid mixture comprising volatile fatty acids (VFAs) from an organic waste material; analyzing the fluid mixture to determine a quantity of a first VFA and a second VFA in the fluid mixture; adjusting the quantity of the first VFA in the fluid mixture until the fluid mixture comprises a target quantity of the first VFA and a target quantity of the second VFA to yield a modified mixture; combining the modified liquid mixture with polyhydroxyalkanoate-producing bacteria; and extracting the polyhydroxyalkanoate copolymer from the fluid mixture.

PHA Embodiment 2

The method of PHA Embodiment 1, in which separating the fluid mixture from an organic waste material comprises extracting the fluid mixture from an acid-phase digester.

PHA Embodiment 3

The method of PHA Embodiment 1, in which adjusting the concentration of the first VFA comprises combining an additive with the fluid mixture.

PHA Embodiment 4

The method of PHA Embodiment 3, in which the additive is a liquid comprising a known quantity of the first VFA.

PHA Embodiment 5

The method of PHA Embodiment 3, in which the additive comprises a nutrient additive.

PHA Embodiment 6

The method of PHA Embodiment 1, in which adjusting the concentration of the first VFA comprises selectively removing a quantity of the VFA from the fluid mixture.

PHA Embodiment 7

The method of PHA Embodiment 1, in which the second VFA is physically larger than the first VFA in at least one dimension, and further comprising: directing the fluid mixture through a first conduit towards a first filter with a maximum pore size that is selected to allow at least the first VFA and the second VFA to pass therethrough while preventing compounds larger than the first VFA and the second VFA from passing through the first filter; directing first filtrate passing through the first filter towards a second filter with pores large enough to allow the first VFA to pass therethrough and small enough to inhibit the second VFA from passing through the second filter; and removing a liquid containing the second VFA from a conduit between the first filter and the second filter.

PHA Embodiment 8

The method of PHA Embodiment 7, further comprising inducing an electromagnetic field in the first conduit adjacent the second filter, the electromagnetic field having a strength and polarity selected to inhibit the second VFA from passing through the second filter.

PHA Embodiment 9

The method of PHA Embodiment 1, wherein the first VFA is acetic acid, the second VFA is propionic acid, and wherein the target ratio is a ratio of wt % of acetic acid to wt % of propionic acid of between about 0.4 and about and about 13.

PHA Embodiment 10

The method of PHA Embodiment 1, wherein the PHA copolymer resins extracted from the fluid mixture comprise hydroxybutyrate residues, hydroxyvalerate residues, and lactic acid residues.

PHA Embodiment 11

The method of PHA Embodiment 10, wherein the extracted copolymer comprises dry weight mass percents of about 50% to about 95% polyhydroxybutyrate, a measurable quantity of lactic acid of about one percent or less, and the balance polyhydroxyvalerate and trace impurities.

In some aspects, the present disclosure relates to fluid filtration technologies, and more specifically to systems and methods for electromagnetic filtration of polar molecules. Some embodiments of such systems and methods are recited below.

EMF Embodiment 1

A method for electromagnetic separation of a polar organic compound from an aqueous solution, the method comprising: applying an electromagnetic field to a region of a conduit adjacent to a membrane filter defining pores of a diameter d; contacting the membrane filter with an aqueous solution comprising a polar organic compound, wherein the diameter d exceeds a first molecular dimension of the polar organic compound, and a second molecular dimension of the polar organic compound exceeds the diameter d; and orienting the electromagnetic field with respect to the membrane filter to allow or inhibit passage of the polar organic compound through the pores.

EMF Embodiment 2

The method of EMF Embodiment 1, further comprising separating the at least one affected polar organic compound from a remainder of the solution with the electromagnetic field.

EMF Embodiment 3

The method of EMF Embodiment 1, further comprising orienting the at least one affected polar organic compound to pass through the membrane filter.

EMF Embodiment 4

The method of EMF Embodiment 3, in which a length or a width of a polar molecule in the at least one affected polar organic compound is larger than a pore size of the membrane filter.

EMF Embodiment 5

The method of EMF Embodiment 4, further comprising separating the at least one affected polar organic compound from a remainder of the solution with the electromagnetic field.

EMF Embodiment 6

The method of EMF Embodiment 1, in which exposing the membrane filter to the electromagnetic field further comprises varying the electromagnetic field to affect different ones of the plurality of polar organic compounds at different times.

EMF Embodiment 7

The method of EMF Embodiment 1, in which the electromagnetic field comprises an external magnetic field.

EMF Embodiment 8

The method of EMF Embodiment 1, in which the electromagnetic field comprises an electric field passed through the membrane filter.

EMF Embodiment 9

The method of EMF Embodiment 8, in which the membrane filter comprises electrodes to pass the electromagnetic field through the membrane filter.

EMF Embodiment 10

The method of EMF Embodiment 1, further comprising filtering the solution through a particle filter.

EMF Embodiment 11

An apparatus for electromagnetic separation of a polar organic compound from an aqueous solution, the apparatus comprising: a membrane filter defining pores having a longitudinal axis perpendicular to a plane of the membrane filter and an electromagnetic field generator configured to apply an electromagnetic field parallel or perpendicular to the plane of the membrane filter.

EMF Embodiment 12

The apparatus of EMF Embodiment 11, in which the at least one affected polar organic compound is separated from a remainder of the solution with the electromagnetic field.

EMF Embodiment 13

The apparatus of EMF Embodiment 11, further comprising orienting the at least one affected polar organic compound to pass through the membrane filter.

EMF Embodiment 14

The apparatus of EMF Embodiment 13, in which a length or a width of a polar molecule in the at least one affected polar organic compound is larger than a pore size of the membrane filter.

EMF Embodiment 15

The apparatus of EMF Embodiment 14, in which the membrane filter separates the at least one affected polar organic compound from a remainder of the solution using the electromagnetic field.

EMF Embodiment 16

The apparatus of EMF Embodiment 11, in which the electromagnetic field generator varies the electromagnetic field to affect different ones of the plurality of polar organic compounds at different times.

EMF Embodiment 17

The apparatus of EMF Embodiment 11, in which the electromagnetic field generator creates an external magnetic field around the membrane filter.

EMF Embodiment 18

The apparatus of EMF Embodiment 11, in which the electromagnetic field generator comprises a power supply electrically joined to a pattern of conductive wires adjacent to the membrane filter.

EMF Embodiment 19

The apparatus of EMF Embodiment 18, in which the conductive wires are arranged in a spiral pattern.

EMF Embodiment 20

The apparatus of EMF Embodiment 18, in which the conductive wires are arranged in a grid pattern, and wherein the power supply is switchably joined to each of the wires in the grid pattern.

EMF Embodiment 21

The apparatus of EMF Embodiment 11, in which the field generator comprises an electromagnet.

EMF Embodiment 22

The apparatus of EMF Embodiment 11, in which the field generator comprises a power supply electrically joined to windings of conductive wire surrounding a conduit containing the membrane filter.

EMF Embodiment 23

The apparatus of EMF Embodiment 11, further comprising a particle filter, coupled to the membrane filter, for filtering the solution.

EMF Embodiment 24

The apparatus of EMF Embodiment 11, wherein the electromagnetic field generator is further configured to change from applying a first field parallel to the filter to a applying a second field perpendicular to the filter by changing a direction or a conductive path of one or more electric currents.

In some aspects, the present disclosure relates to aerobic and anaerobic digesters, and more specifically to aerobic and anaerobic digesters configured to produce biopolymer resins from biological waste materials. Some embodiments of such systems and methods are recited below.

Digester Embodiment 1

A plug flow digester apparatus comprising: a digestion chamber defining a longitudinal axis between an inlet end and an outlet end and openings along the longitudinal axis; catch bins exterior to and along the longitudinal axis of the digestion chamber, wherein the catch bins are proximate the openings defined in the digestion chamber, and each catch bin is fluidically coupled to fluid processing apparatuses; a screen positioned between the digestion chamber and the catch bins, the screen configured to allow passage of a liquid from the openings of the digestion chamber to the catch bins; and a liquid composition analyzer fluidically coupled to each catch bin and configured to assess a composition of the liquid in each catch bin; wherein the plug flow digester apparatus is configured to provide the liquid from each catch bin to one of the fluid processing apparatuses by operating one or more fluid delivery devices based at least in part on the composition of the liquid in each catch bin.

Digester Embodiment 2

The digester of Digester Embodiment 1, further comprising a rotating helical drive ribbon configured to advance digestible material from the inlet end to the outlet end at a controllable rate.

Digester Embodiment 3

The digester of Digester Embodiment 1, in which the inlet end is elevated above the outlet end such that digestible material flows from the inlet end to the outlet end by gravity.

Digester Embodiment 4

The digester of Digester Embodiment 1, further comprising a piston configured to advance digestible material from the inlet end to the outlet end at a controllable rate.

Digester Embodiment 5

The digester of Digester Embodiment 1, further comprising a shut-off panel arranged to selectively prevent liquid from dropping into at least one catch bin.

Digester Embodiment 6

A method of obtaining volatile fatty acids from biodegradable waste material, the method comprising: directing a quantity of biodegradable waste material into an input end of a digestion chamber defining a longitudinal axis; advancing the biodegradable waste material from the input end of the digestion chamber to an output end of the digestion chamber at a predetermined rate; withdrawing a liquid from a plurality of points along the longitudinal axis of the digestion chamber; analyzing a make-up of each of the withdrawn liquids; and based on a result of analyzing each liquid, returning the liquid to the digestion chamber or directing the liquid to an external process.

The method of Digester Embodiment 6, wherein the external process is a bioplastic production process.

In some aspects, the present disclosure relates to spectrophotometric devices and methods, and more specifically to systems and methods for spectrophotometric evaluation of aligned polar molecules. Some embodiments of such systems and methods are recited below.

Photo Embodiment 1

A spectrophotometer comprising: a sample chamber; a light source arranged to direct light through the sample chamber; a light detector arranged to receive light transmitted through the sample chamber by the light source; a field inducing device configured to induce a field within the sample chamber between the light source and the light detector.

Photo Embodiment 2

The device of Photo Embodiment 1, further comprising a controller containing instructions to evaluate light detected by the light detector based on an orientation or strength of a field induced by the field inducing device.

Photo Embodiment 3

The device of Photo Embodiment 1, in which the field inducing device comprises an electromagnet.

Photo Embodiment 4

The device of Photo Embodiment 1, in which the field inducing device comprises a first pair of electromagnets and a second pair of electromagnets adjacent to the sample chamber.

Photo Embodiment 5

The device of Photo Embodiment 4, further comprising a controller configured to energize the first pair of electromagnets at different times than the second pair of electromagnets.

Photo Embodiment 6

The device of Photo Embodiment 1, further comprising an inflow conduit joined to the sample chamber.

Photo Embodiment 7

The device of Photo Embodiment 6, further comprising an outflow conduit joined to the sample chamber.

Photo Embodiment 8

The device of Photo Embodiment 1 in which the field inducing device comprises a plurality of electromagnets.

Photo Embodiment 9

The device of Photo Embodiment 1 in which the field inducing device comprises a plurality of electrically conductive windings surrounding the sample chamber.

Photo Embodiment 10

The device of Photo Embodiment 1 in which the field inducing device is configured to change an orientation of an induced field from a first orientation to a second different orientation by changing a direction or conductive path of electric current delivered to the field inducing device.

Photo Embodiment 11

A method of spectrophotometrically analyzing a sample, the method comprising: placing the sample in a sample chamber; inducing an electromagnetic field in the sample chamber; directing a light from a light source through the sample and receiving light transmitted through the sample with a light detector; controlling a strength or an orientation of the electromagnetic field to orient a constituent of the sample in a predetermined orientation relative to the light source or the light detector.

Photo Embodiment 12

The method of Photo Embodiment 11, wherein placing the sample in the sample chamber comprises continuously flowing the sample through the sample chamber.

Photo Embodiment 13

The method of Photo Embodiment 11, further comprising determining a composition of the sample based on signals detected by the light detector and the strength or orientation of the electromagnetic field.

In some aspects, the present disclosure relates to acetate-containing compositions, and more specifically to calcium magnesium acetate (CMA) compositions. Some embodiments of such systems and methods are recited below.

CMA Embodiment 1

A method of producing an alkali metal or alkaline earth metal carboxylate, the method comprising:
combining acidogenic bacteria with a feedstock comprising an organic waste product to yield a aqueous mixture comprising a carboxylic acid;
combining the aqueous mixture with a solvent to yield a first modified aqueous mixture, wherein the solvent is at least partially immiscible in water, and the solubility of the carboxylic acid in the solvent exceeds the solubility of the carboxylic acid in the aqueous mixture;
partitioning a majority of the carboxylic acid into the solvent to yield a carboxylic acid-rich solvent;
separating the carboxylic acid-rich solvent from the first modified aqueous mixture;
combining the carboxylic acid-rich solvent with an aqueous solution comprising alkali metal ions or alkaline earth metal ions to yield a second modified aqueous mixture; and
recovering an alkali metal or alkaline earth metal carboxylate from the second modified aqueous mixture.

CMA Embodiment 2

The method of CMA Embodiment 1, wherein the carboxylic acid is a volatile fatty acid.

CMA Embodiment 2

The method of CMA Embodiment 1, wherein the alkaline earth metal ions comprise calcium ions, magnesium ions, or a combination thereof.

CMA Embodiment 4

The method of CMA Embodiment 1, wherein the alkali metal ions comprise potassium ions.

CMA Embodiment 5

The method of CMA Embodiment 1, wherein the solvent comprises tri-octyl phosphoric oxide in kerosene.

CMA Embodiment 6

The method of CMA Embodiment 1, wherein an alkali carboxylate is recovered, and the alkali metal carboxylate comprises potassium acetate.

CMA Embodiment 7

The method of CMA Embodiment 1, wherein an alkaline earth metal carboxylate is recovered, and the alkaline earth metal carboxylate comprises calcium acetate, magnesium acetate, or a combination thereof.

CMA Embodiment 8

The method of CMA Embodiment 1, wherein separating the solvent from the first modified aqueous mixture comprises filtering the first modified aqueous mixture.

CMA Embodiment 9

The method of CMA Embodiment 1, wherein the aqueous solution comprising alkali metal ions comprises an aqueous solution comprising potassium ash.

CMA Embodiment 10

The method of CMA Embodiment 1, wherein the aqueous solution comprising alkaline earth metal ions comprises an aqueous solution comprising dolomitic lime, oyster shells, or egg shells.

CMA Embodiment 11

The method of CMA Embodiment 1, wherein the carboxylic acid is formed via anaerobic digestion of the organic waste product.

CMA Embodiment 12

The method of CMA Embodiment 1, wherein the anaerobic digestion comprises acid phase anaerobic digestion of the organic waste product.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and features disclosed herein.

What is claimed is:
1. A method of producing a polyhydroxyalkanoate copolymer from an organic waste product, the method comprising:
liquefying the organic waste product to yield a liquefied organic waste product, wherein the organic waste product is a non-homogeneous mixture comprising solids, and liquefying the organic waste product comprises contacting the organic waste product with hydrolytic bacteria to hydrolyze the organic waste product;

combining acidogenic bacteria with a feedstock comprising the liquefied organic waste product to yield a liquid mixture comprising a first volatile fatty acid and a second volatile fatty acid; assessing a wt % of the first volatile fatty acid and a wt % of the second volatile fatty acid in the liquid mixture based on the total weight of the carboxylic acids in the liquid mixture, the total weight of volatile fatty acids in the liquid mixture, or the total weight of lactic acid and volatile fatty acids in the liquid mixture;

after assessing the wt % of the first volatile fatty acid and the wt % of the second volatile fatty acid in the liquid mixture, adjusting a ratio of the wt % of the first volatile fatty acid to the wt % of the second volatile fatty acid in the liquid mixture to yield a modified liquid mixture having a ratio of the wt % of the first volatile fatty acid to the wt % of the second volatile fatty acid in the modified liquid mixture in a target range;

after adjusting a ratio of the wt % of the first volatile fatty acid to the wt % of the second volatile fatty acid in the liquid mixture to yield the modified liquid mixture, combining the modified liquid mixture with polyhydroxyalkanoate-producing bacteria to yield a polyhydroxyalkanoate copolymer; and extracting the polyhydroxyalkanoate copolymer from the polyhydroxyalkanoate-producing bacteria.

2. The method of claim 1, wherein liquefying the organic waste product further comprises converting the organic waste product into short-chain soluble carbohydrates.

3. The method of claim 1, wherein adjusting the relative concentration of the first volatile fatty acid and the second volatile fatty acid comprises combining an additional quantity of the first volatile fatty acid, an additional quantity of the second volatile fatty acid, or both to the liquid mixture.

4. The method of claim 1, wherein adjusting the relative concentration of the first volatile fatty acid and the second volatile fatty acid comprises removing a quantity of the first volatile fatty acid, a quantity of the second volatile fatty acid, or both from the liquid mixture.

5. The method of claim 4, wherein the second volatile fatty acid is physically larger than the first volatile fatty acid in at least one dimension, and further comprising:

directing the fluid mixture through a first conduit towards a first filter with a maximum pore size that is selected to allow at least the first volatile fatty acid and the second volatile fatty acid to pass therethrough while preventing compounds larger than the first volatile fatty acid and the second volatile fatty acid from passing through the first filter;

directing the first filtrate passing through the first filter towards a second filter with pores large enough to allow the first volatile fatty acid to pass therethrough and small enough to inhibit the second volatile fatty acid from passing through the second filter; and removing a liquid containing the second volatile fatty acid from a conduit between the first filter and the second filter.

6. The method of claim 5, further comprising inducing an electromagnetic field in the first conduit adjacent the second filter, the electromagnetic field having a strength and polarity selected to inhibit the second volatile fatty acid from passing through the second filter.

7. The method of claim 1, wherein the modified liquid mixture comprises at least two of acetic acid, propionic acid, lactic acid, butyric acid, iso-butyric acid, valeric acid, iso-valeric acid, and hexanoic acid.

8. The method of claim 7, wherein the modified liquid mixture comprises at least 30 wt % acetic acid, 0 wt % to 70 wt % propionic acid, 0 wt % to 30 wt % lactic acid, and 0 wt % to 50 wt % butyric acid, 0 wt % to 30 wt % iso-butyric acid, 0 wt % to 50 wt % valeric acid, 0 wt % to 30 wt % iso-valeric acid, and 0 wt % to 50 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture.

9. The method of claim 7, wherein the modified liquid mixture comprises at least 60 wt % acetic acid, 0 wt % to 40 wt % propionic acid, 0 wt % to 10 wt % lactic acid, 0 wt % to 40 wt % butyric acid, 0 wt % to 40 wt % iso-butyric acid, 0 wt % to 40 wt % valeric acid, 0 wt % to 40 wt % iso-valeric acid, and 0 wt % to 40 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture.

10. The method of claim 7, wherein the modified liquid mixture comprises at least 80 wt % acetic acid, 0 wt % to 20 wt % propionic acid, 0 wt % to 5 wt % lactic acid, 0 wt % to 20 wt % butyric acid, 0 wt % to 20 wt % iso-butyric acid, 0 wt % to 20 wt % valeric acid, 0 wt % to 20 wt % iso-valeric acid, and 0 wt % to 20 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture.

11. The method of claim 7, wherein the modified liquid mixture comprises 60 wt % to 80 wt % acetic acid, 10 wt % to 20 wt % propionic acid, 0 wt % to 10 wt % lactic acid, 5 wt % to 20 wt % butyric acid, 0 wt % to 7 wt % iso-butyric acid, 0 wt % to 10 wt % valeric acid, 0 wt % to 7 wt % iso-valeric acid, and 0 wt % to 10 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture.

12. The method of claim 7, wherein the modified liquid mixture comprises 75 wt % to 80 wt % acetic acid, 20 wt % to 25 wt % propionic acid, 0 wt % to 1 wt % lactic acid, 0 wt % to 5 wt % butyric acid, 0 wt % to 1 wt % iso-butyric acid, 0 wt % to 5 wt % valeric acid, 0 wt % to 5 wt % iso-valeric acid, and 0 wt % to 1 wt % hexanoic acid based on the total weight of carboxylic acids in the modified liquid mixture, the total weight of volatile fatty acids in the modified liquid mixture, or the total weight of lactic acid and volatile fatty acids in the modified liquid mixture.

13. The method of claim 7, wherein the modified liquid mixture comprises 80 wt % to 100 wt %, 60 wt % to 80 wt %, 40 wt % to 60 wt %, 20 wt % to 40 wt %, or 0 wt % to 20 wt % of acetic acid and propionic acid based on the total weight of carboxylic acids in the modified liquid mixture, the total weight of volatile fatty acids in the modified liquid mixture, or the total weight of lactic acid and volatile fatty acids in the modified liquid mixture.

14. The method of claim 7, wherein the modified liquid mixture comprises a ratio of wt % of acetic acid to wt % of propionic acid in a range of 0.4 to 13.

15. The method of claim 14, wherein the modified liquid mixture comprises a ratio of wt % of acetic acid to wt % of propionic acid of 3/7, 29/16, 9/5, 3/2, 39/11, 22/3, or 93/7.

16. The method of claim 1, wherein the polyhydroxyalkanoate copolymer comprises polyhydroxybutyrate and polyhydroxyvalerate.

17. The method of claim 16, wherein the polyhydroxyalkanoate copolymer comprises lactic acid residues.

18. The method of claim 16, wherein the polyhydroxyalkanoate copolymer comprises 50 wt % to 90 wt % (dry matter) of polyhydroxybutyrate, up to 1 wt % lactic acid residue, and the balance polyhydroxyvalerate.

19. The method of claim 1, wherein adjusting the ratio of the wt % of the first volatile fatty acid to the wt % of the second volatile fatty acid in the liquid mixture to yield the modified liquid mixture occurs automatically.

20. The method of claim 1, wherein adjusting the ratio of the wt % of the first volatile fatty acid to the wt % of the second volatile fatty acid comprises fermenting the liquid mixture at a pH in a range of 4 to 6 to yield the modified liquid mixture.

21. The method of claim 1, wherein adjusting the ratio of the wt % of the first volatile fatty acid to the wt % of the second volatile fatty acid in the liquid mixture to yield the modified liquid mixture comprises a feedback process.

22. The method of claim 1, further comprising, after combining the modified liquid mixture with the polyhydroxyalkanoate-producing bacteria, maintaining the ratio of the wt % of the first volatile fatty acid to the wt % of the second volatile fatty acid in the target range.

* * * * *